US012583131B2

(12) United States Patent
Parietti et al.

(10) Patent No.: US 12,583,131 B2
(45) Date of Patent: Mar. 24, 2026

(54) APPARATUS FOR FACILITATING AUTOMATION OF VESSELS

(71) Applicant: Multiply Labs Inc., San Francisco, CA (US)

(72) Inventors: Federico Parietti, San Francisco, CA (US); Adrian Claudio Tanner, Oakland, CA (US)

( * ) Notice: Subject to any disclaimer, the term of this patent is extended or adjusted under 35 U.S.C. 154(b) by 0 days.

(21) Appl. No.: 19/011,527

(22) Filed: Jan. 6, 2025

(65) Prior Publication Data

US 2025/0223540 A1 Jul. 10, 2025

Related U.S. Application Data

(60) Provisional application No. 63/698,008, filed on Sep. 23, 2024, provisional application No. 63/618,280, filed on Jan. 5, 2024.

(51) Int. Cl.
| | |
|---|---|
| *B25J 15/04* | (2006.01) |
| *B01L 3/00* | (2006.01) |
| *C12M 1/00* | (2006.01) |
| *C12M 1/36* | (2006.01) |
| *C12M 3/00* | (2006.01) |
| *F16L 37/00* | (2006.01) |
| *F16L 37/084* | (2006.01) |
| *G01N 35/00* | (2006.01) |

(52) U.S. Cl.
CPC .......... *B25J 15/0408* (2013.01); *C12M 23/38* (2013.01); *C12M 23/40* (2013.01); *C12M 23/42* (2013.01); *C12M 23/44* (2013.01); *C12M 23/46* (2013.01); *C12M 23/48*

(2013.01); *C12M 29/04* (2013.01); *C12M 29/06* (2013.01); *C12M 41/48* (2013.01); *F16L 37/002* (2013.01); *F16L 37/084* (2013.01); *G01N 35/0099* (2013.01); *B01L 3/563* (2013.01)

(58) Field of Classification Search
CPC ...... C12M 41/48; C12M 23/38; C12M 23/42; C12M 23/44; C12M 23/46; C12M 29/04
USPC ....................................... 435/289.1
See application file for complete search history.

(56) References Cited

U.S. PATENT DOCUMENTS

| | | | | |
|---|---|---|---|---|
| 2010/0276309 A1* | 11/2010 | Murasato | .......... | B01L 3/502715 206/219 |
| 2021/0002599 A1* | 1/2021 | Griffin | .................... | C12M 41/34 |
| 2024/0390897 A1* | 11/2024 | Azersky | ................. | C12M 35/02 |

* cited by examiner

*Primary Examiner* — Michael L Hobbs
*Assistant Examiner* — Lenora A Abel
(74) *Attorney, Agent, or Firm* — Morgan, Lewis & Bockius LLP

(57) ABSTRACT

A cartridge for facilitating automation of a vessel includes a cartridge body, an adapter for removably connecting the vessel to the cartridge body, and at least one connection unit for fluidic communication with the vessel. A connection unit includes a retainer, a port body, a connector, and a tube. The retainer is fixed on or integrally formed with a wall of the cartridge body. The port body is coupled to the retainer and has a distal end portion positioned exterior to the cartridge body. The connector is housed by the port body and has a first end and a second end, where the first end is positioned outside of the cartridge body. The tube selectively connects the second end of the connector to a port of the vessel.

25 Claims, 51 Drawing Sheets

100

122

163

161

165

150

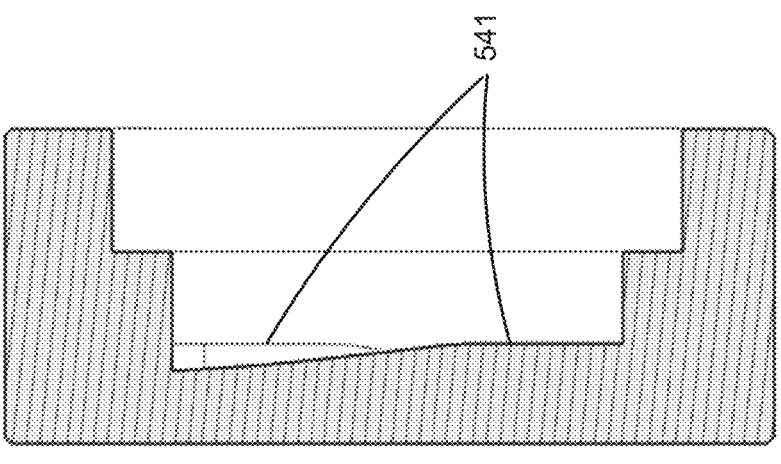
Figure 5G
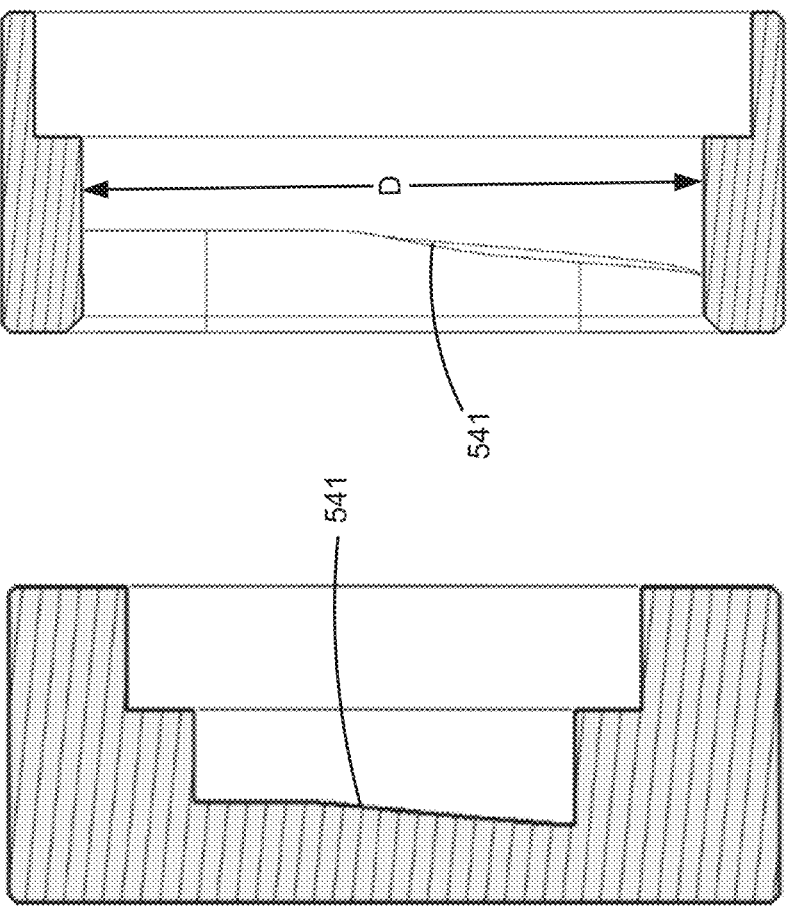
Figure 5F
Figure 5E

600

100

110

600

700

750
740
760
750
740
730
732
731
720
721
710

100
700
110

870

1000

APPARATUS FOR FACILITATING AUTOMATION OF VESSELS

CROSS-REFERENCE TO RELATED APPLICATION

The present application claims priority to United States Provisional Patent Application No.: 63/618,280 filed Jan. 5, 2024, and United States Provisional Patent Application No.: 63/698,008 filed Sep. 23, 2024, each of which is hereby incorporated by reference in its entirety for all purposes.

TECHNICAL FIELD

The present disclosure generally relates to devices, systems and methods for facilitating automated manufacturing at a biological foundry, and in particular to apparatuses for facilitating automation of vessels such as bioreactors.

BACKGROUND

Cell therapies are next-generation drugs where live cells are used to treat a subject. This is in contrast with traditional small-molecule and biologic drugs, where small or large molecules—but not whole living cells—are used to treat patients. Many of the most recent and promising innovations in medicine are represented by cell therapies in which the cells of a subject (either the patient or a donor) are extracted, genetically engineered in a lab, grown in an incubator, and finally infused in the patient in order to achieve a therapeutic effect. However, despite the life-saving effects of many cell therapies, there are significant bottlenecks to their widespread adoption. For instance, one obstacle is represented by the current limits in manufacturing capacity for cell therapies. Conventional cell therapy production processes are still largely labor-based and inefficient.

Traditionally, cell therapies are produced with labor-intensive processes. These conventional processes require not only a large number of manufacturing operators, but also the employment of highly skilled (and expensive) technicians. These constraints make it particularly difficult to manufacture cell therapies at an industrial scale. Cell therapy manufacturing processes are low-scale and labor-intensive because they were originally developed in the context of academic research. The original lab processes—which were developed to demonstrate the feasibility of cell therapies—were then hastily modified and retrofitted in order to fulfill regulatory requirements and achieve good manufacturing practices.

This conventional approach allowed drug manufacturers to bring to the market the first approved cell therapies. However, this labor-intensive, lab-oriented approach is unsuitable to achieve industrial scale. At their core, current cell manufacturing processes were designed to be manually completed by highly trained personnel—such as the researchers that conduct scientific experiments in an academic environment. Requiring this type of skillset becomes a disadvantage in an industrial setting. Cell manufacturing processes depend on highly trained, highly educated manual labor, and this makes them incompatible with the efficiency of mass-manufacturing industrial processes.

The dominant conventional approach to cell manufacturing is based on a set of separate individual pieces of manufacturing equipment placed on a clean room bench. This manufacturing process still looks exactly like a research laboratory, where all the machinery is manually operated and directly supervised by highly skilled operators.

In order to execute the cell manufacturing processes, these skilled operators gown up, enter a clean room, and manually activate the machines. The operators also transfer the batch material from machine to machine, manually sample the batches to perform quality control testing, ensure that reagents are delivered to the cells, and ensure that waste material is removed. This labor-based conventional approach is very different from the organization of industrial-scale processes, where most tasks are autonomously executed by specialized machinery, which is supervised by ordinary manufacturing technicians (not engineers, nor scientists).

As such, the conventional labor-based approach to cell therapy manufacturing has at least three fundamental limits. First, the conventional approach is not scalable and not robust to operator variability. Because the conventional approach is extremely labor-intensive, cell therapy manufacturing is limited to small-scale applications. Increasing throughput beyond a few hundred products per year has proven extremely difficult, because such an effort would require hiring, training, retaining, and managing a large number of highly skilled, expensive operators. Moreover, labor-based processes are typically unable to reach industrial scale, and cell manufacturing is not an exception. This pronounced reliance of labor presents additional disadvantages, including the fact that—because of operator variability—the yield and the features of the finished cell therapy product are hard to predict and to control. This operator variability makes scaling the process of manufacturing cell therapy products even harder—particularly in terms of margins, in which a higher number of rejected batches increases the cost per batch.

Additionally, the conventional approach to manufacturing cell therapy products is inefficient. Since individual machines for the cell therapy manufacturing process are utilized in series (e.g., the machines are used one at a time, with a single batch manually moved from a piece of machinery to the next), when a machine is active all the others are idle. This results in a low utilization rate for all machines, since most of the machines are waiting for the batch to arrive, while a single machine is being used. The problem of a very low utilization rate is particularly evident for cell manufacturing processes, which are characterized by machines with markedly different cycle times. More specifically, systems like bioreactors process a single batch for weeks, while machines like thawing and freezing systems are only used for a few hours on a single batch. This results in utilization rates that are even lower for the faster machines—because the slower machines are the bottleneck and limit the rate of the rest of the serial process.

Finally, the conventional approach to manufacturing cell therapy products has low throughput. Because the process is managed and executed by human operators, only one batch can be produced at any given time on a serial production line. For instance, if two batches were manufactured at the same time on the same production line, in fact, there would be high risk of cross-contamination or of mix-up errors by the operators. Since all the serial machines are used for just one product at a time, the resulting throughput of the production line is extremely low. As a reference, typically a cell therapy product takes two to three weeks to be manufactured. This means that, in order to avoid mix-ups, a whole production line must be reserved for a single product for about half of a month—a rate that is incompatible with industrial scale. Because of this temporal constraint, a whole manufacturing suite (typically consisting of about 1,000 square feet of clean room space) must be reserved for a single serial production line. Therefore, the only way to increase throughput via this conventional approach is by creating facilities with multiple independent suites that replicate the same process. However, each suite can only handle one product at a time, occupies significant clean room space, and is entirely operated by skilled labor. As such, this conventional approach is not scalable, and not suitable to manufacture more than a few hundreds of cell therapies per year—with very high production costs.

One solution to this conventional approach are closed system cell therapy machines that have been developed to attempt to address the shortcomings of the traditional approach. However, even this solution is still labor-intensive and inadequate to reach industrial scale. For instance, this solution can be described as an end-to-end serial system that is contained into a single machine. Different parts of the same machine perform the different steps of the production process. In other words, a single piece of equipment contains all the sub-systems that are needed to perform the cell manufacturing process. An intricate set of tubes connects all of these systems, so that the cell therapy product (which is typically in liquid form) can be transferred from one sub-system to the next without being exposed to the external environment, which provides the closed system.

However, these end-to-end, closed systems are sold as a unique piece of machinery. As such, the machinery cannot be modified by the buyer: once a system is bought, the buyer is constrained to run the exact process for which that machine was designed. Additionally, the machinery still needs to be operated by a highly skilled technician, who needs to perform a complicated set of actions to set up, monitor, and manage the manufacturing process. More specifically, highly trained operators set up the intricate network of tubes that is required by each batch. These operators are also tasked with opening and closing the valves that regulate the flow of material from one part of the system to the next. Furthermore, technicians also manually sample the batch, whenever testing is needed for quality control.

As such, this prior closed system solution suffers disadvantages, in that the closed system solution is overcomplicated. Setting up dozens of tubes, liquid reservoir bags, and reagents requires highly trained labor. This setting up process also takes a long time—even for a skilled technician—to set up, operate, and supervise the machinery. This results in the need for a number of operators that increases proportionally to the number of production system—making it impossible to achieve industrial scale and contain manufacturing costs.

Furthermore, the prior closed system solution is inefficient. Since the architecture of the closed system is still serial, this approach suffers of the same efficiency constraints as the dominant (bench-based) approach. At any given time, most of the subsystems inside of the end-to-end machine are unused. This happens because only one system can be used at a time—this is a serial production line with the hard limit of a single product per production run. Moreover, since some parts of the process are particularly slow (for example, the expansion of the cells into a bioreactor), the subsystems are characterized by an even lower utilization rate than the slower subsystems of the machinery.

Additionally, this closed system lacks design flexibility. This inflexibility drawback is typical of closed systems that are built specifically to execute a particular process. Once the machinery is bought, it is not possible to replace an outdated subsystem with a better one (for example, a subsystem that performs a task better, or with a higher throughput). Any modification to the original closed system machinery requires massive engineering and retooling costs, comparable to building a whole new end-to-end system from scratch. This lack of flexibility is particularly disadvantageous in the case of cell therapy manufacturing—where processes are often tuned and improvement at all stages of clinical development.

Moreover, since each closed system is end-to-end and can only manufacture a single product at a time, the only way to increase throughput is to buy more of these closed systems. This in turn worsens the above-mentioned complexity and underutilization problems. In other words, deploying more complex systems increases the need for skilled operators, which in turn increases the cost of manufacturing. Since each machine is largely underutilized (only one subsystem is active at any given time), chronic underutilization also characterizes a facility that is equipped with multiple end-to-end systems.

Additionally, a major problem of labor-based cell manufacturing processes is that human operators need to sample each batch manually. In cell manufacturing processes, sterility must be always ensured. This is particularly important, because cell therapies cannot be sterilized at the end of the manufacturing process (that would kill the cells). At the same time, guaranteeing the quality of cell manufacturing processes requires a large number of quality control steps. And, in order to perform quality control tests, the cell therapy products must be frequently sampled (e.g., a part of the product must be removed from the batch, while ensuring the sterility of both the sample and the product). In conventional cell manufacturing processes, sampling tasks are executed by human operators.

One disadvantage of this conventional approach to sampling is that human operators are a significant potential source of contamination for cell therapy products. Every time a batch is sampled manually, there is a high risk of contamination because the operator must manually remove a part of the liquid containing the cell product. Even semi-automated sampling procedures, where an operator activates a system that performs the sampling task, present significant risk of contamination due to requiring the presence of a human technicians in close proximity to the process.

Another critical issue is that sampling procedures are performed extremely frequently in cell manufacturing processes. Cell therapy products are sometimes sampled multiple times during a single day. Since cell manufacturing processes have a long completion time (most require more than a week, and many can take up to fifteen to twenty days), manual sampling is repeated dozens of times for every single batch. Repeating risky sampling procedures with this extreme frequency greatly increases the risk of contamination.

Given the above background, there is a need in the art for improved systems, methods, and apparatuses for facilitating an improved manufacture of cell therapies that addresses these dilemmas.

The information disclosed in this background section is only for enhancement of understanding of the general background of the invention and should not be taken as an acknowledgement or any form of suggestion that this information forms the prior art already known to a person skilled in the art.

SUMMARY

To address the shortcomings discussed above and/or other issues, the present disclosure provides apparatuses that can facilitate automation of one or more vessels such as biore-actor devices. An apparatus generally includes a cartridge body, an adapter for removably connecting a vessel to the cartridge body, and at least one connection unit disposed at the cartridge body for fluidic communication with the vessel. In various embodiments, the apparatus includes a novel design that takes an industry standard vessel (e.g., a biore-actor) and adapts it to a robot compatible compact cartridge with gripping features, floating ports, concealed tubing, docking features, and/or other features. As such, the apparatuses of the present disclosure advantageously leverage advanced robotic features and technologies while retaining the benefits of conventional closed-system processes (e.g., providing a sterile clean room environment). This enables the transformation of cellular engineering target manufacturing from labor-based and low-throughput processes to fully industrialized, high-throughput processes with high scale, efficiency and repeatability.

In various embodiments, the present disclosure provides a cartridge for facilitating automation of a vessel having a cap and at least one vessel port. The cartridge includes a cartridge body, an adapter and at least one connection unit. The cartridge body includes a side wall, an upper wall and an interior, where the upper wall is connected to or formed with an upper portion of the side wall, and the interior is defined by the side wall and the upper wall. The adapter is disposed in the interior of the cartridge body and connected to or formed with the cartridge body, and configured for removably connecting the vessel to the cartridge body. Each respective connection unit in the at least one connection unit includes a corresponding retainer, a corresponding port body, a corresponding connector and a corresponding tube. The corresponding retainer is fixed on or integrally formed with the upper wall of the cartridge body. The corresponding port body is coupled to the corresponding retainer and has a corresponding distal end portion positioned exterior to the cartridge body. The corresponding connector is housed by the corresponding port body and has a corresponding first end and a corresponding second end, where the corresponding first end is positioned outside of the cartridge body. The corresponding tube is configured for connecting the corresponding second end of the corresponding connector to a vessel port in the at least one vessel port of the vessel.

In some embodiments, the vessel is a gas permeable rapid expansion bioreactor device.

In some embodiments, the at least one vessel port is formed at the cap of the vessel.

In some embodiments, an interior surface of the side wall includes a first interior surface segment, a second interior surface segment, and a third interior surface segment between the first and second interior surface segments. In some such embodiments, the second interior surface segment is parallel or substantially parallel to the first interior surface segment. Each of the first and second interior surface segments is planar or substantially planar, and the third interior surface segment is curved in accordance with the vessel.

In some embodiments, an exterior surface of the side wall includes a first exterior surface segment, a second exterior surface segment, and a third exterior surface segment between the first and second exterior surface segments. In some such embodiments, the second exterior surface segment is parallel or substantially parallel to the first exterior surface segment. Each of the first, second, and third exterior surface segments is planar or substantially planar, and the third exterior surface segment is perpendicular or substantially perpendicular to the first and second exterior surface segments.

In some embodiments, the at least one connection unit includes a plurality of connection units.

In some embodiments, the upper wall of the cartridge body includes a first upper wall segment and a second upper wall segment, where the first and second upper wall segments are at different heights. In some such embodiments, at least one retainer in the corresponding retainers of the plurality of connection units is fixed on or integrally formed with each of the first and second upper wall segments.

In an exemplary embodiment, more than one retainer in the corresponding retainers of the plurality of connection units are fixed on or integrally formed with the first or second upper wall segment.

In some embodiments, the corresponding port body is movable translationally relative to the corresponding retainer in a plane perpendicular or substantially perpendicular to an axial direction of the corresponding port body.

In some embodiments, for each respective connection unit in the at least one connection unit, the corresponding port body includes a base, a stem extending from the base, and one or more first anti-rotation members disposed at the base. The corresponding retainer includes a first retaining member and a second retaining member coupled or formed with the first retaining member. The first retaining member has a first surface, and the second retaining member has a second surface spaced apart from the first surface of the first retaining member in an axial direction of the corresponding port body, where the base of the corresponding port body is disposed between the first surface of the first retaining member and the second surface of the second retaining member. The corresponding retainer also includes a first circular or substantially circular through-hole disposed on the first retaining member, The first circular or substantially circular through-hole has a diameter larger or substantially larger than an outer diameter of the stem to allow the stem of the corresponding port body to pass through and to move relative to the first retaining member. The corresponding retainer further includes one or more second anti-rotation members disposed at the first retaining member or the second retaining member and coupled with the one or more first anti-rotation members to restrict the corresponding port body from rotating relative to the retainer.

In some embodiments, the second retaining member of the corresponding retainer of each respective connection unit in the at least one connection unit is a portion of the upper wall of the cartridge body.

In an exemplary embodiment, the adapter is coupled to the upper wall of the cartridge body and the cap of the vessel.

In some embodiments, the adapter includes at least one slot for accommodating the at least on vessel port, the corresponding tube of each respective connection unit in at least one connection unit, or any combination thereof.

In some embodiments, the adapter includes (i) an internal flange for inserting into a gap between the cap and a body of the vessel, and (ii) a plurality of internal ribs for abutting a side wall of the cap, thereby restricting the cap of the vessel from moving relative to the cartridge body.

In some embodiments, the corresponding retainer restricts axial and rotational movement of the corresponding port body but allows translational movement of the corresponding port body relative to the corresponding retainer in a plane perpendicular or substantially perpendicular to an axial direction of the corresponding port body.

In some embodiments, the cartridge includes an interface member disposed at the side wall or the upper wall of the cartridge body to facilitate operation by a robotic end of arm tool (EOAT).

In an exemplary embodiment, the interface member is disposed at a middle portion of the upper wall of the cartridge body.

In some embodiments, the interface member includes a first interface surface, a second interface surface, an elongated slot, and a recess. The first interface surface is planar or substantially planar and faces away from the side wall or the upper wall of the cartridge body. The second interface surface faces toward the side wall or the upper wall of the cartridge body. The elongated slot is formed through the first interface surface to allow an elongated cam bar of the EOAT to insert into the interface member. The recess is recessed from the second interface surface toward the first interface surface and has a dimension larger than a width of the elongated slot and a length of the elongated cam bar, thereby allowing the elongated cam bar of the EOAT to rotate and engage with the interface member.

In an exemplary embodiment, the recess is a circular blind hole formed through the second interface surface and aligned with the elongated slot.

In some embodiments, the recess has a bottom surface within the interface member that is curved or slanted relative to the first interface surface.

In some embodiments, the cartridge includes a plurality of first alignment elements to facilitate alignment of the interface member with the EOAT.

In an exemplary embodiment, a first alignment element in the plurality of first alignment elements is a pin or a pin hole.

In some embodiments, the cartridge includes a plurality of second alignment elements formed at a lower portion of the side wall of the cartridge body to facilitate alignment and positioning of the cartridge on a dock.

In an exemplary embodiment, a second alignment element in the plurality of second alignment elements is a pin or a pin hole.

In some embodiments, the cartridge includes a plurality of locking elements disposed at a lower portion of the side wall of the cartridge body to facilitate positioning and locking of the cartridge on a dock In an exemplary embodiment, a locking element in the plurality of locking elements is an electromagnet or an electromagnet target.

In various embodiments, the present disclosure provides a cartridge for facilitating automation of a vessel having a cap and at least one vessel port. The cartridge includes a cartridge body, an adapter, at least one connection unit, and an interface member. The cartridge body includes an interior space to receiving at least a portion of the vessel. The adapter is disposed in the interior space and connected to or formed with the cartridge body, wherein the adapter is configured for connecting the vessel to the cartridge body. Each respective connection unit in at least one connection unit includes a corresponding connector, where the corresponding connector has a corresponding first end accessible from outside of the cartridge body and a corresponding second end for coupling with a vessel port in the at least one vessel port. The interface member is disposed on the cartridge body to facilitate operation by a robotic end of arm tool (EOAT). The interface member includes a first interface surface, a second interface surface, an elongated slot, and a recess. The first interface surface is planar or substantially planar and faces away from the cartridge body. The second interface surface faces toward the cartridge body. The elongated slot is formed through the first interface surface to allow an elongated cam bar of the EOAT to insert into the interface member. The recess is recessed from the second interface surface toward the first interface surface and has a dimension larger than a width of the elongated slot and a length of the elongated cam bar, thereby allowing the elongated cam bar of the EOAT to rotate and engage with the interface member.

In various embodiments, the present disclosure provides a cartridge for facilitating automation of a vessel having a cap and a plurality of vessel ports. The cartridge includes a cartridge body, an adapter, and a plurality of connection units. The cartridge body includes an upper wall having a plurality of regions. The adapter is connected to or formed with the cartridge body, and configured for removably connecting the vessel to the cartridge body. Each respective connection unit in the plurality of connection unit includes a corresponding port body, a corresponding retainer, a corresponding connector, and a corresponding tube. The corresponding port body includes a base, a stem extending from the base, and one or more first anti-rotation members disposed at the base. The corresponding retainer includes a first retaining member, a second retaining member, a first circular or substantially circular through-hole, and one or more second anti-rotation members. The second retaining member is a corresponding region in the plurality of regions of the upper wall of the cartridge body. The first retaining member has a first surface and the second retaining member has a second surface spaced apart from the first surface of the first retaining member in an axial direction of the corresponding port body, with the base of the corresponding port body disposed between the first surface of the first retaining member and the second surface of the second retaining member. The first circular or substantially circular through-hole is disposed on the first retaining member and has a diameter larger or substantially larger than an outer diameter of the stem to allow the stem of the corresponding port body to pass through and to move relative to the first retaining member. The one or more second anti-rotation members are disposed at the first retaining member or the second retaining member and coupled with the one or more first anti-rotation members to restrict the corresponding port body from rotating relative to the retainer. The corresponding connector is housed by the corresponding port body and has a corresponding first end and a corresponding second end, where the corresponding first end is positioned outside of the cartridge body. The corresponding tube is configured for connecting the corresponding second end of the corresponding connector to a vessel port in the plurality of vessel ports.

In some embodiments, the upper wall of the cartridge body includes a first upper wall segment and a second upper wall segment, where the first and second upper wall segments are at different heights. In some such embodiments, each of the first and second upper wall segments includes at least one region in the plurality of regions to serve as the second retaining member of at least one retainer.

In some embodiments, each of the first and second upper wall segments includes two or more regions in the plurality of regions to serve as the second retaining members of two or more retainers.

The methods and apparatuses of the present disclosure have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 5E is a cross-sectional view taken along line 5E-5E of FIG. 5D.

FIG. 5F is a cross-sectional view taken along line 5F-5F of FIG. 5D.

FIG. 5G is a cross-sectional view taken along line 5G-5G of FIG. 5D.

Figure 1A:
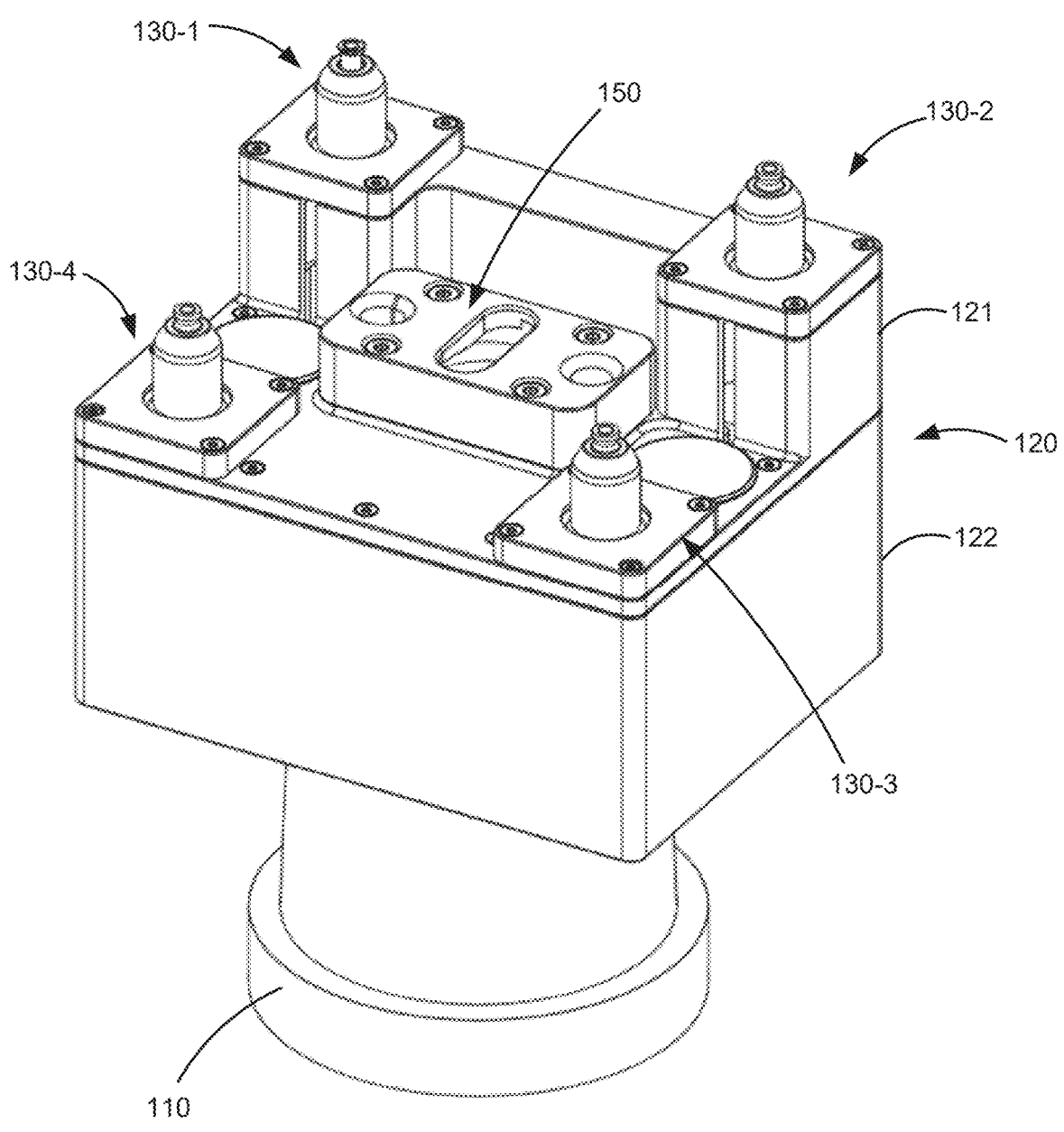
FIG. 1A is a perspective view illustrating an exemplary apparatus, where an exemplary device is connected to the exemplary apparatus, in accordance with some exemplary embodiments of the present disclosure.
Figure 1B:
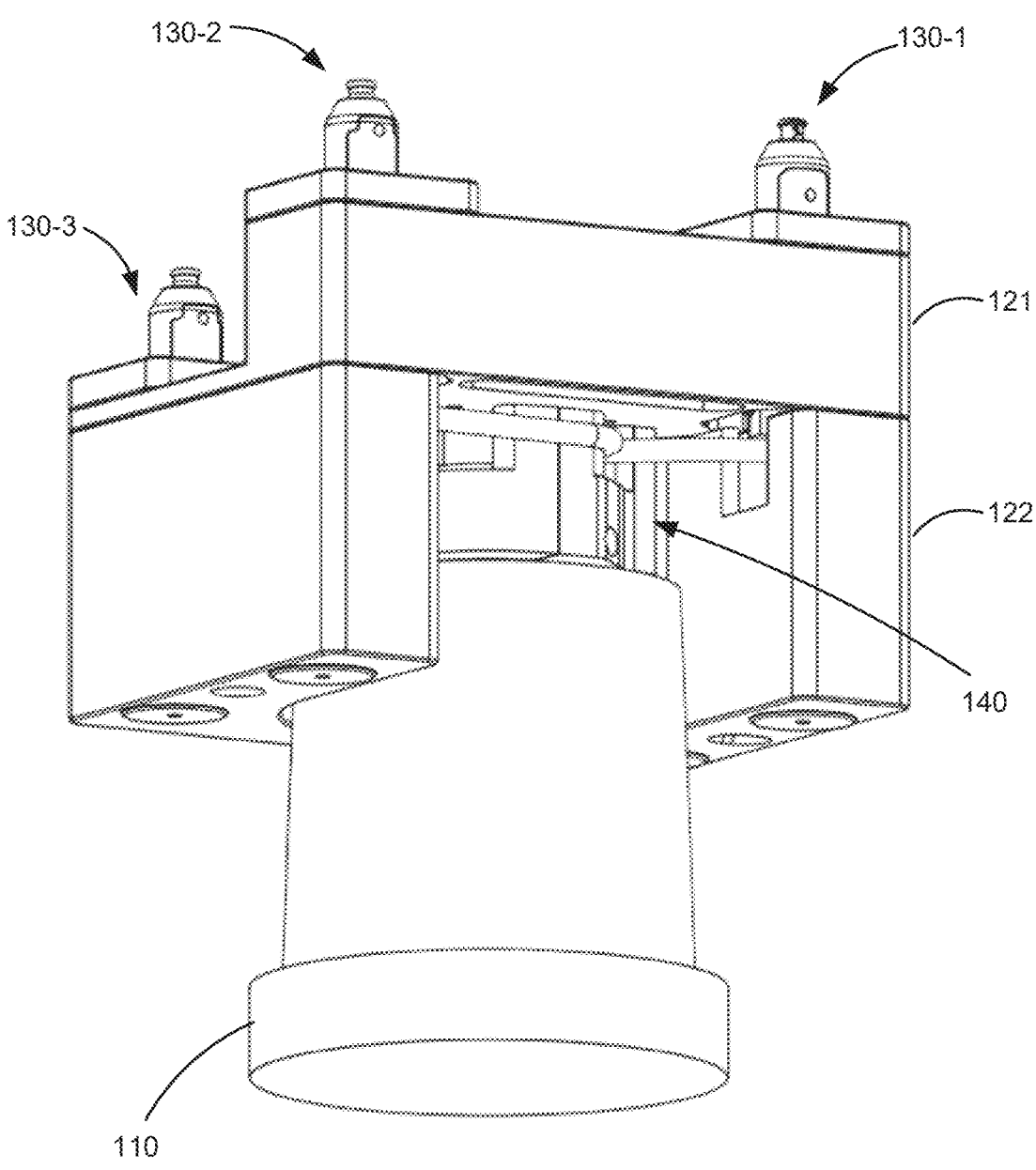
FIG. 1B is another perspective view illustrating the exemplary apparatus of FIG. 1A in accordance with some exemplary embodiments of the present disclosure.
Figure 1C:
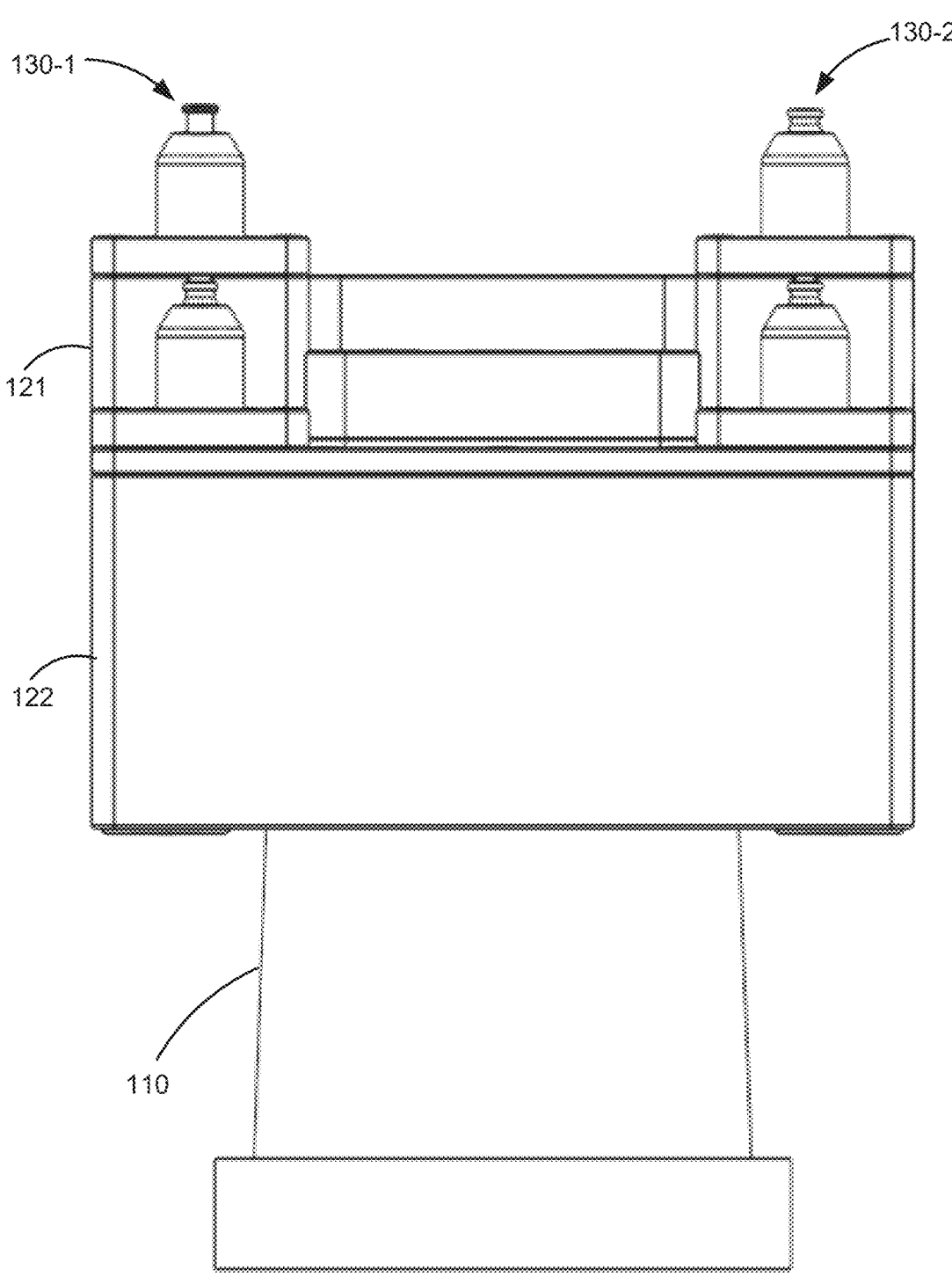
FIG. 1C is a front side view illustrating the exemplary apparatus of FIG. 1A in accordance with some exemplary embodiments of the present disclosure.
Figure 1D:
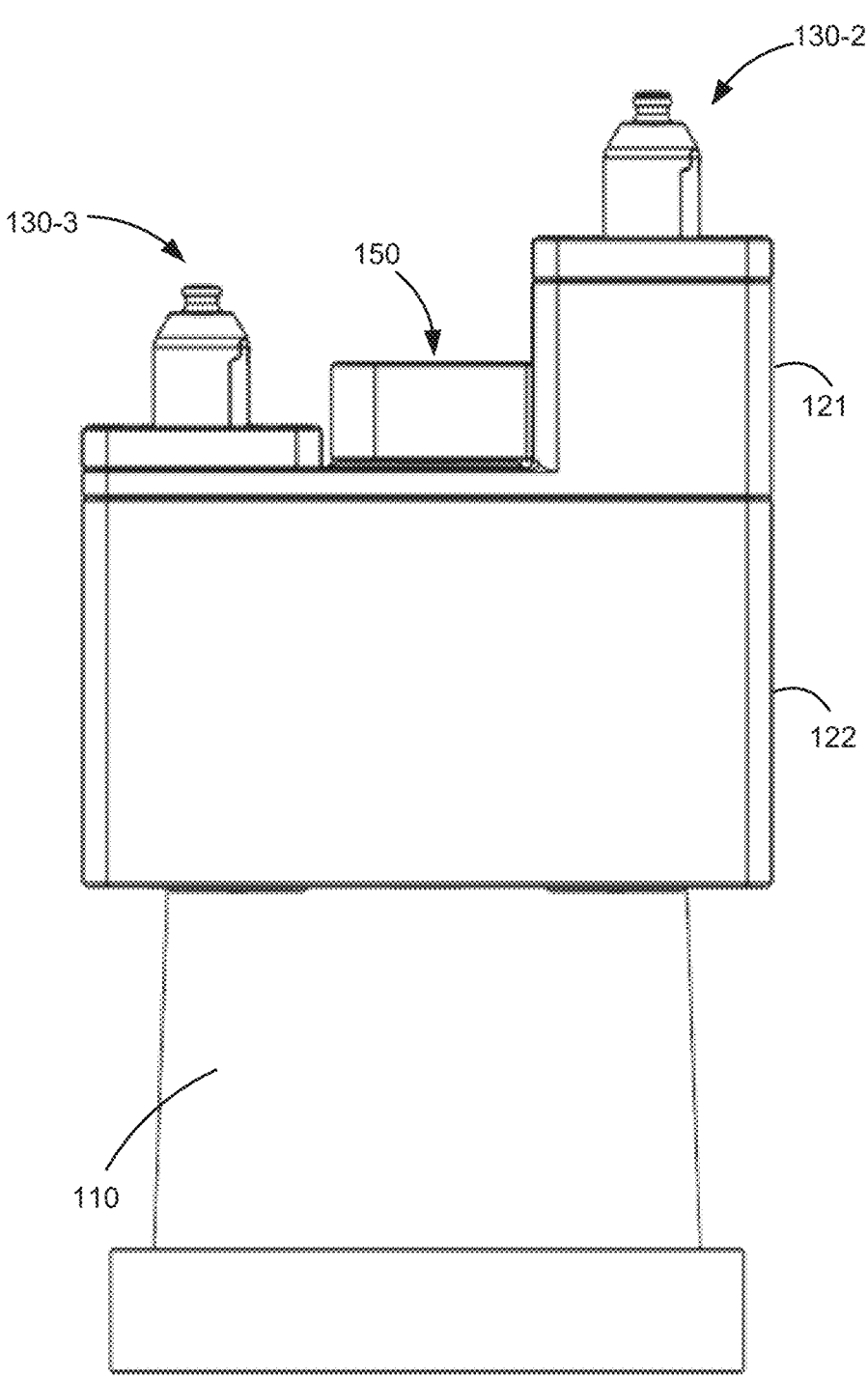
FIG. 1D is a right side view illustrating the exemplary apparatus of FIG. 1A in accordance with some exemplary embodiments of the present disclosure.
Figure 1E:
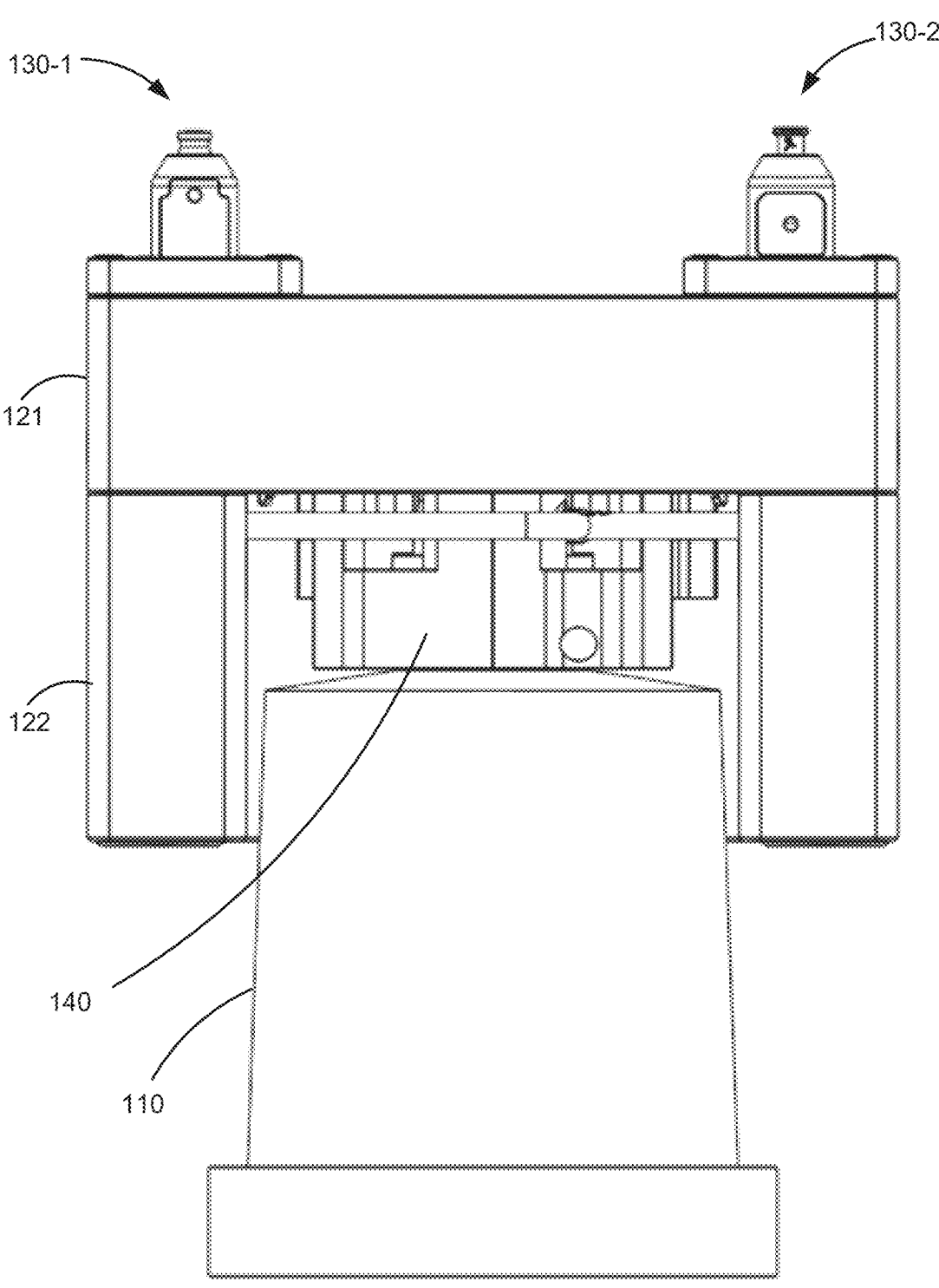
FIG. 1E is a rear side view illustrating the exemplary apparatus of FIG. 1A in accordance with some exemplary embodiments of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present disclosure provides apparatuses that can facilitate automation of vessels such as bioreactor devices. An apparatus generally includes a cartridge body, an adapter for removably connecting a vessel to the cartridge body, and at least one connection unit disposed at the cartridge body for fluidic communication with the vessel. In various embodiments, the apparatus includes a novel design that takes an industry standard vessel (e.g., a bioreactor) and adapts it to a robot compatible compact cartridge with gripping features, floating ports, concealed tubing, docking features, and/or other features. As such, the apparatuses of the present disclosure advantageously leverage advanced robotic features and technologies while retaining the benefits of conventional closed-system processes (e.g., providing a sterile clean room environment). This enables the transformation of cellular engineering target manufacturing from labor-based and low-throughput processes to fully industrialized, high-throughput processes with high scale, efficiency and repeatability.

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first instrument could be termed a second instrument, and, similarly, a second instrument could be termed a first instrument, without departing from the scope of the present disclosure. The first instrument and the second instrument are both instruments, but they are not the same instrument.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Furthermore, when a reference number is given an "$i^{th}$" denotation, the reference number refers to a generic component, set, or embodiment. For instance, an application termed "application i" refers to the $i^{th}$ application in a plurality of applications.

The term "about" or "approximately" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

For purposes of explanation, the description herein has been described with reference to specific implementations. However, the illustrative discussions are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case-and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Referring to FIGS. 1A-1L, there is depicted an exemplary apparatus, generally designated 100, in accordance with some exemplary embodiments of the present disclosure. The apparatus 100 (also referred herein as a cartridge) is configured to facilitate automation of a device, e.g., converting a non-robotic operable device (e.g., a vessel) to an automation compatible device. In various embodiments, the apparatus 100 includes a novel design that converts a standard vessel to a robot compatible cartridge. One of the key innovations is taking an industry standard vessel (e.g., a bioreactor) and adapting it to a robot compatible compact cartridge with gripping features, floating ports, concealed tubing, docking features, and/or other features.

In some embodiments, the vessel is a bioreactor device, such as a bioreactor device 110. In some embodiments, the bioreactor device is configured for producing immune cells such as T cells, natural killer cells, and hematopoietic cells. A non-limiting example of such a bioreactor device is a gas permeable rapid expansion bioreactor device. In some embodiments, the bioreactor device 110 includes a cap, such as a cap 111, and at least one bioreactor ports (e.g., 1, 2, 3, 4, 5, or more than 5 ports), such as bioreactor ports 112. In some embodiments, the at least one bioreactor ports are disposed at the cap (e.g., formed with the cap). As a non-limiting example, four bioreactor ports are illustrated and disposed at the cap.

The apparatus 100 generally includes a cartridge body, at least one connection unit disposed at the cartridge body, and an adaptor connected to or formed with the cartridge body and configured for removably connecting the bioreactor device to the cartridge body. For instance, in some embodiments, the apparatus 100 includes a cartridge body 120, at least one connection unit 130 disposed at the cartridge body 120, and an adaptor 140 connected to or formed with the cartridge body 120 and configured for removably connecting the bioreactor device 110 to the cartridge body 120. In some embodiments, the apparatus 100 includes additional, optional, or alternative components. For instance, in some embodiments, the apparatus 100 includes (i) an interface member, such as an interface member 150, to facilitate operation by a robotic end of arm tool (EOAT), (ii) one or more alignment elements, such as alignment elements 170, to facilitate alignment and positioning of the cartridge on a dock, (iii) one or more locking elements, such as locking members 180, to facilitate positioning and locking of the cartridge on a dock, (iv) or any combination thereof.

In some embodiments, the cartridge body includes a side wall, an upper wall connected to or formed with an upper portion of the side wall, and an interior defined by the side wall and the upper wall. For instance, in some embodiments, the cartridge body 120 includes an upper wall 121, a side wall 122, and an interior 123. The upper wall 121 is connected to or formed with an upper portion of the side wall 122. The upper wall 121 and the side wall 122 collectively define the interior 123.

In some embodiments, each respective connection unit in the at least one connection unit includes a floating non-rotating structure that is compatible with a variety of fluid and non-fluid connectors and incorporates an external lead-in feature for the mating coupler. In some embodiments, one of the key innovations is the combination of the port body shape which has a tip (e.g., a large chamfered tip) to engage with a mating coupler and corresponding size multi-directional planar float of the port body that accommodates axial misalignment but resists torsional loads typically associated with a threaded connector. In some embodiments, the port body is designed to house effectively converting an array of industry standard connectors into robotic compatible connectors due to the external mating feature and position tolerance compensation via the floating structure (e.g., movable) of the port body. In some embodiments, each respective connection unit in the at least one connection unit is configured for accommodating axial misalignment during mating with a device or a component of a device.

For instance, in some embodiments, each respective connection unit in the at least one connection unit includes a corresponding retainer, a corresponding port body, a corresponding connector, and a corresponding tube. In some embodiments, the corresponding retainer is fixed on or integrally formed with the upper wall of the cartridge body (e.g., one or more components of the corresponding retainer are a portion of the upper wall). In some embodiments, the corresponding port body is coupled to the corresponding retainer and has a corresponding distal end portion positioned exterior to the cartridge body. In some embodiments, the corresponding connector is housed by the corresponding port body and has a correspond first end and a corresponding second end. In some embodiments, the corresponding first end of the corresponding connector is positioned outside of the cartridge body so that it can be connected to other device. In some embodiments, the corresponding tube is configured for connecting (e.g., fluidly connecting) the corresponding second end of the corresponding connector to a bioreactor port in the at least one bioreactor port of the bioreactor device. In some embodiments, the corresponding retainer is configured to restrict the corresponding port body from rotating relative to the corresponding retainer but allow the corresponding port body to move translationally relative to the corresponding retainer in a plane perpendicular or substantially perpendicular to an axial direction of the corresponding port body. Accordingly, the corresponding retainer restricts the corresponding connector, which is held by the corresponding port body, from rotating relative to the corresponding retainer but allows the corresponding connector to move translationally relative to the corresponding retainer in the plane perpendicular or substantially perpendicular to the axial direction of the corresponding port body. Advantageously, this can accommodate axial misalignment when connecting the corresponding connector with a device while constraining rotation.

As a non-limiting example, four connection units, e.g., connection units 130-1, 130-2, 130-3, 130-4, are illustrated. In some embodiments, the connection unit 130-1 includes a retainer 131-1, a port body 132-1, a connector 133-1, and a tube 134-1. The retainer 131-1 is fixed on the upper wall of the cartridge body or has one or more components integrally formed with the upper wall of the cartridge body. The port body 132-1 is coupled to the retainer 131-1 and has a distal end portion positioned exterior to the cartridge body as shown in the figures. The connector 133-1 is housed by the port body 132-1 and connected to a first bioreactor port of the bioreactor device by the tube 134-1. For instance, in some embodiments, the connector 133-1 has a first end and a second end, with the first end positioned outside of the port body and the cartridge body and the second end positioned inside of the port body or the cartridge body. The tube 134-1 connects the second end with a first bioreactor port of the bioreactor device.

Similarly, the connection unit 130-2 includes a retainer 131-2, a port body 132-2, a connector 133-2, and a tube 134-2. The connection unit 130-2 includes a retainer 131-2, a port body 132-2, a connector 133-2, and a tube 134-2. The retainer 131-2 is fixed on the upper wall of the cartridge body or has one or more components integrally formed with the upper wall of the cartridge body. The port body 132-2 is coupled to the retainer 131-2 and has a distal end portion positioned exterior to the cartridge body as shown in the figures. The connector 133-2 is housed by the port body 132-2 and connected to a second bioreactor port of the bioreactor device by the tube 134-2, e.g., the tube 134-2 connecting a second end of the connector 133-2 with a second bioreactor port of the bioreactor device.

The connection unit 130-3 includes a retainer 131-3, a port body 132-3, a connector 133-3, and a tube 134-3. The connection unit 130-3 includes a retainer 131-3, a port body 132-3, a connector 133-3, and a tube 134-3. The retainer 131-3 is fixed on the upper wall of the cartridge body or has one or more components integrally formed with the upper wall of the cartridge body. The port body 132-3 is coupled to the retainer 131-3 and has a distal end portion positioned exterior to the cartridge body as shown in the figures. The connector 133-3 is housed by the port body 132-3 and connected to a second bioreactor port of the bioreactor device by the tube 134-3, e.g., the tube 134-3 connecting a second end of the connector 133-3 with a third bioreactor port of the bioreactor device.

The connection unit 130-4 includes a retainer 131-4, a port body 132-4, a connector 133-4, and a tube 134-4. The connection unit 130-4 includes a retainer 131-4, a port body 132-4, a connector 133-4, and a tube 134-4. The retainer 131-4 is fixed on the upper wall of the cartridge body or has one or more components integrally formed with the upper wall of the cartridge body. The port body 132-4 is coupled to the retainer 131-4 and has a distal end portion positioned exterior to the cartridge body as shown in the figures. The connector 133-4 is housed by the port body 132-4 and connected to a second bioreactor port of the bioreactor device by the tube 134-4, e.g., the tube 134-4 connecting a second end of the connector 133-4 with a fourth bioreactor port of the bioreactor device.

In some embodiments, at least one connector is a gas connector. In some embodiments, at least one connector is a fluid connector. In some such embodiments, the fluid connector includes a needle-free valve, a female luer, a barb connector, or any combination thereof.

Figure 1F:
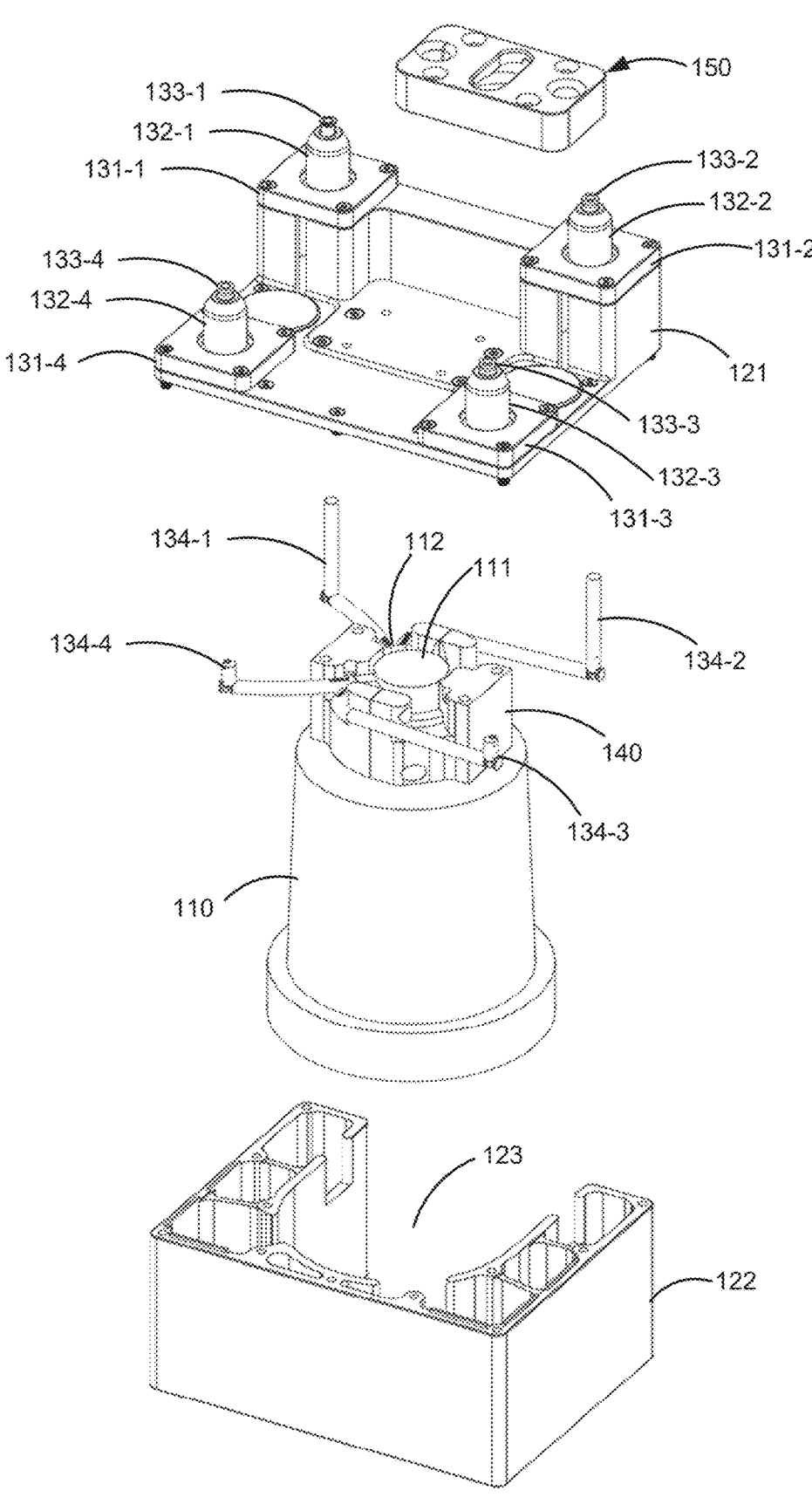
FIG. 1F is a partially exploded view illustrating the exemplary apparatus of FIG. 1A in accordance with some exemplary embodiments of the present disclosure.
Figure 1G:
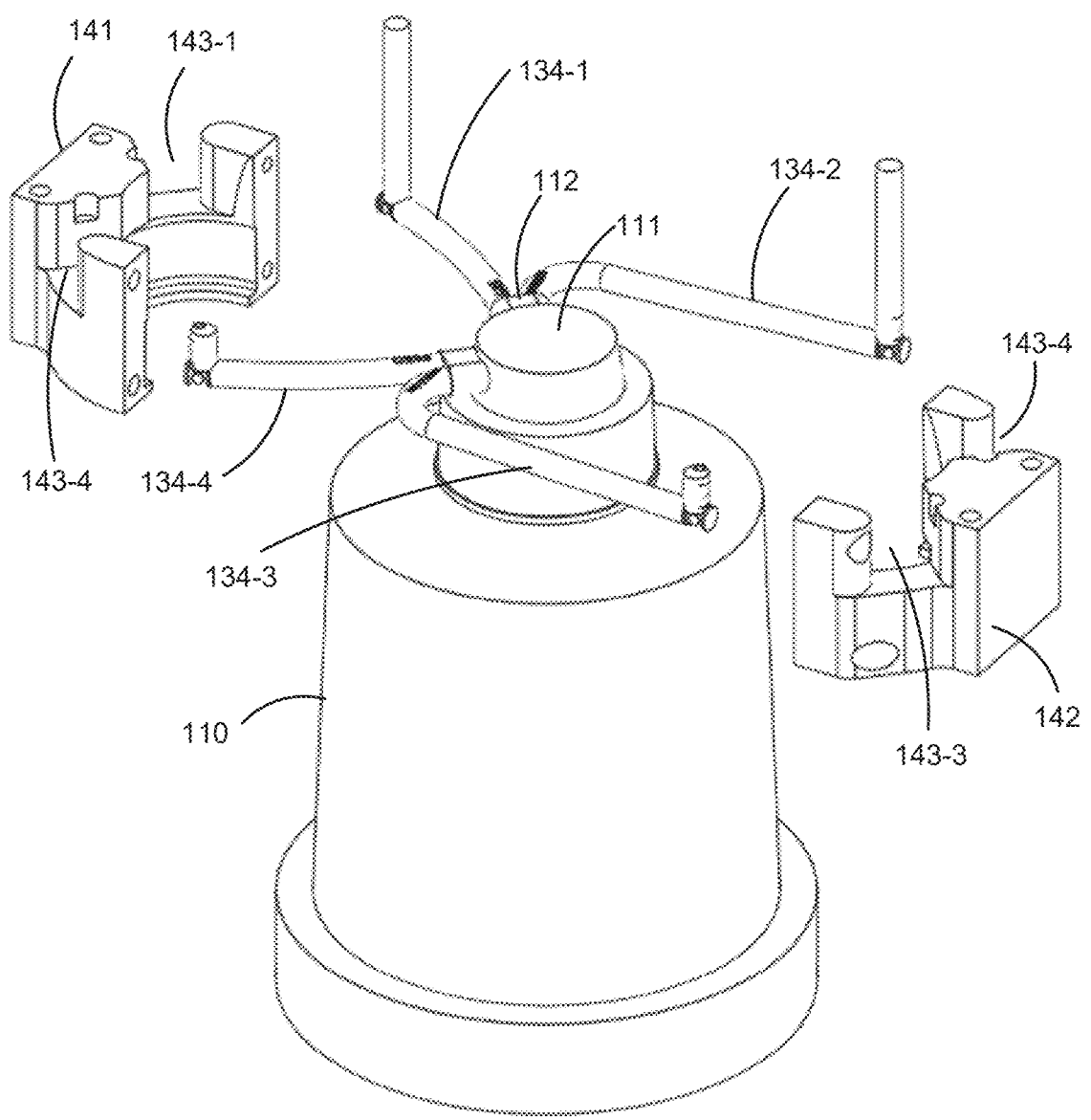
FIG. 1G is a partially exploded view illustrating some components of the exemplary apparatus of FIG. 1A in accordance with some exemplary embodiments of the present disclosure.
Figure 1H:
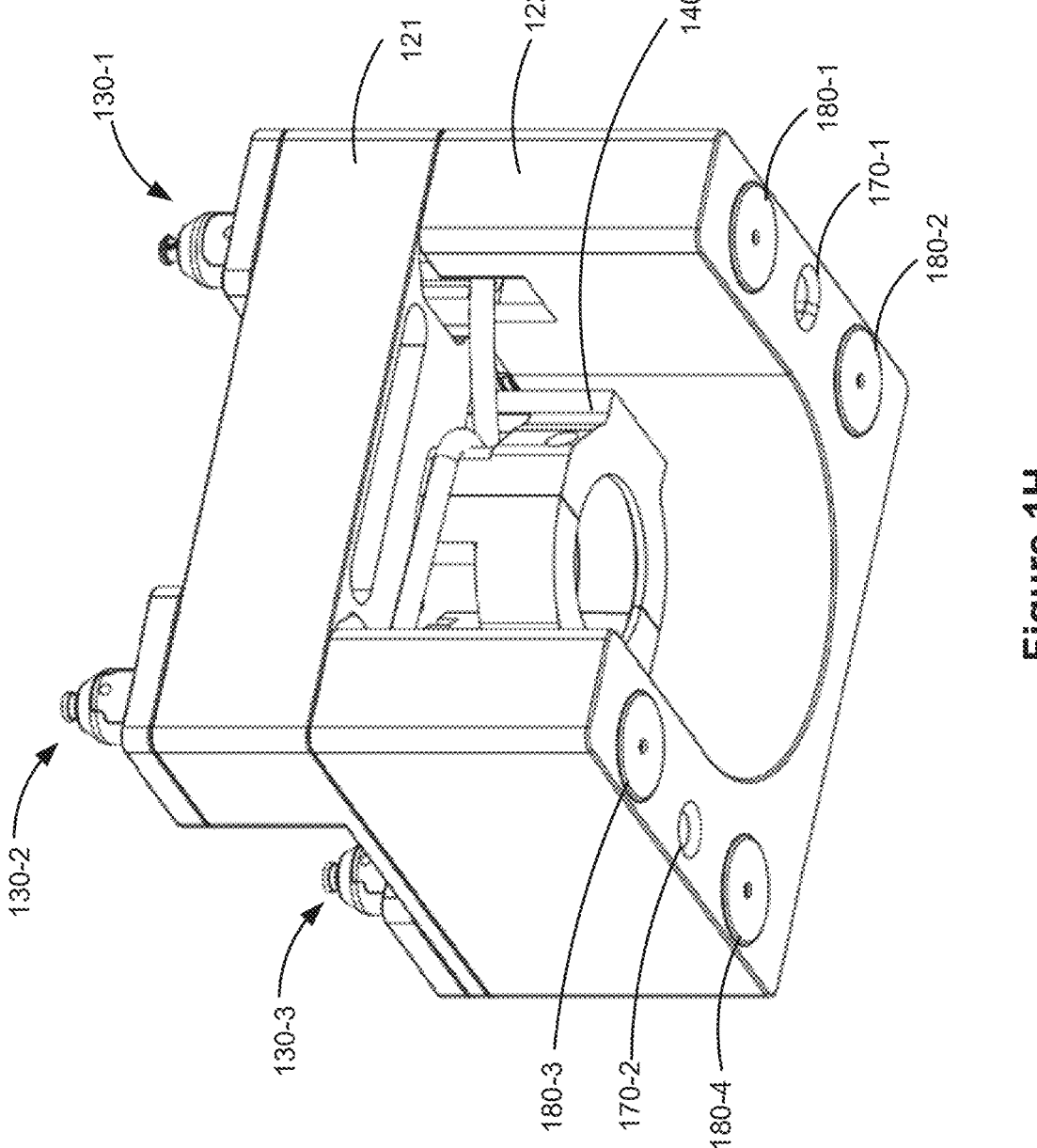
FIG. 1H is a perspective view illustrating the exemplary apparatus of FIG. 1A, where the exemplary device is removed, in accordance with some exemplary embodiments of the present disclosure.
Figure 1I:
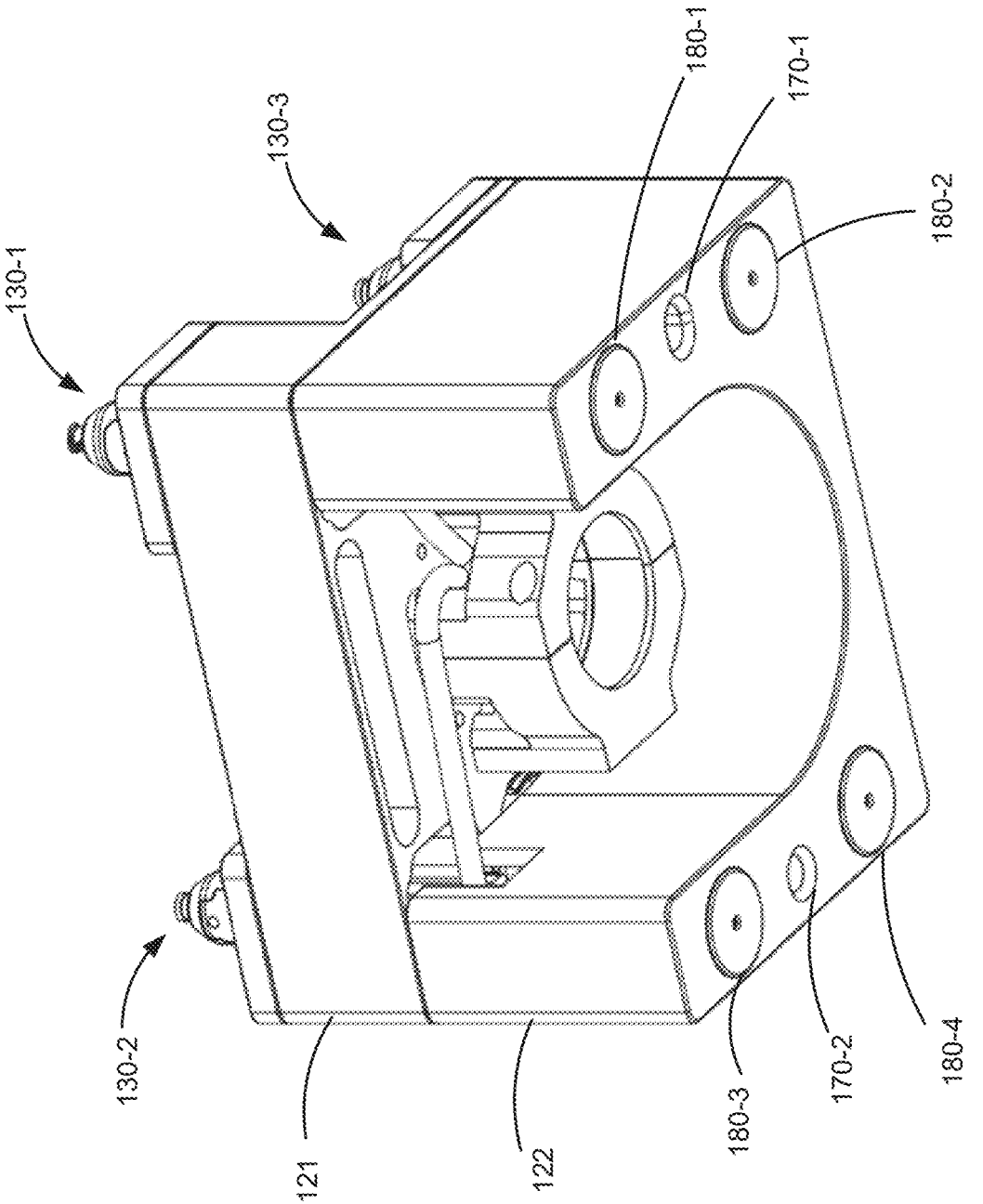
FIG. 1I is another perspective view illustrating the exemplary apparatus of FIG. 1H in accordance with some exemplary embodiments of the present disclosure.

Referring in particular to FIGS. 1F and 1G, in some embodiments, the adapter 140 is a split adapter such that some or all of the adapter can be open and closed to selectively engage and disengage with the device 110. For instance, in some embodiments, the adapter 140 includes a first adapter member 141 and a second adapter member 142 that are removably coupled to each other. In some embodiments, the adapter includes one or more slots to accommodate the tube(s) of the one or more connection units. For instance, as a non-limiting examples, the adapter is illustrated to have four slots, e.g., a slot 143-1 to accommodate the tube 134-1, a slot 143-2 to accommodate the tube 134-2, a slot 143-3 to accommodate the tube 134-3, and a slot 143-4 to accommodate the tube 134-4. In some embodiments, each of the first and second adapter members includes an inter flange segment, such as an inner flange segment 144 to be disposed under the cap of the device, thereby holding the device uprightly.

Figure 1J:
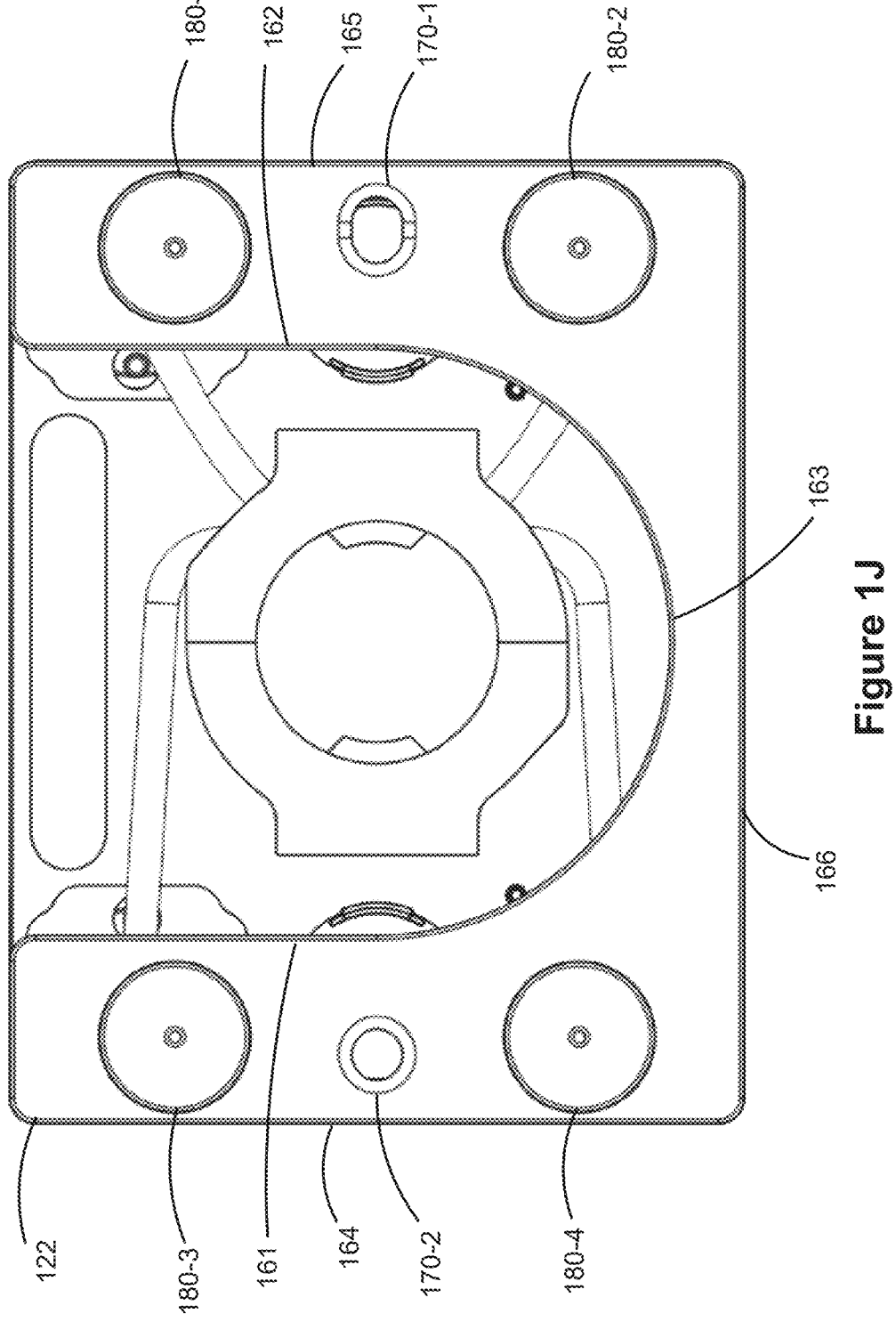
FIG. 1J is a bottom view illustrating the exemplary apparatus of FIG. 1H in accordance with some exemplary embodiments of the present disclosure.
Figure 1K:
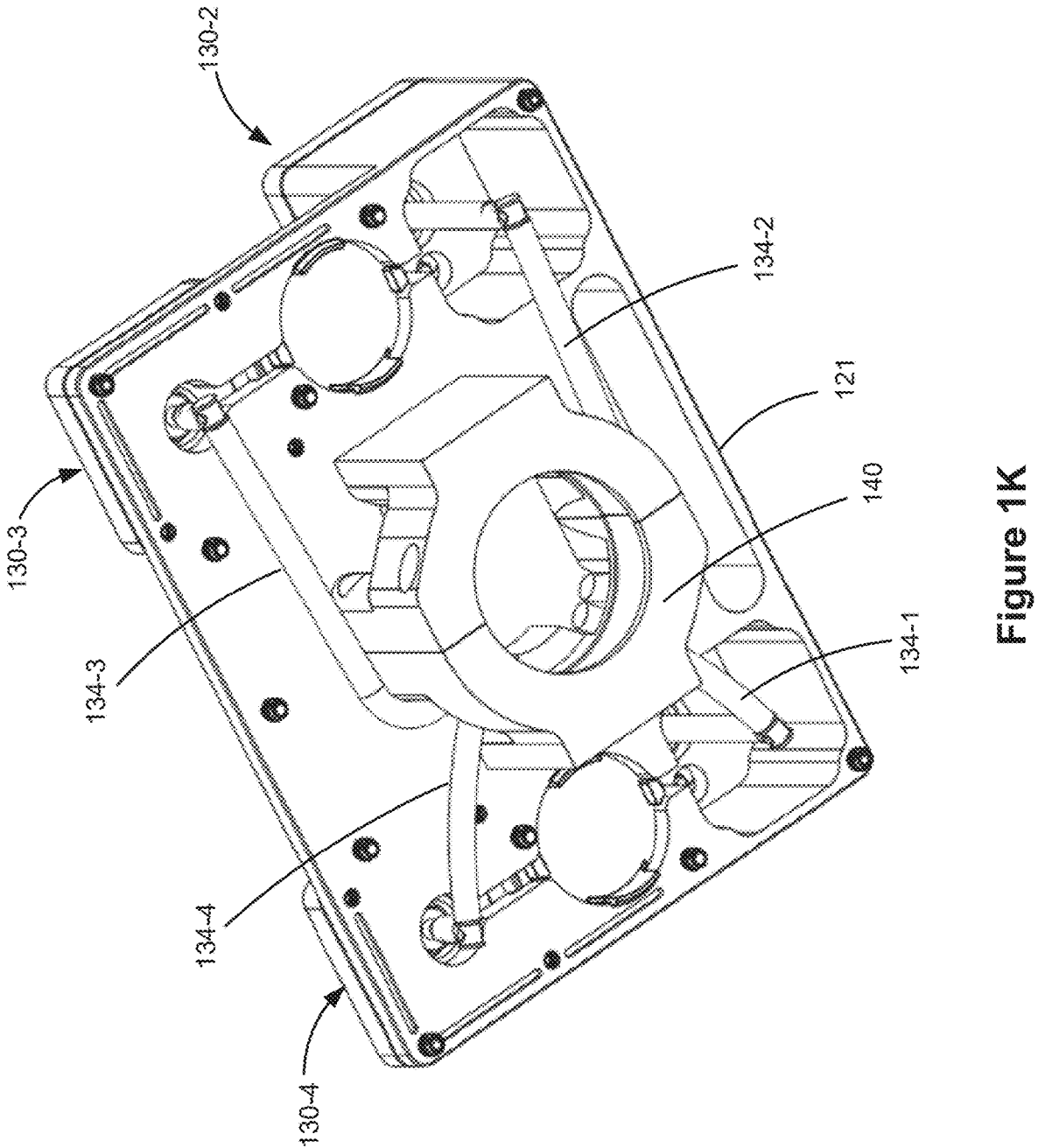
FIG. 1K is a perspective view illustrating the exemplary apparatus of FIG. 1H, where some components are removed to show interior components of the exemplary apparatus, in accordance with some exemplary embodiments of the present disclosure.
Figure 1L:
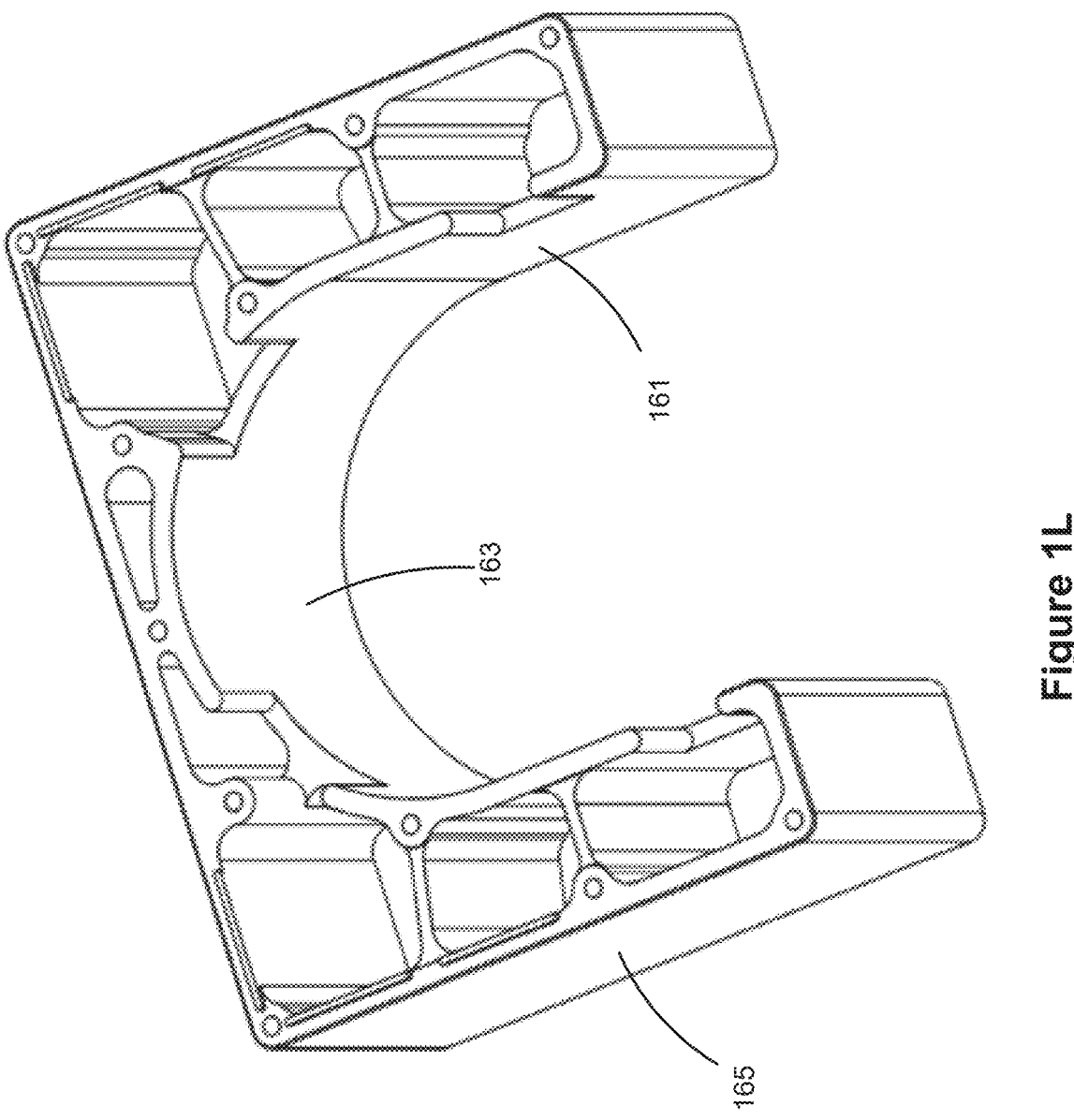
FIG. 1L is a perspective view illustrating a component of the exemplary apparatus of FIG. 1H in accordance with some exemplary embodiments of the present disclosure.

Referring in particular to FIGS. 1J and 1L, in some embodiments, the side wall 122 includes an interior surface comprised of a plurality of interior surface segments. For instance, in some embodiments, the interior surface of the side wall includes a first interior surface segment 161, a second interior surface segment 162 parallel or substantially parallel to the first interior surface segment, and a third interior surface segment 163 between the first and second interior surface segments. In an exemplary embodiment, each of the first and second interior surface segments is planar or substantially planar, and the third interior surface segment is curved in accordance with the device 110. In some embodiments, the side wall 122 includes an exterior surface comprised of a plurality of exterior surface segments. For instance, in some embodiments, the exterior surface of the side wall includes a first exterior surface segment 164, a second exterior surface segment 165 parallel or substantially parallel to the first exterior surface segment, and a third exterior surface segment 166 between the first and second exterior surface segments. In an exemplary embodiment, each of the first, second, and third exterior surface segments is planar or substantially planar, and the third exterior surface segment is perpendicular or substantially perpendicular to the first and second exterior surface segments. However, the present disclosure is not limited thereto. The side wall can be configured with other shapes and sizes. In addition, the side wall can have other features, such as slots, holes and/or ribs, to facility accommodation of tube(s), reduction of the weight/material of the side wall, enhancement of the strength of the side wall, and/or other functionalities.

Referring to FIGS. 2A-2H, there is depicted an exemplary port body with an exemplary connector (e.g., a fluid connector) housed in the exemplary port body in accordance with some exemplary embodiments of the present disclosure. In some embodiments, the port body 132 includes a base, such as a base 210. While the base is illustrated to be of a circular shape, it should be noted that this is by way of example and the present disclosure is not limited thereto. For instance, the base can have a non-circular shape, such as an oblong or oval shape. The base can also have other regular or irregular shapes. In some embodiments, the base is planar or substantially planar. The base is characterized by a first dimension (e.g., a width, a diameter) "D1" and a second dimension (e.g., a thickness) "D2."

In some embodiments, the port body 132 includes a stem, such as a stem 220, extended from the base. The stem is generally cylindrical or substantially cylindrical, with at least a portion of the stem having a circular or substantially circular cross section. The stem is characterized by a third dimension (e.g., an outer diameter) "D3" that is smaller than the first dimension "D1" of the base. In some embodiments, the stem includes two or more stem members that are removably coupled (e.g., snap-fitted, interference-fitted) with each other and configured to help secure the connector 132 (e.g., a fluid connector) at the port body. For instance, in an exemplary embodiment, the stem includes a first stem member 260 and a second stem member 270 removably coupled with each other. In some embodiments, the first stem member is monolithically formed (e.g., molded) with the base as a single piece, and the second stem member is formed as a separate piece (e.g., an insert) to removably couple with the single piece.

In some embodiments, the stem is configured to secure the connector to restrict the connector from moving relative to the stem body, e.g., from moving axially and/or rotating around its axis. For intance, in some embodiments, the stem includes a plurality of internal ribs, such as one or more ribs 261, one or more ribs 262, one or more ribs 271, or any combination thereof. The plurality of internal ribs is disposed on an inner surface 221 of the stem. Each internal rib in the plurality of internal ribs is configured for abutting an external wall 281 of the connector (e.g., having a surface that forms a contact with the external wall) to secure the connector with the port body. In some embodiments, at least some internal ribs in the plurality of internal ribs are distributed circumferentially on the inner surface of the stem.

Figures 2A, 2B:
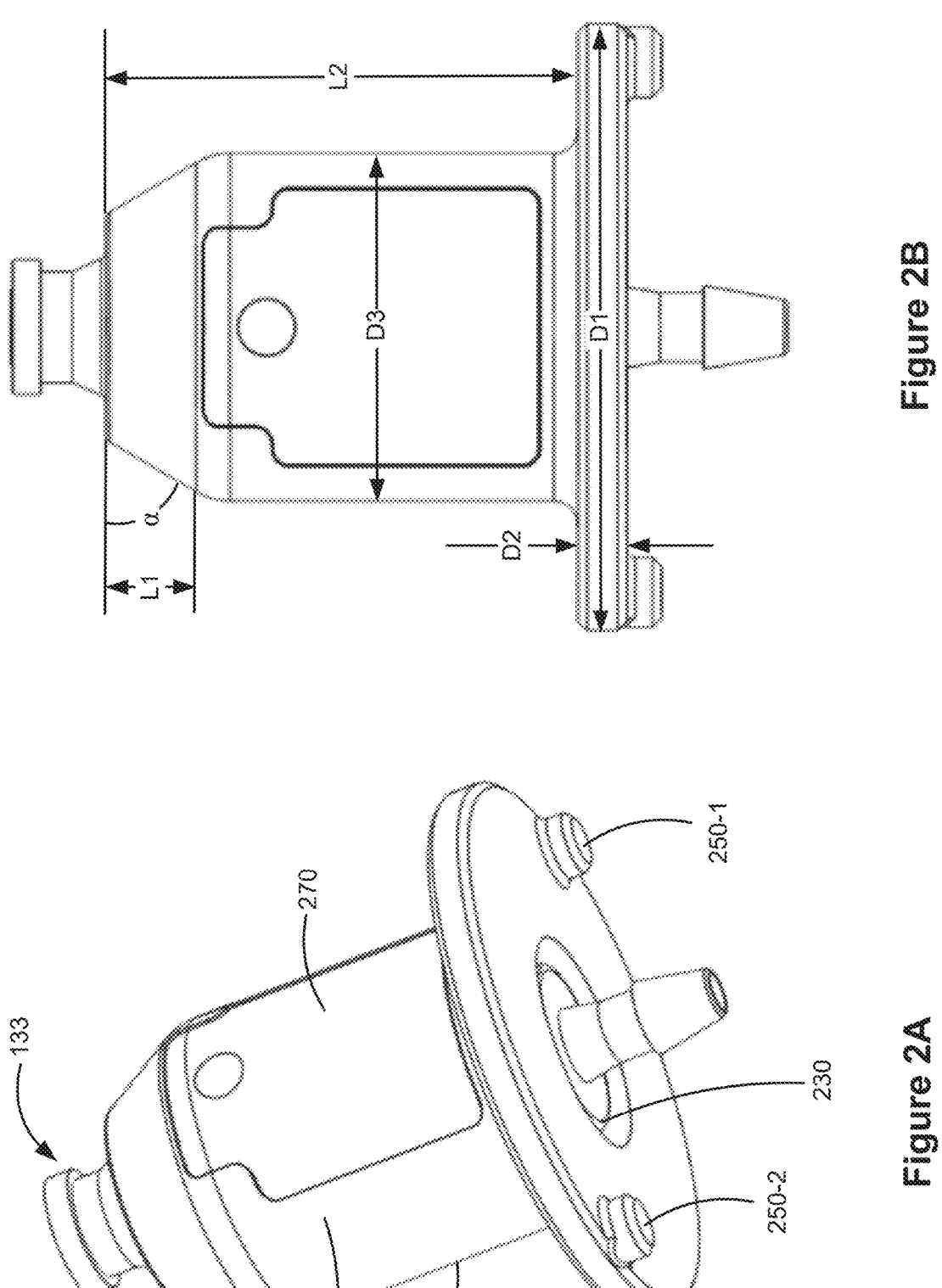
FIG. 2A is a perspective view illustrating an exemplary port body in accordance with some exemplary embodiments of the present disclosure.
FIG. 2B is a side view illustrating the exemplary port body of FIG. 2A.
Figure 2D:
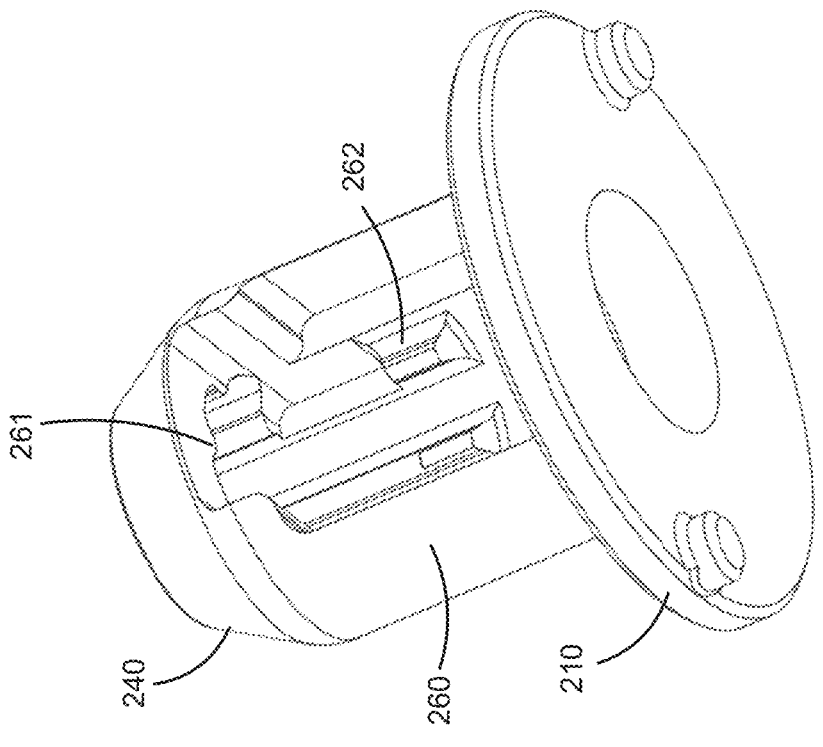
FIG. 2D is a perspective view illustrating an interior of the exemplary port body of FIG. 2A in accordance with some exemplary embodiments of the present disclosure.
Figure 2C:
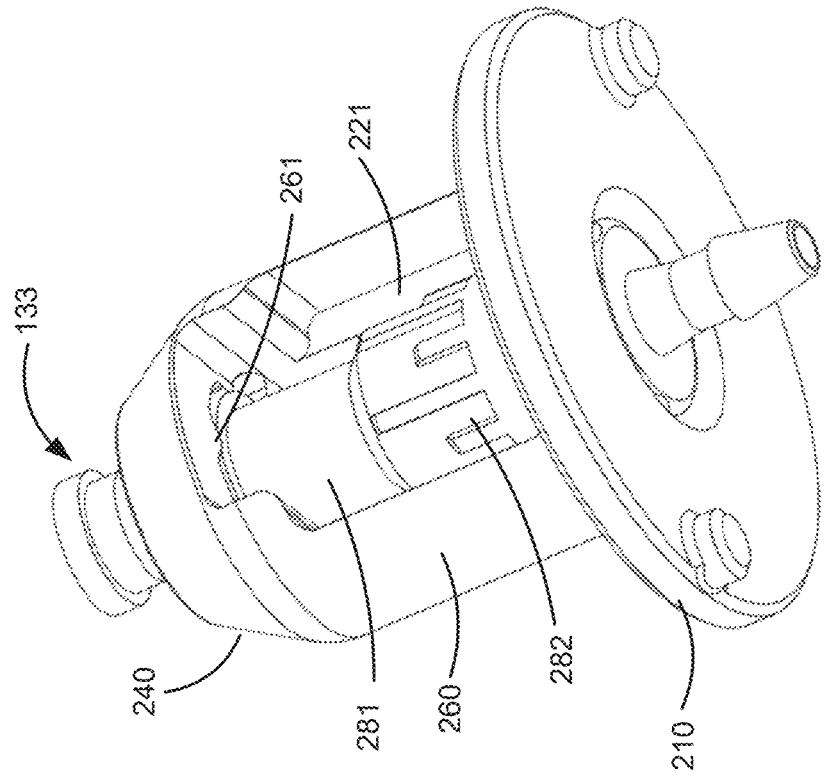
FIG. 2C is a perspective view illustrating an interior of the exemplary port body of FIG. 2A, with a connector held by exemplary port body, in accordance with some exemplary embodiments of the present disclosure.
Figure 2F:
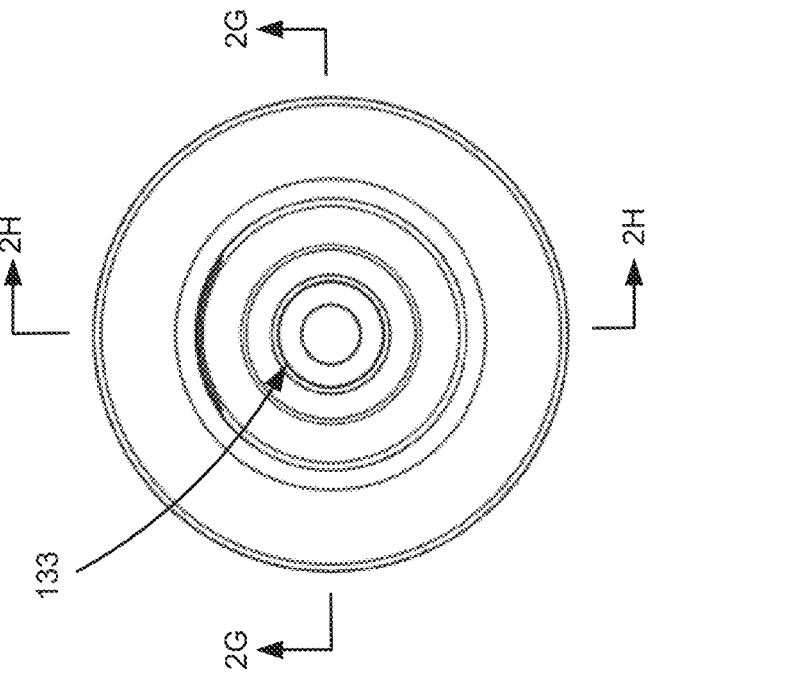
FIG. 2F is a top view illustrating the exemplary port body of FIG. 2A in accordance with some exemplary embodiments of the present disclosure
Figure 2E:
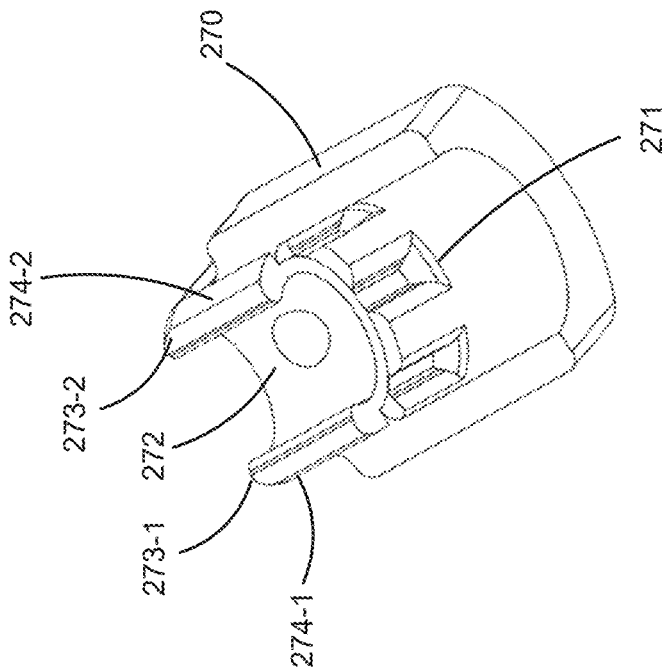
FIG. 2E is a perspective view illustrating a stem member of the exemplary port body of FIG. 2A in accordance with some exemplary embodiments of the present disclosure.

In some embodiments, each internal rib in at least a subset of the plurality of internal ribs includes a first rib portion disposed at or adjacent the free end portion of the stem and a second rib portion disposed between the free end portion of the stem and the base. For instance, as illustrated in FIG. 2D, the rib 262 includes a first rib portion disposed at or adjacent the free end portion of the stem and a second rib portion disposed between the free end portion of the stem and the base. In some embodiments, the second rib portion contacts with a knurled surface 282 of the connector. In some embodiments where the stem includes the first stem member and the second stem member, at least one internal rib in the plurality of internal ribs is formed on each of the first stem member and the second stem member. For instance, one or more ribs 261, one or more ribs 262, or any combination thereof are formed on the first stem member, and one or more ribs 271 are formed on the second stem member.

Figure 2H:
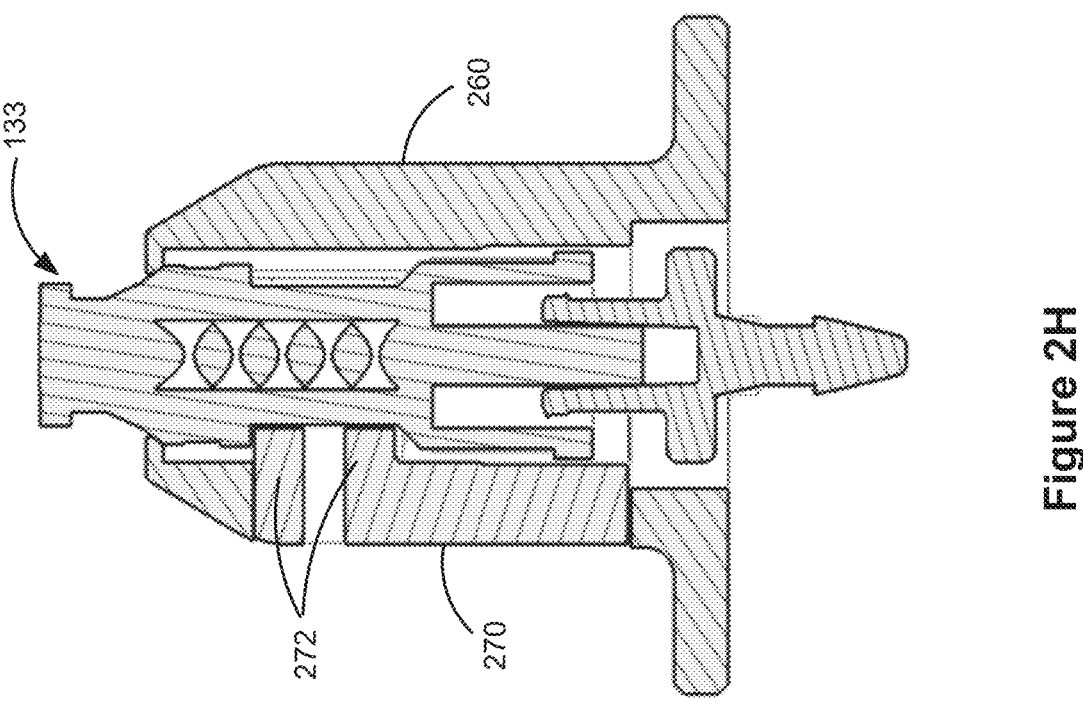
FIG. 2H is a cross-sectional view taken along line 2H-2H of FIG. 2F.
Figure 2G:
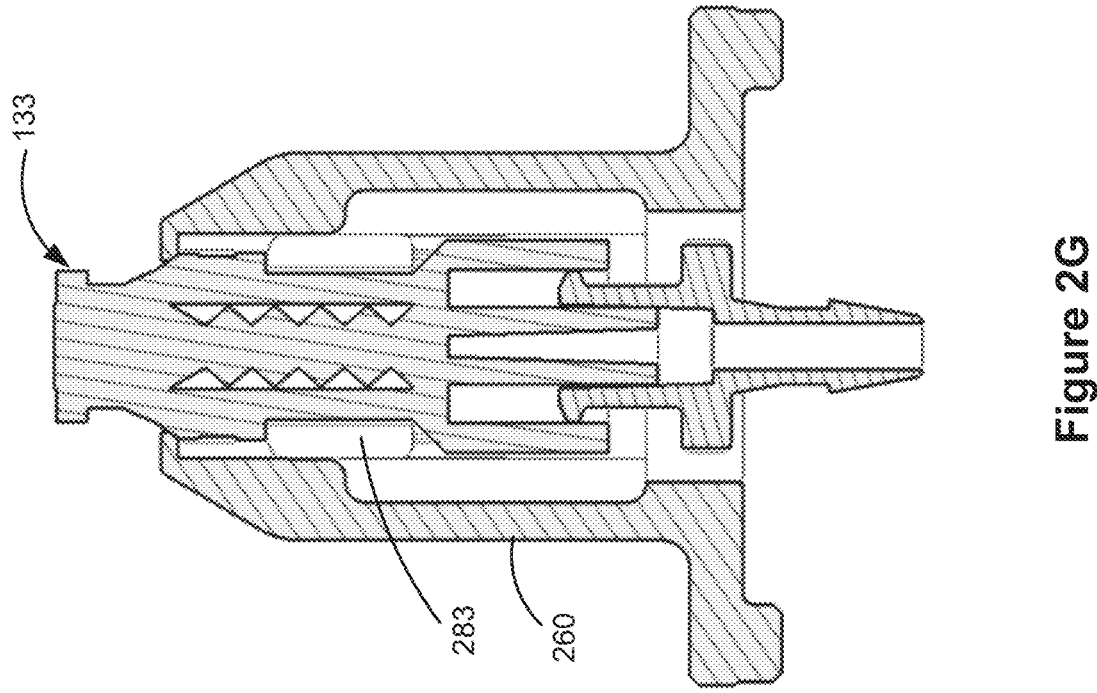
FIG. 2G is a cross-sectional view taken along line 2G-2G of FIG. 2F.

In some embodiments, the second stem member includes an upper portion 272 having a pair of arms configured to couple the second stem member with the first stem member. In some embodiments, each arm includes an engaging member (e.g., a snap-fitting joint) 274 to engage with a complementary engaging member disposed at the first stem member. In some embodiments, a segment of the upper portion 272 is inserted into a groove 283 (e.g., a neck, a recess) of the connector as illustrated in FIG. 2H, thereby helping to secure the connector on the port body and restrict the connector from moving axially relative to the port body.

In some embodiments, the port body 132 includes a bore, such as a bore 230, for housing at least a portion of the connector. The bore extends from an upper end portion of the stem to a lower end portion of the base. In other words, the bore passes completely through the port body. To help secure the connector with the port body, in some embodiments, a plurality of internal ribs are disposed on an inner surface of the stem or the port body (e.g., an interior surface that defines the bore). In some embodiments, the internal ribs are distributed circumferentially, with each internal rib having a surface configured for abutting an external wall of the connector and thus assists in securing the connector with the port body. In some embodiments, at least one internal rib in the plurality of internal ribs is formed on each of the first stem member and the second stem member.

In some embodiments, the port body 132 includes a tip, such as a tip 240, at a free end portion of the stem and configured for guiding a second device (not shown) when connecting the second device and the connector. As used herein, the free end portion of the stem refers to an end portion of the stem that is distal to the base and not disposed within the retainer. In some embodiments, the tip is a chamfered tip having a chamfer angle "a" and a chamfer length "L1." In some embodiments, the tip is a large chamfered tip with the chamfer angle of at least 45 degrees, at least 50 degrees, at least 55 degrees, or at least 60 degrees. In some embodiments, the stem has a length "L2," and the chamfer length "L1" of the tip is at least 10%, at least 15%, at least 20%, or at least 25% of the length "L2" of the stem. In an exemplary embodiment, the tip is a large chamfered tip with the chamfer angle within a range of from about 50 degrees to about 60 degrees and/or the chamfer length within a range of from about 15% to about 25% of the length of the stem. As such, the tip of the present disclosure makes it easy for robotic systems to interface with the apparatus when connecting the connector and a second device.

In some embodiments, the port body 132 includes one or more first anti-rotation members, such as one or more first anti-rotation members 250. The one or more first anti-rotation members are disposed at the base and configured to couple with one or more second anti-rotation members disposed at the retainer to restrict the port body from rotating relative to the retainer around an axis of the port body. The port body can include any suitable number (e.g., 1, 2, 3, or more than 3) of first anti-rotation members. For instance, in an exemplary embodiment, the port body includes two first anti-rotation members. Moreover, the one or more first anti-rotation members can be disposed at any suitable locations. For instance, in an exemplary embodiment, each of the one or more first anti-rotation members is formed at or adjacent to an outer edge of the base. Further, the one or more first anti-rotation members can be configured with any suitable shape that can be coupled with the second anti-rotation members disposed at the retainer. For instance, in a non-limiting embodiment, each of the one or more first anti-rotation members is a pin formed on the base. In addition, in embodiments with multiple first anti-rotation members, the first anti-rotation members can be but do not have to identical to each other, and can be but do not have to be disposed at locations symmetrical to each other.

Figure 3B:
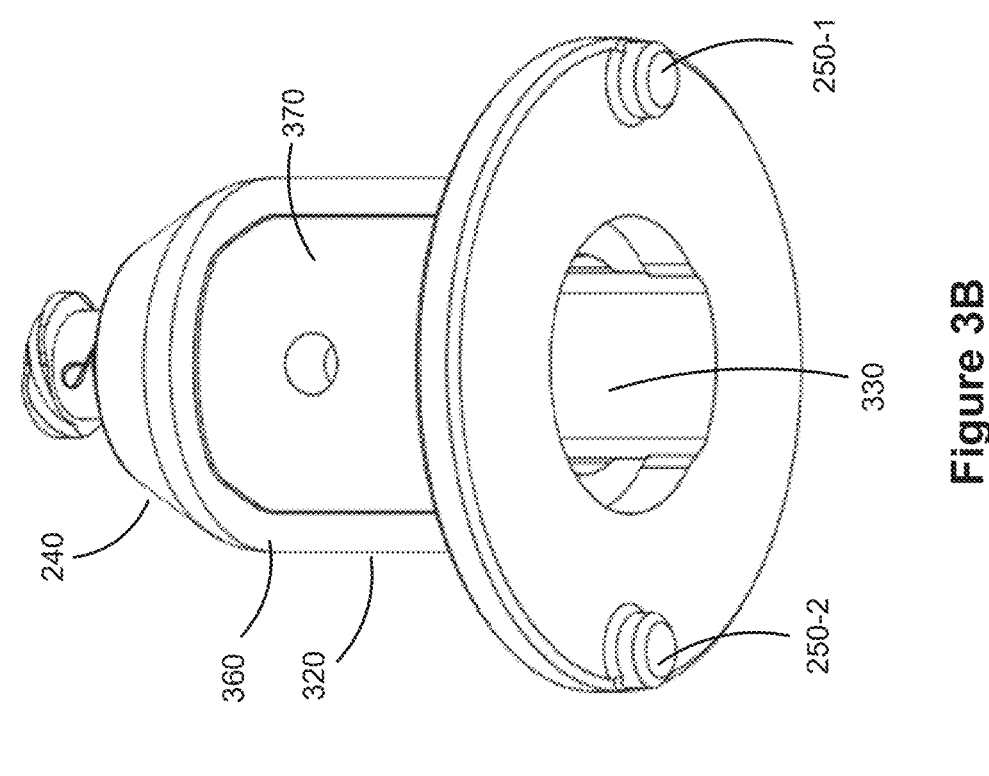
FIG. 3B is another perspective view illustrating the exemplary port body of FIG. 3A.
Figure 3A:
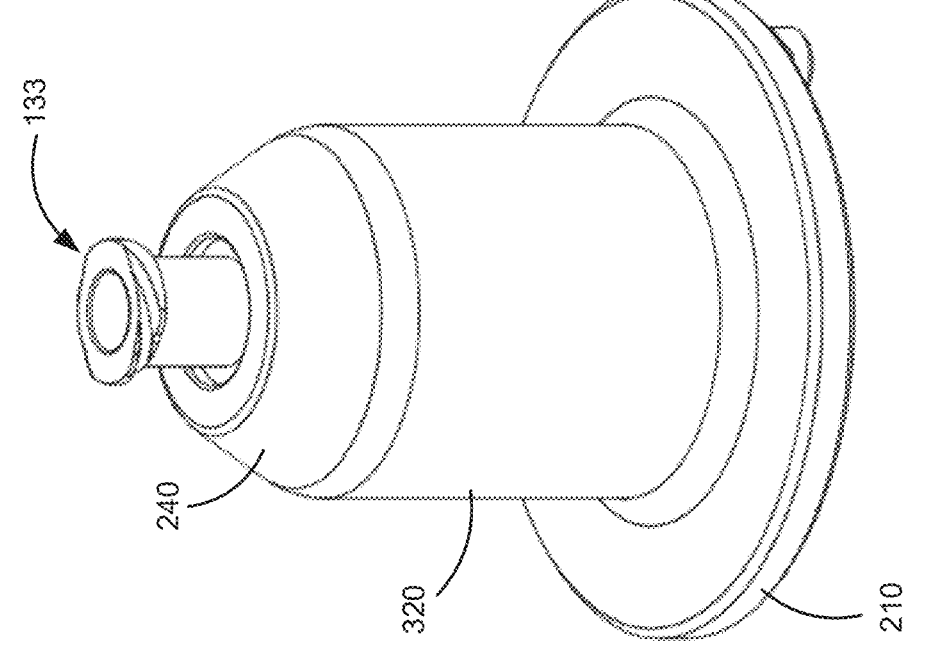
FIG. 3A is a perspective view illustrating an exemplary port body in accordance with some exemplary embodiments of the present disclosure.
Figures 3C, 3D:
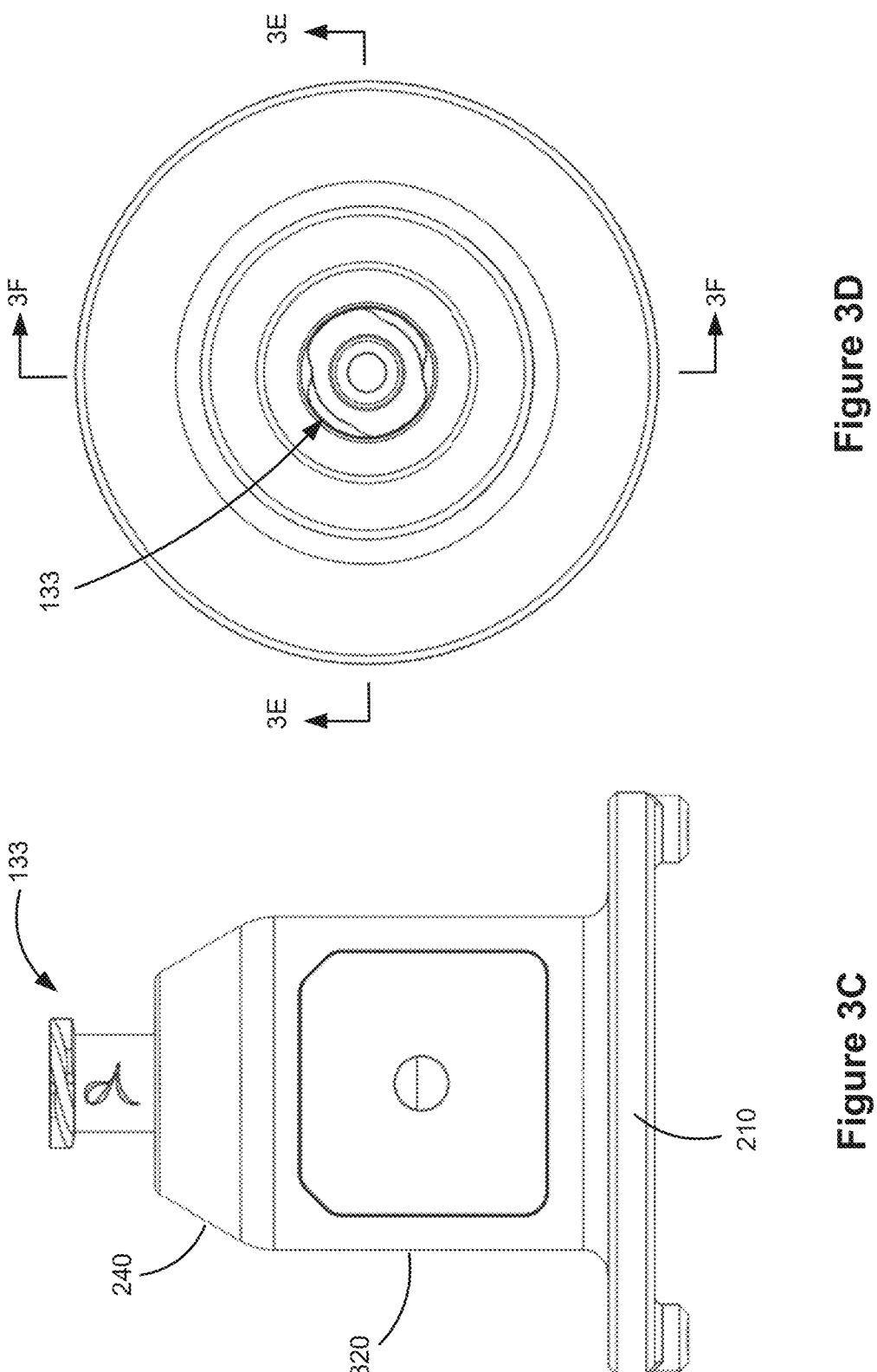
FIG. 3C is a side view illustrating the exemplary port body of FIG. 3A.
FIG. 3D is a top view illustrating the exemplary port body of FIG. 3A.
Figure 3F:
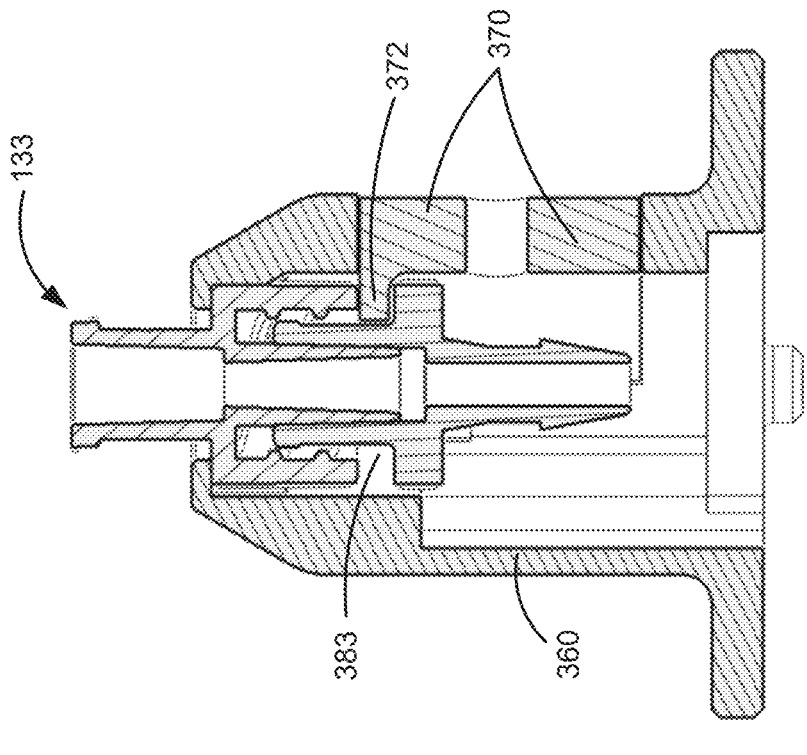
FIG. 3F is another cross-sectional view taken along line 3F-3F of FIG. 3D.
Figure 3E:
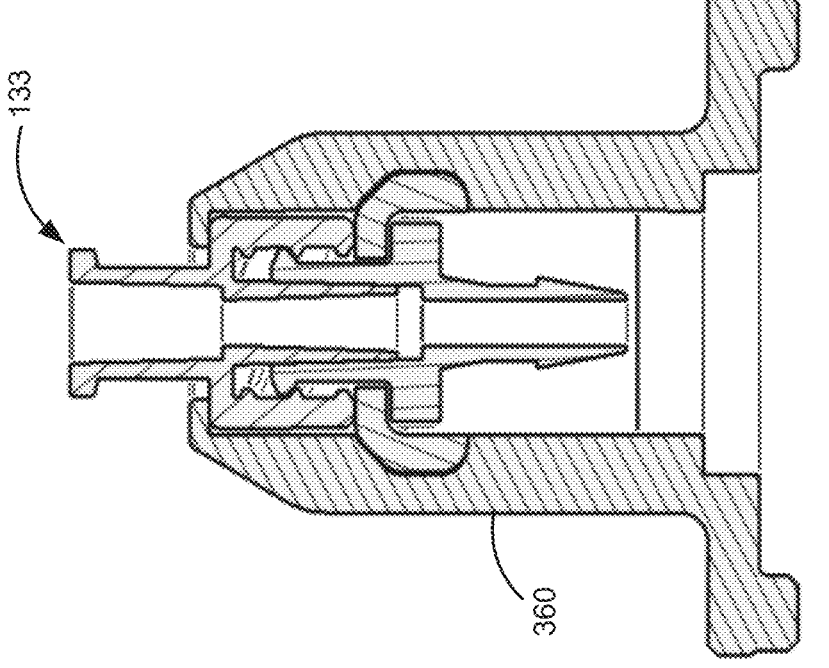
FIG. 3E is a cross-sectional view taken along line 3E-3E of FIG. 3D.

Referring to FIGS. 3A-3E, there is depicted an exemplary port body with an exemplary connector (e.g., a gas connector) housed in the exemplary port body in accordance with some exemplary embodiments of the present disclosure. The port body for housing a gas connector is similar to the port body for housing a gas connector. For instance, in some embodiments, the port body 132 includes a base, such as a base 210. In some embodiments, the port body 132 includes a stem, such as a stem 320, extended from the base 210. The stem 320 is similar to the stem 220, e.g., it is characterized by a length "L2" and a third dimension (e.g., an outer diameter) "D3" that is smaller than the first dimension "D1" of the base. In some embodiments, the stem includes two or more stem members that are removably coupled (e.g., snap-fitted, interference-fitted) with each other and configured to help secure the connector 132 (e.g., a gas connector) at the port body. For instance, in an exemplary embodiment, the stem includes a first stem member 360 and a second stem member 370 removably coupled with each other. In some embodiments, the first stem member is monolithically formed (e.g., molded) with the base as a single piece, and the second stem member is formed as a separate piece (e.g., an insert) to removably couple with the single piece. In some embodiments, the second stem member includes an upper portion 372 and a segment of the upper portion 372 is inserted into a groove (e.g., a neck, a recess) of the connector as illustrated in FIG. 3D, thereby helping to secure the connector on the port body and restrict the connector from moving axially relative to the port body. In some embodiments, the port body 132 includes a bore, such as a bore 330, for housing at least a portion of the connector. The bore 330 is similar to the bore 230, e.g., it passes completely through the port body. In some embodiments, the port body 132 includes a tip, such as a tip 240, at a free end portion of the stem. In some embodiments, the port body 132 includes one or more first anti-rotation members, such as one or more first anti-rotation members 250.

Referring to FIGS. 4A-4J, in some embodiments, each retainer 131 includes a first retaining member. For instance, in the illustrated embodiment, the retainer 131-1 includes a first retaining member 410-1, the retainer 131-2 includes a first retaining member 410-2, the retainer 131-3 includes a first retaining member 410-3, and the retainer 131-4 includes a first retaining member 410-4. While the first retaining members are illustrated to be identical or substantially identical to each other, it should be noted that this is by way of example and it is non-limiting. The first retaining members can be the same as each other or different from each other. In some embodiments, the first retaining member has a first surface 411. A first through-hole, such as a first through-hole 412, is formed at the first retaining member. In some embodiments, the first through-hole is a circular or substantially circular through-hole. The first through-hole is characterized by a fourth dimension (e.g., a diameter) "D4." The fourth dimension "D4" of the first through-hole is larger or substantially larger than the third dimension "D3" of the stem, thereby allowing the stem of the port body to pass through and to move relative to the first retaining member. Moreover, the fourth dimension "D4" of the first through-hole is smaller than the first dimension "D1" of the base, thereby preventing the base of the port body from pulling out of the retainer via the first through-hole.

In some embodiments, each retainer 131 includes a second retaining member, which can be a separate component connected to the upper wall of the cartridge body or an integral component of the upper wall of the cartridge body. For instance, in some embodiments, the upper wall of the cartridge body includes one or more regions, each configured to serve as the second retaining member of a retainer. As a non-limiting example, it is illustrated that the upper wall 121 of the cartridge body includes four regions, e.g., regions 420-1, 420-2, 420-3 and 420-4, configured to serve respectively as the second retaining members of the retainers 131-1, 131-2, 131-3, and 131-4. Accordingly, a region 420 is also referred herein as a second retaining member. While the second retaining members are illustrated to be similar to each other, it should be noted that this is by way of example and it is non-limiting. The second retaining members can be the same as each other or different from each other. In some embodiments, the second retaining member has a second surface 421 spaced apart from the first surface of the first retaining member in an axial direction of the port body, with the base of the port body disposed between the first surface of the first retaining member and the second surface of the second retaining member.

In some embodiments, the second dimension "D2" (e.g., the thickness) of the base equals or substantially equals a distance between the first surface of the first retaining member and the second surface of the second retaining member. For instance, in an exemplary embodiment, the thickness of the base equals or substantially equals a distance between the first surface of the first retaining member and the second surface of the second retaining member with a manufacturing clearance between the base and the first surface of the first retaining member and/or the second surface of the second retaining member. As such, the retainer restricts the base and thus the port body from moving in a direction parallel to the axis of the port body. Accordingly, the retainer restricts the connector from moving in a direction parallel to the axis of the port body.

Figure 4A:
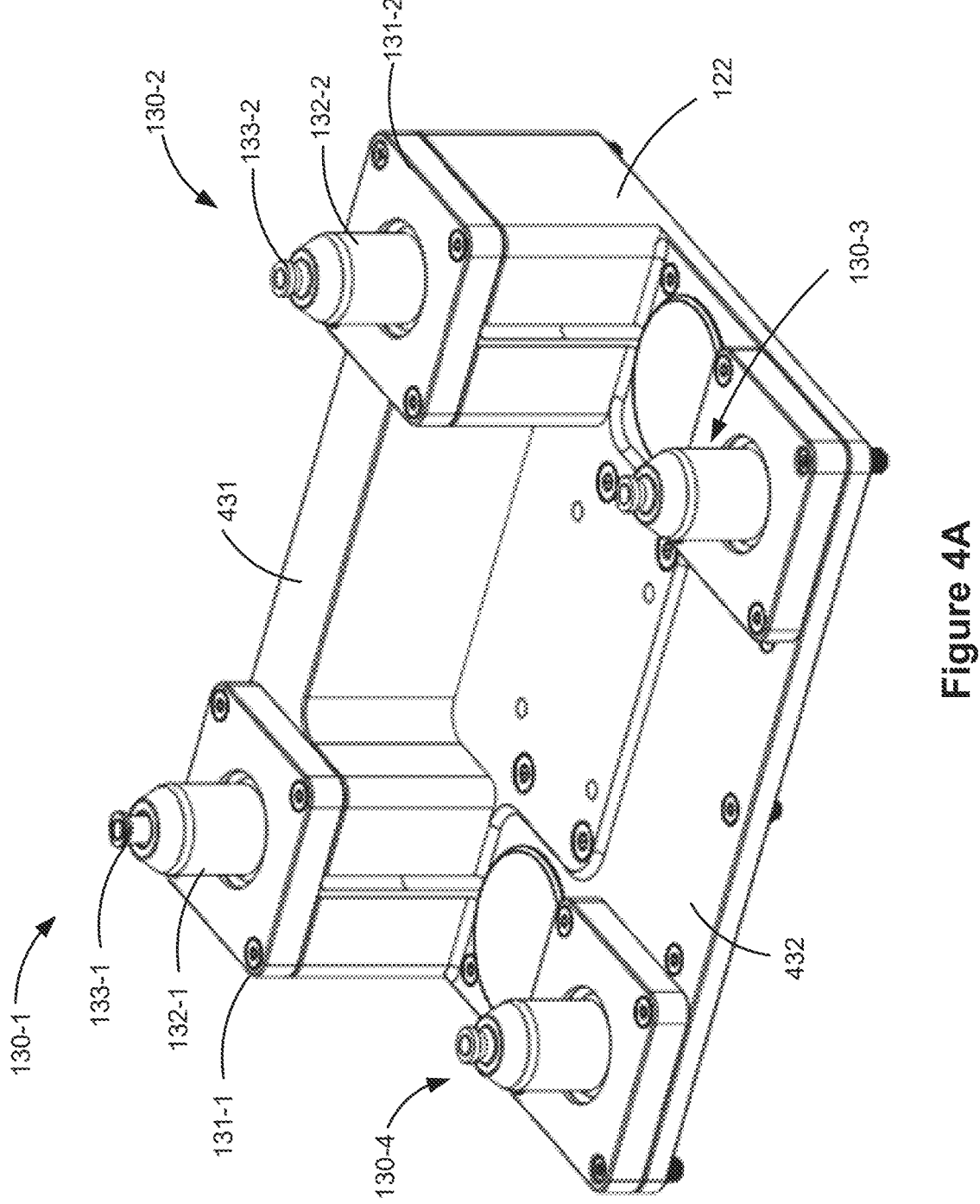
FIG. 4A is a perspective view illustrating some exemplary components of the exemplary apparatus of FIG. 1A in accordance with some exemplary embodiments of the present disclosure.
Figure 4B:
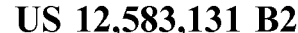
FIG. 4B is a partially exploded view illustrating the exemplary components of FIG. 4A.
Figure 4C:
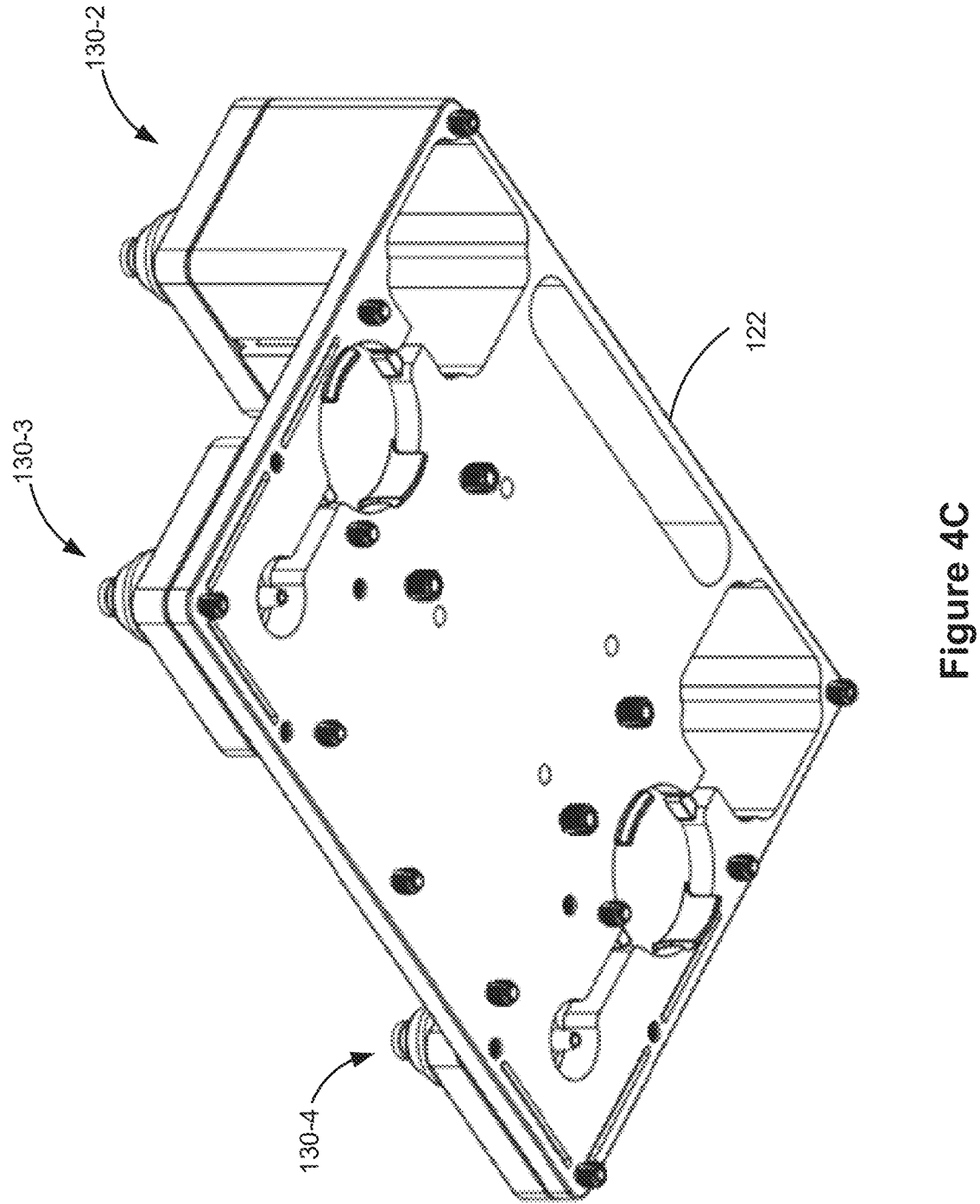
FIG. 4C is another perspective view illustrating the exemplary components of FIG. 4A.
Figure 4D:
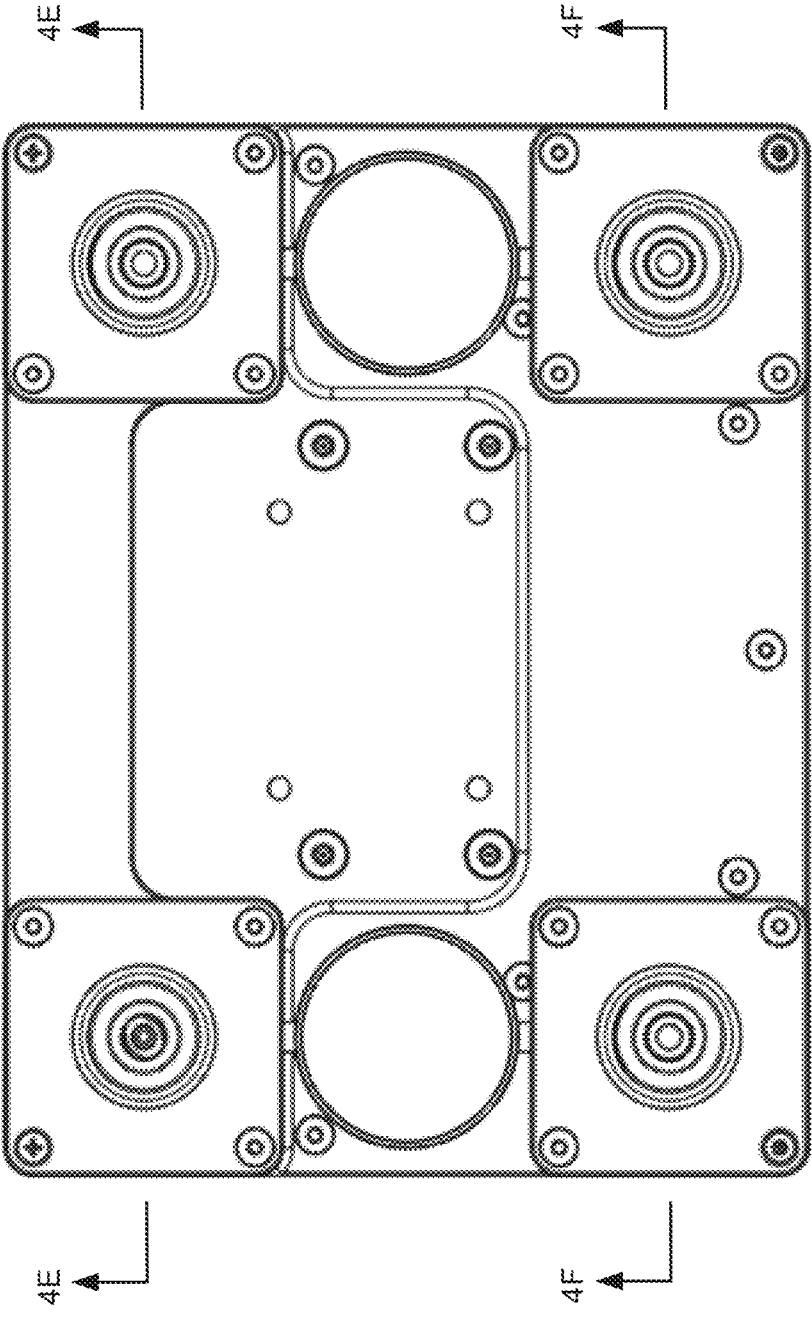
FIG. 4D is a top view illustrating the exemplary components of FIG. 4A.
Figure 4E:
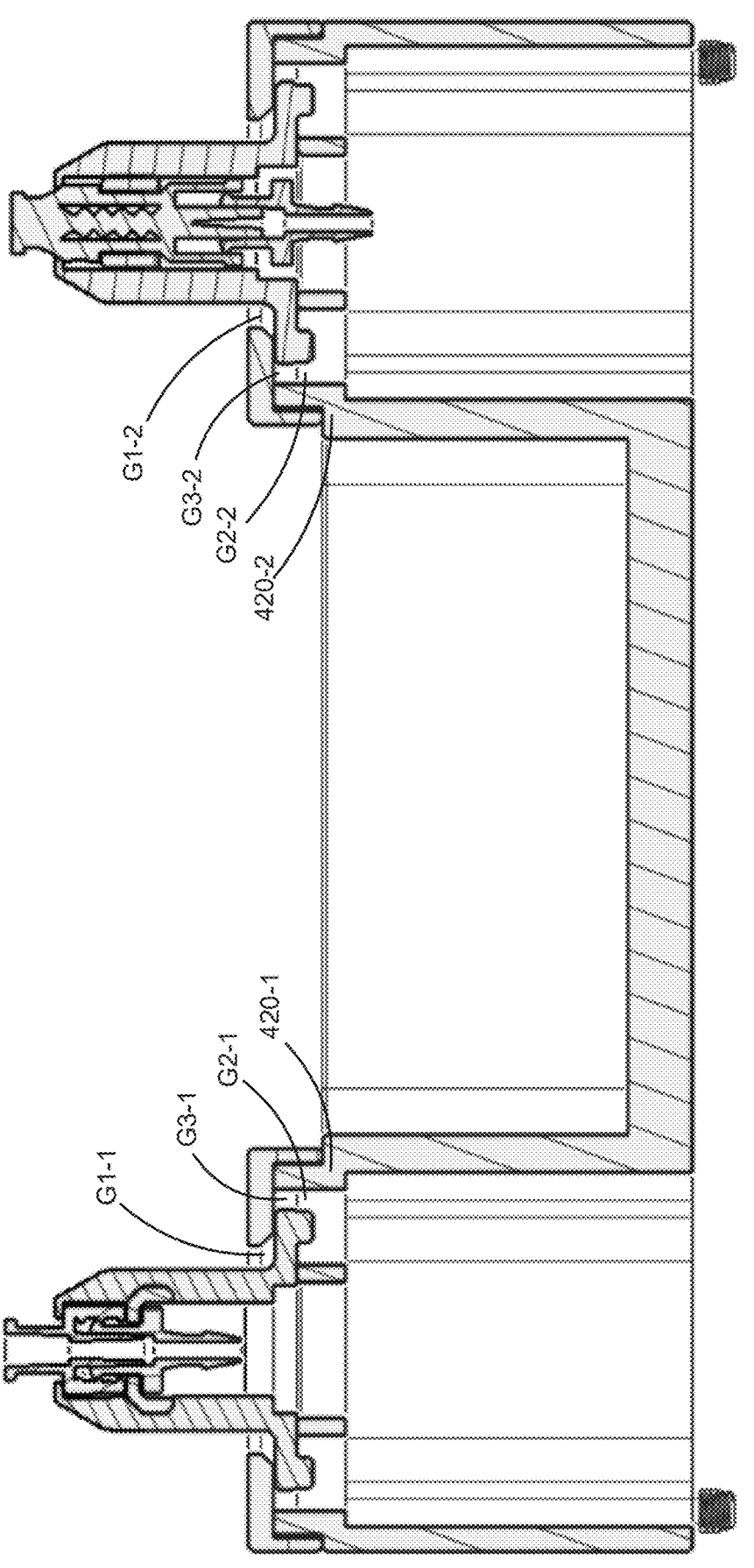
FIG. 4E is a cross-sectional view taken along line 4E-4E of FIG. 4D.
Figure 4F:
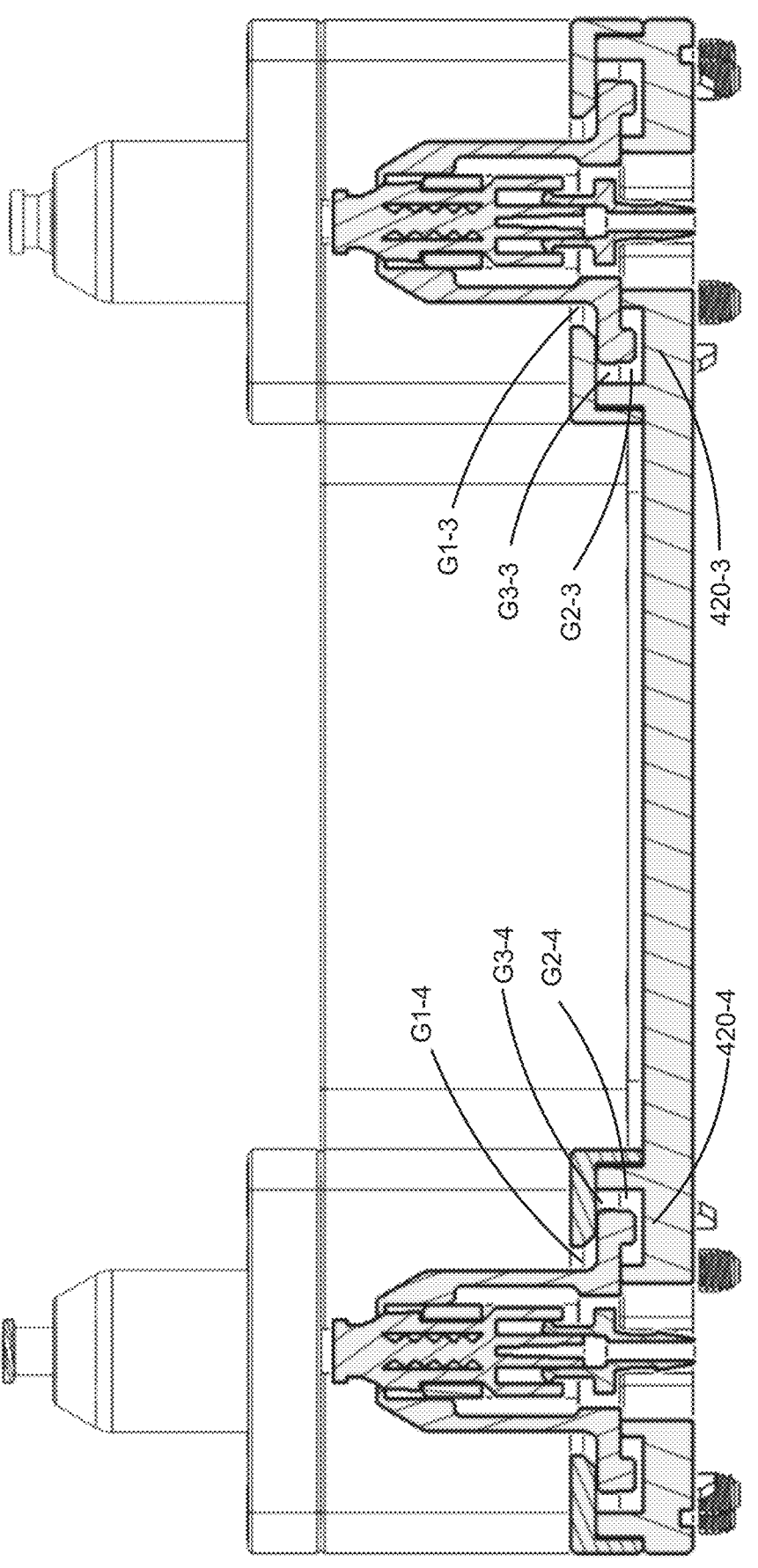
FIG. 4F a cross-sectional view taken along line 4F-4F of FIG. 4D.
Figure 4H:
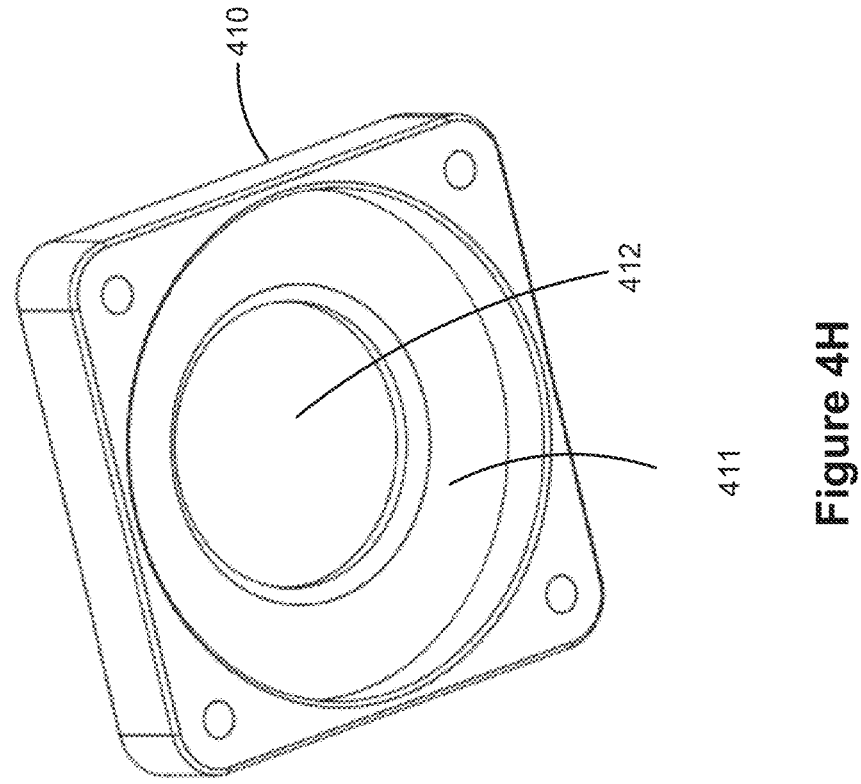
FIG. 4H is another perspective view illustrating the exemplary first retaining member of FIG. 4G.
Figure 4G:
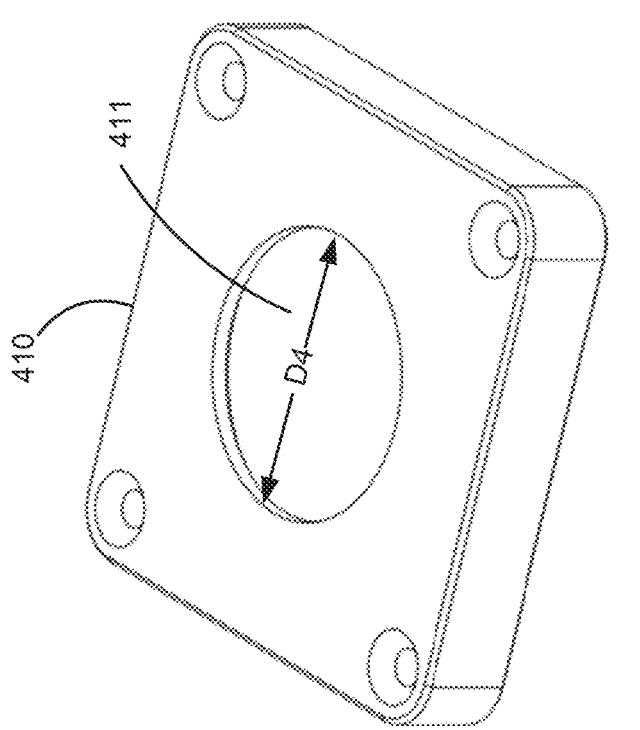
FIG. 4G is a perspective view illustrating an exemplary first retaining member of FIG. 4A in accordance with some exemplary embodiments of the present disclosure.
Figures 4I, 4J:
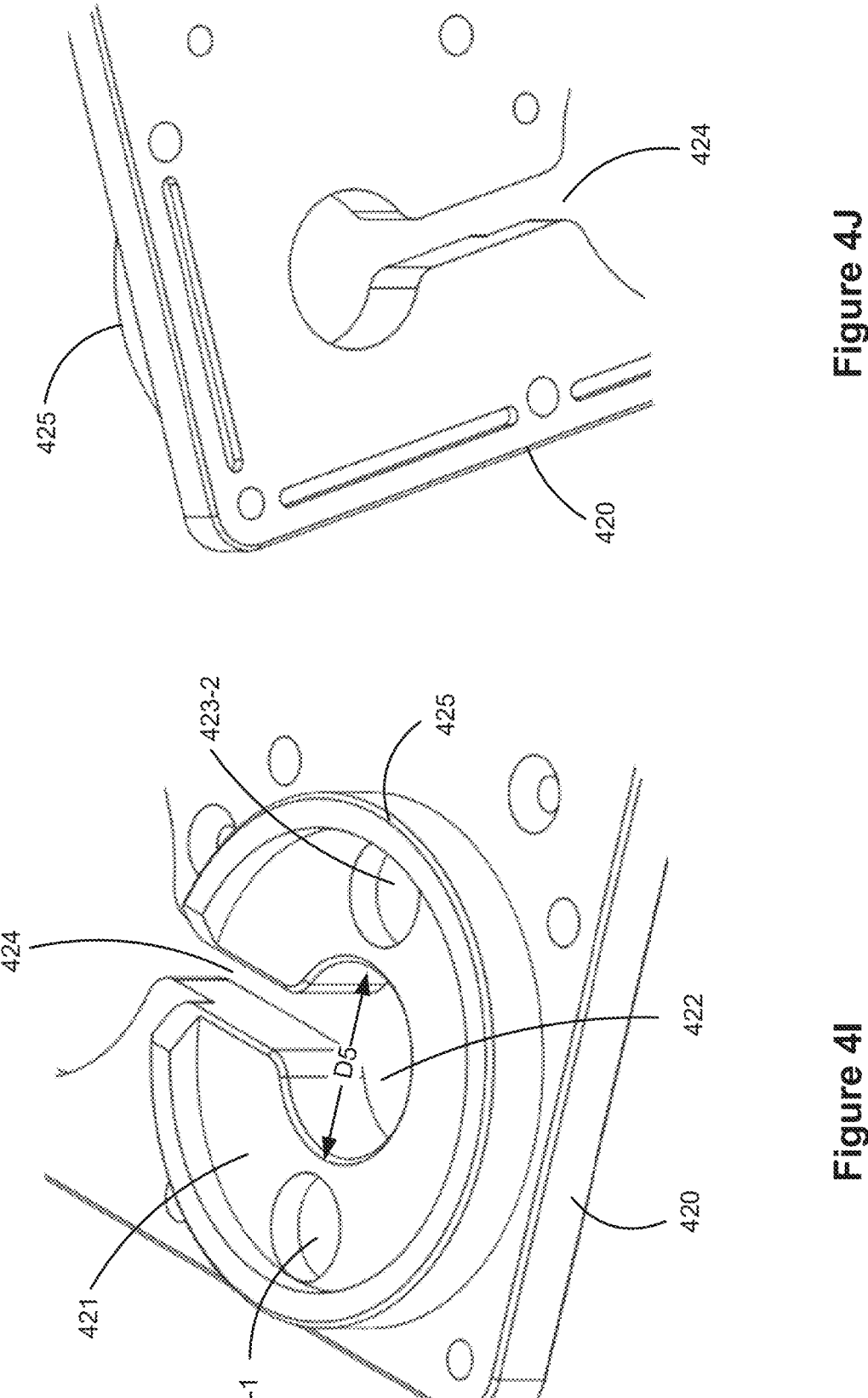
FIG. 4I is a perspective view illustrating a region taken along dash line circle 4I of FIG. 4B in accordance with some exemplary embodiments of the present disclosure.
FIG. 4J is another perspective view illustrating the region of FIG. 4I.
Figure 5A:
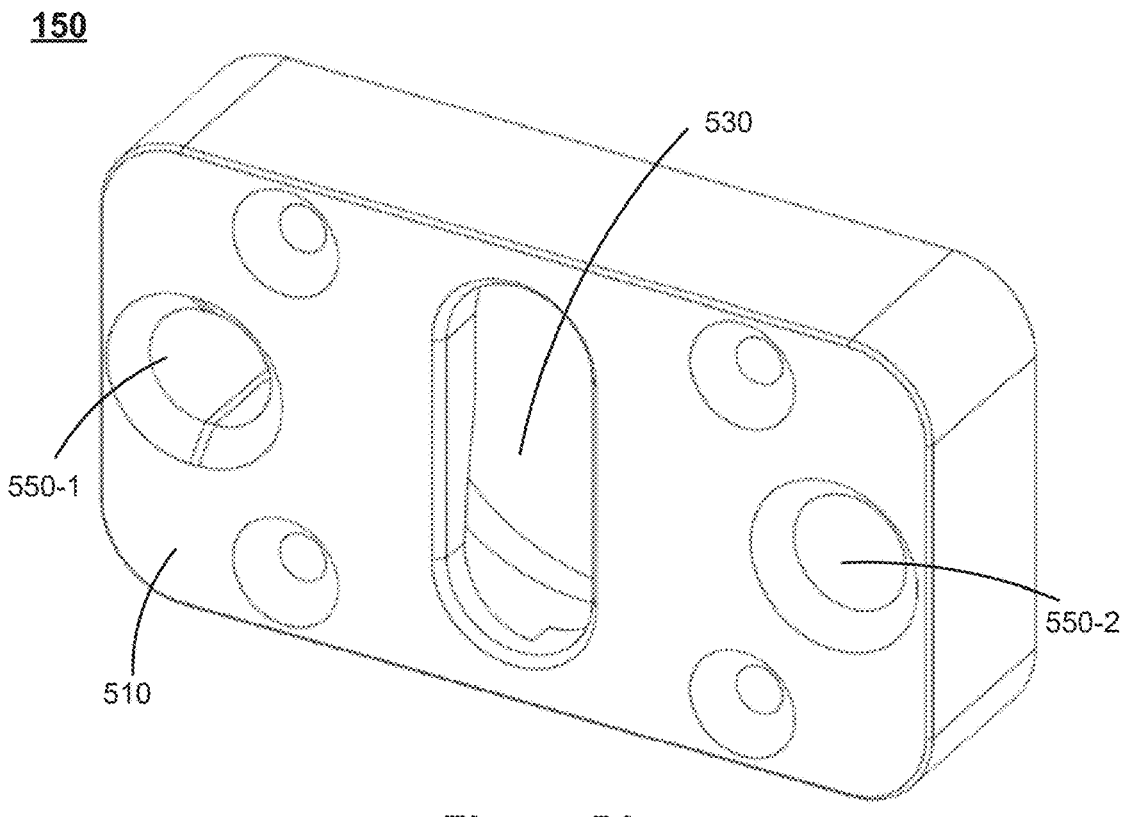
FIG. 5A is a front perspective view illustrating an exemplary interface member in accordance with some exemplary embodiments of the present disclosure.
Figure 5B:
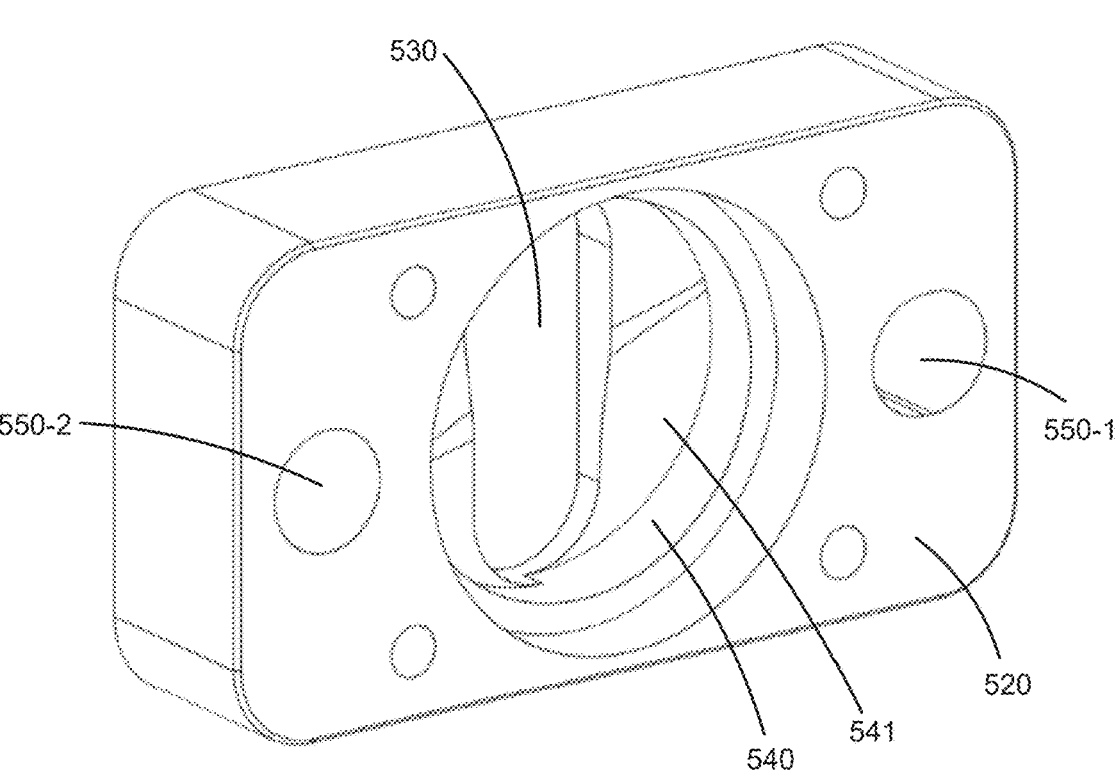
FIG. 5B is a rear perspective view illustrating the exemplary interface member of FIG. 5A.
Figure 5C:
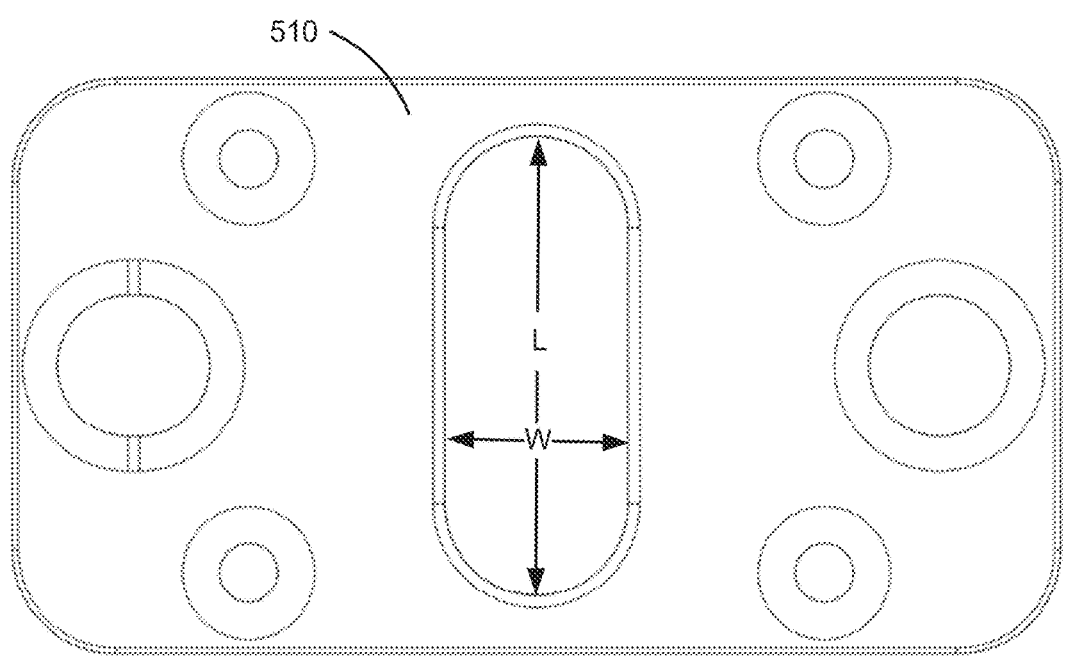
FIG. 5C is a front side view illustrating the exemplary interface member of FIG. 5A.
Figure 5D:
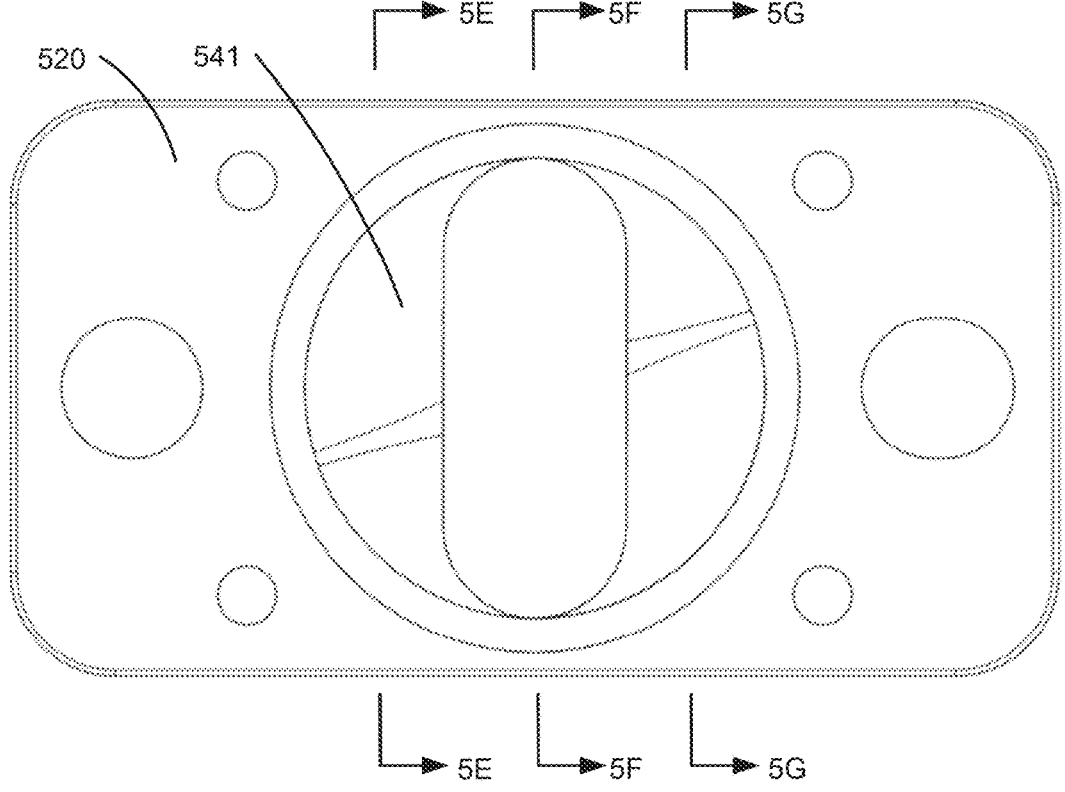
FIG. 5D is a rear side view illustrating the exemplary interface member of FIG. 5A.
Figure 6A:
FIG. 6A is a perspective view illustrating an exemplary robotic end of arm tool (EOAT) for operating the exemplary apparatus of FIG. 1A in accordance with some exemplary embodiments of the present disclosure.
Figure 6B:
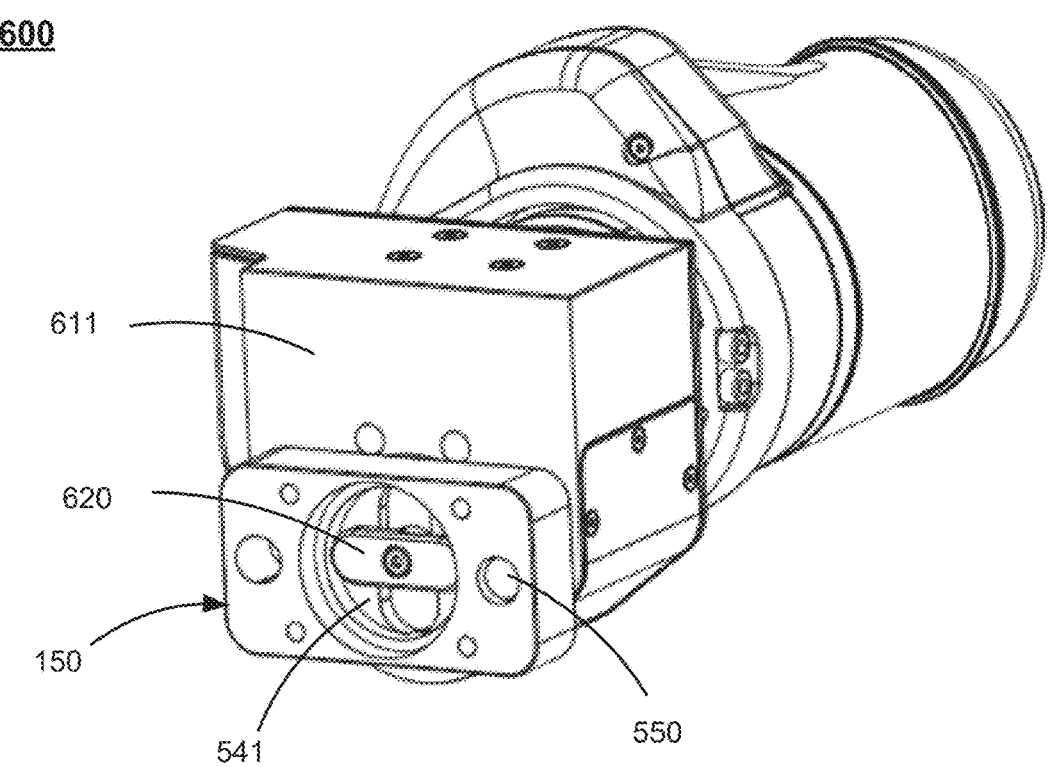
FIG. 6B is a perspective view illustrating the exemplary robotic end of arm tool of FIG. 6A engaged with the exemplary interface member of FIG. 5A in accordance with some exemplary embodiments of the present disclosure.
Figure 6C:
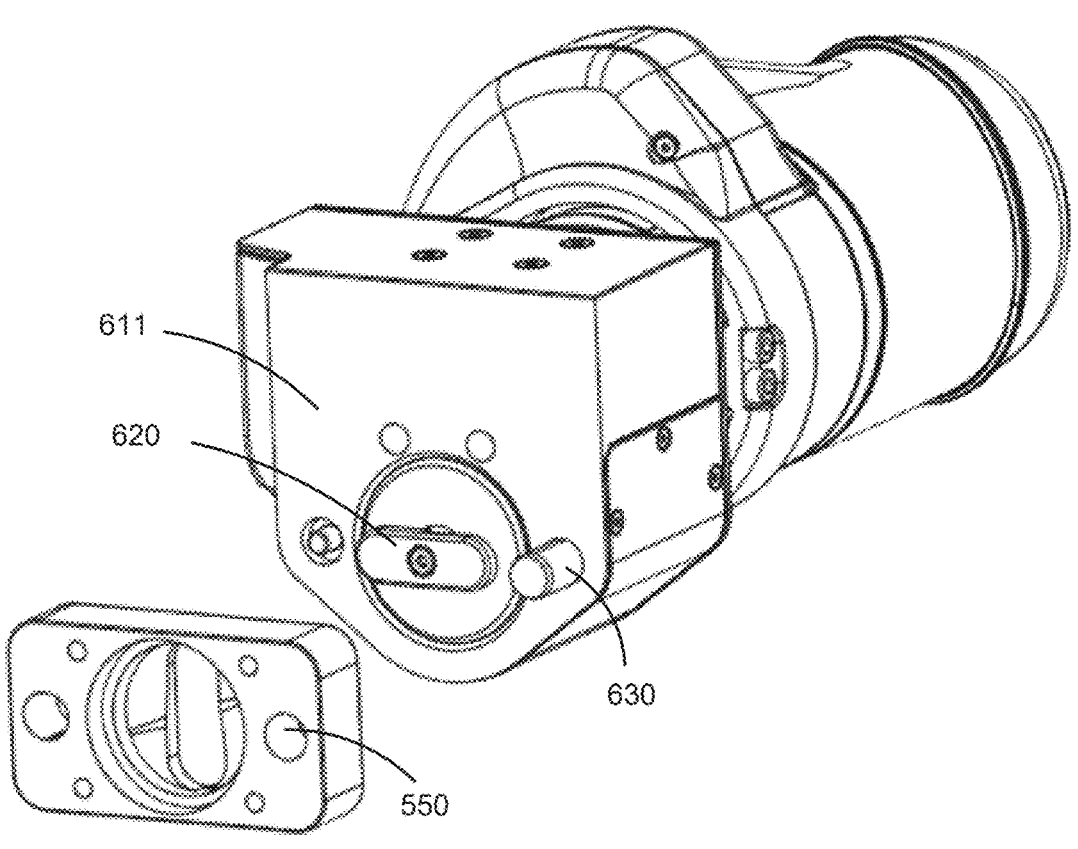
FIG. 6C is a partially exploded view illustrating the exemplary robotic end of arm tool of FIG. 6A and the exemplary interface member of FIG. 5A in accordance with some exemplary embodiments of the present disclosure.
Figures 7A, 7B:
FIG. 7A is a perspective view illustrating an exemplary dock for holding the exemplary apparatus of FIG. 1A in accordance with some exemplary embodiments of the present disclosure.
FIG. 7B is a perspective view illustrating the exemplary dock of FIG. 7A in accordance with some exemplary embodiments of the present disclosure.

In some embodiments, the retainer 131 includes one or more second anti-rotation members, such as second anti-rotation members 422, configured for coupling with the one or more first anti-rotation members of the port body, thereby restricting the port body from rotating relative to the retainer. The one or more second anti-rotation members can be disposed at the first retaining member or the second retaining member. As a non-limiting example, the one or more second anti-rotation members are illustrated at the second retaining member. Like the port body, the retainer can include any suitable number (e.g., 1, 2, 3, or more than 3) of second anti-rotation members. For instance, in an exemplary embodiment, the retainer includes two second anti-rotation members. The one or more second anti-rotation members can be configured with any suitable shape that can be coupled with the first anti-rotation members disposed at the retainer. For instance, in a non-limiting embodiment, each of the one or more second anti-rotation members is a hole formed at the second retaining member to receive a corresponding pin formed on the base. The size of the hole is generally larger than the size of the corresponding pin. The hole can be a blind hole (e.g., a hole that does not pass completely through the second retaining member) or a through hole (e.g., a hole that passes completely through the second retaining member). As a non-limiting example, FIG. 4E illustrates two through holes formed at the second retaining member 420-1 and two through holes formed at the second retaining member 420-2, and FIG. 4F illustrates two blind holes formed at the second retaining member 420-3 and two blind holes formed at the second retaining member 420-4.

However, the present disclosure is not limited thereto. For instance, in some alternative embodiments, each of the one or more second anti-rotation members is a pin disposed at the first retaining member or the second retaining member. Each of the one or more first anti-rotation members is a hole formed at the base to receive a corresponding pin disposed at the first retaining member or the second retaining member.

In some embodiments, one or more through-holes and/or one or more slots are formed at the second retaining member to facilitate connecting the connector with the corresponding tube. For instance, as a non-limiting example, it is illustrated that a second through-hole 423 and a slot 424 are formed on the second retaining member. The second through-hole is configured to allow an access to the connector, and characterized by a fifth dimension (e.g., a diameter) "D5" of the second through-hole. The first dimension "D5" of the second through-hole is smaller than the first dimension "D1" of the base, thereby preventing the base of the port body from pulling out of the retainer via the second through-hole. In some embodiments, the second through-hole is a circular or substantially circular through-hole and concentric with the first through-hole formed on the first retaining member. In some embodiments, the slot extends from the second through-hole all the way to an outer edge of the second retaining member.

In some embodiments, the retainer 131 includes a rim, such as a rim 425, to help set a boundary for translational movement of the port body relative to the retainer. The rim can be disposed on the first surface of the first retaining member or the second surface of the second retaining member. In some embodiments, the rim is an integral part of the first or second retaining member. As a non-liming example, it is illustrated that the rim 425 is formed at the second surface of the second retaining member. The rim can be a single continuous rim or composed of multiple separate rim segments. It can be in a closed form shape or an open form shape. By way of example, the rim is shown to be continuous and in a closed form shape (except the portion cut off by the slot 424) that surrounds the base.

In some embodiments, the retainer 131 and the port body 132 are configured such that one or more gaps are present between the retainer and the port body to confine the translational movement of the port body relative to the retainer. The one or more gaps include but are not limited to:

(i) a first gap "G1" between the stem of the port body and the first through-hole formed on the first retaining member (e.g., a gap between an outer surface of the stem 220 and a surface of the first retaining member that defines the first through-hole 412), (ii) a second gap "G2" between each respective first anti-rotation member in the one or more first anti-rotation members and a corresponding second anti-rotation member in the one or more second anti-rotation members (e.g., a gap between an outer surface of the pin 250 disposed at the base and a surface of the second retaining member that defines the hole 422), (iii) a third gap "G3" between the rim (e.g., an inner surface of the rim) formed on the first surface of the first retaining member or the second surface of the second retaining member and an outer edge of the base of the port body, or (iv) any combination thereof. In some such embodiments, the port body is movable translationally relative to the retainer in the plane perpendicular or substantially perpendicular to the axial direction of the port body within a range defined by the first gap, the second gap, the third gap, or any combination thereof. It should be noted that the first gaps for different connections units (e.g., the first gaps "G1-1," "G1-2," etc.,) can be the same as each other or different from each other. Similarly, the second gaps for different connections units (e.g., the first gaps "G2-1," "G2-2," etc.,) can be the same as each other or different from each other. The third gaps for different connections units (e.g., the first gaps "G3-1," "G3-2," etc.,) can be the same as each other or different from each other.

In some embodiments, the port body is movable translationally relative to the retainer in a radial direction of the port body. In some embodiments, the one or more gaps allow the port body to move translationally relative to the retainer in a radial direction of the port body for at least 1 mm, at least 1.5 mm, at least 2 mm, at least 2.5 mm, or at least 3 mm. in some embodiments, the one or more gaps allow the port body to move translationally relative to the retainer in a radial direction of the port body for at most 5 mm, at most 4.5 mm, at most 4 mm, at most 3.5 mm, or at most 3 mm. In some embodiments, the one or more gaps allow the port body to move translationally relative to the retainer in a radial direction of the port body from about 2 mm to about 3 mm. In an exemplary embodiment, the one or more gaps allow the port body to move translationally relative to the retainer in a radial direction of the port body for about 2.5 mm.

In some embodiments, the upper wall of the cartridge body includes multiple segments at different heights. For instance, as a non-limiting example, it is illustrated that the upper wall of the cartridge body includes a first upper wall segment 431 and a second upper wall segment 432. The first and second upper wall segments are at different heights, e.g., the first upper wall segment is elevated relative to the second upper wall segment. In some embodiments, each of the first and second upper wall segments includes at least one region in the plurality of regions to serve as the second retaining member of at least one retainer. In some embodiments, each of the first and second upper wall segments includes two or more regions in the plurality of regions to serve as the second retaining members of two or more retainers. As a non-limiting example, it is illustrated that each of the first and second upper wall segments includes two regions. That is, the first upper wall segment includes the regions 420-1 and 420-2 to serve respectively as the second retaining members of the retainer 131-1 and 131-2, and the second upper wall segment includes the regions 420-3 and 420-4 to serve respectively as the second retaining members of the retainer 131-3 and 131-4. As such, the port bodies and the connectors of some connection unit(s) (e.g., the connection units 130-1 and 130-2) are positioned higher than those of other connection unit(s) (e.g., the connection units 130-3 and 130-2). This provides space or clearance for interfacing with other devices, such as a cartridge EOAT, a coupler EOAT, and/or other devices.

Referring to FIGS. 1A, 1F, 5A-5G and 6A-6C, in some embodiments, the cartridge 100 includes a mechanism to facilitate moving of the cartridge by a robot (e.g., a robotic end of arm tool). For instance, in some embodiments, the cartridge includes an interface member, such as an interface member 150, to facilitate moving of the cartridge to or from a dock by a robotic end of arm tool (EOAT), such as an EOAT 600 illustrated in FIGS. 6A-6C. The EOAT 600 includes a support having a supporting surface, such as a supporting surface 610, that is planar or substantially planar. The EOAT 600 also includes a cam bar, such as a cam bar 620, that is coupled to the support and is operably ratable around an axis perpendicular or substantially perpendicular to the supporting surface of the support. The cam bar is elongated, e.g., having an elongated cross-section in a plane parallel to the supporting surface of the support with a length larger than a width.

The interface member 150 is connected to (e.g., by one or more fasteners) or formed with the upper wall or the side wall of the cartridge (e.g., by molding of a medical grade plastic material). The interface member generally includes a first interface surface, a second interface surface, an elongated slot and a recess, such as a first interface surface 510, a second interface surface 520, an elongated slot 530 and a recess 540. In some embodiments, the interface member is shaped in a form of a plate, a block or the like.

The first interface surface is accessible from an outside of the cartridge (e.g., the facing away from the cartridge) and the second interface surface is opposite to the first interface surface (e.g., facing the mounting member). The first interface surface is configured for abutting the supporting surface of the EOAT when the EOAT grips the interface member. In some embodiments, the first interface surface is planar or substantially planar.

The elongated slot is formed through the first interface surface and configured to allow the elongated cam bar of the EOAT to insert into the interface member. In some embodiments, the elongated slot has a width, e.g., a width "W," and a length, e.g., a length "L." The width of the elongated slot is equal to or greater than the width of the elongated cam bar of a robotic end of arm tool (EOAT) but smaller than the length of the cam bar of the EOAT. The length of the elongated slot is equal to or greater than the length of the cam bar of the EOAT. As such, the elongated slot allows insertion of the cam bar of the EOAT into the interface member and removal of the cam bar of the EOAT from the interface member when the cam bar of the EOAT is aligned or substantially aligned with the elongated slot.

The recess is recessed from the second interface surface toward the first interface surface. It has a dimension, e.g., a diameter "D," that is larger than the width of the elongated slot and the length of the elongated cam bar, thereby allowing the elongated cam bar of the EOAT to rotate within the interface member. In some embodiments, the recess is a circular blind hole formed through the second interface surface and aligned with the elongated slot. In some embodiments, the recess has a bottom surface, such as a bottom surface 541 within the interface member. The bottom surface is characterized by a first cam profile, e.g., curved or slanted relative to the first interface surface. As a non-limiting example, FIGS. 5E-5G illustrate an exemplary profile of the bottom surface in accordance with some exemplary embodiments of the present disclosure. However, the present invention is not limited to. The bottom surface can be configured with other profiles. In some embodiments, a surface of the cam bar that faces the supporting surface of the support is characterized by a second cam profile. In some embodiments, the cam bar includes one or more chamfered edges (e.g., 45 degrees chamfered edge). In some embodiments, the first cam profile of the bottom surface of the recess of the interface member and the second cam profile of the surface of the cam bar are complemental to each other.

When the cam bar of the EOAT rotates, the cam bar of the BOAT abuts the bottom surface of the recess of the interface member while the first interface surface of the interface member abuts the supporting surface of the EOAT. As such, the EOAT grips the interface member and thus the cartridge. Accordingly, the cartridge can be moved to any desired location on demand by the EOAT through the interface member. In some embodiments, the cam profile of the cam bar includes one or more chamfered edges (e.g., one or more 45 degree chamfered edges), thereby allowing the cam bar to rotate to a lock position and jamming against the bottom surface of the recess of the interface member as a hard stop.

In some embodiments, the interface member 150 includes a plurality of first alignment elements, such as first alignment elements 550, connected to or formed with the interface member. The EOAT 600 includes a plurality of second alignment elements, such as second alignment elements 630, connected to or formed with the support. The first and second alignment elements are configured to couple with each other. In some embodiments, one of the first and second alignment elements is a pin and the other of the first and second alignment elements is a pin hole. As a non-limiting example, it is illustrated that the interface member includes a plurality of pin holes (e.g., 2 pin holes) and the EOAT includes a plurality of pins (e.g., 2 pins), of which each respective pin hole in the plurality of pin holes is configured to receive a corresponding pin in the plurality of pins, thereby facilitating alignment of the robotic EOAT with interface member.

Referring to FIG. 1H-1J and 7A-7B, in some embodiments, the cartridge 100 includes a mechanism to facilitate alignment, positioning and/or and locking of the cartridge on a dock, such as a dock 700. For instance, in some embodiments, the cartridge 100 includes one or more alignment elements, such as alignment elements 170-1 and 170-2, formed at a lower portion of the side wall of the cartridge body to facilitate alignment and positioning of the cartridge on the dock. An alignment element 170 can be a pin or a pin hole. As a non-limiting example, each of the alignment elements 170-1 and 170-2 is illustrated to be a pin hole. In some embodiments, the cartridge 100 includes one or more locking elements, such as locking members 180-1, 180-2, 180-3 and 180-4, disposed at a lower portion of the side wall of the cartridge body to facilitate positioning and locking of the cartridge on a dock. A locking element 180 can be an electromagnet or an electromagnet target. However, the present disclosure is not limited thereto, other alignment, positioning and/or locking elements can be used. In addition, the alignment, positioning and/or locking elements can be disposed in other locations and/or in different combinations.

In various embodiments, the dock includes a novel design that incorporates leveling features, electromagnet locking features and/or other features. One of the key innovations is a combination of locating and locking features that work in conjunction with the cartridge design to enable a standard bioreactor to have repeatable positioning capability, robot compatible gripping and handling, and/or position locking capabilities to allow couplers to be twisted on and off the cartridge ports.

In some embodiments, the dock 700 includes a mounting base, a first mounting member, a second mounting member, one or more alignment elements (e.g., hole or pin), one or more locking elements (e.g., electromagnet or electromagnet target), or any combination thereof. For instance, in some embodiments, the dock 700 includes a mounting base 710, a first mounting member 720, a second mounting member 730, one or more alignment elements such as pins 740, and one or more locking elements such as electromagnets 750. The first mounting member is connected to the mounting base and spaced apart from the mounting base in a first direction (e.g., the vertical direction in the figure). The first mounting member includes a first through-hole, such as a first through-hole 721. The second mounting member is connected to the first mounting member by a plurality of leveling mounts, such as leveling mounts 731. Each of the plurality of leveling mounts has a height that is adjustable and lockable. The second mounting member includes a second through-hole, such as a second through-hole 732, concentric with the first through-hole of the first mounting member to accommodate the device 110. The plurality of pins 740 is disposed at the second mounting member and corresponds to a plurality of pin holes 170 of the cartridge to facilitate positioning and locking of the cartridge on the dock. The plurality of electromagnets 750 is disposed at the second mounting member and corresponds to a plurality of electromagnet targets 180 of the cartridge to facilitate positioning and locking of the cartridge on the dock. In some embodiments, each of the plurality of pins 740 is tapered. In some embodiments, the second through-hole 332 is a clearance hole. In some embodiments, adjusting the heights of the plurality of leveling mounts allows the vessel of the cartridge to sit on the mounting base. In some embodiments, the dock further includes one or more spherical joint pivots, such as a joint pivot 760.

Figures 8A, 8B:
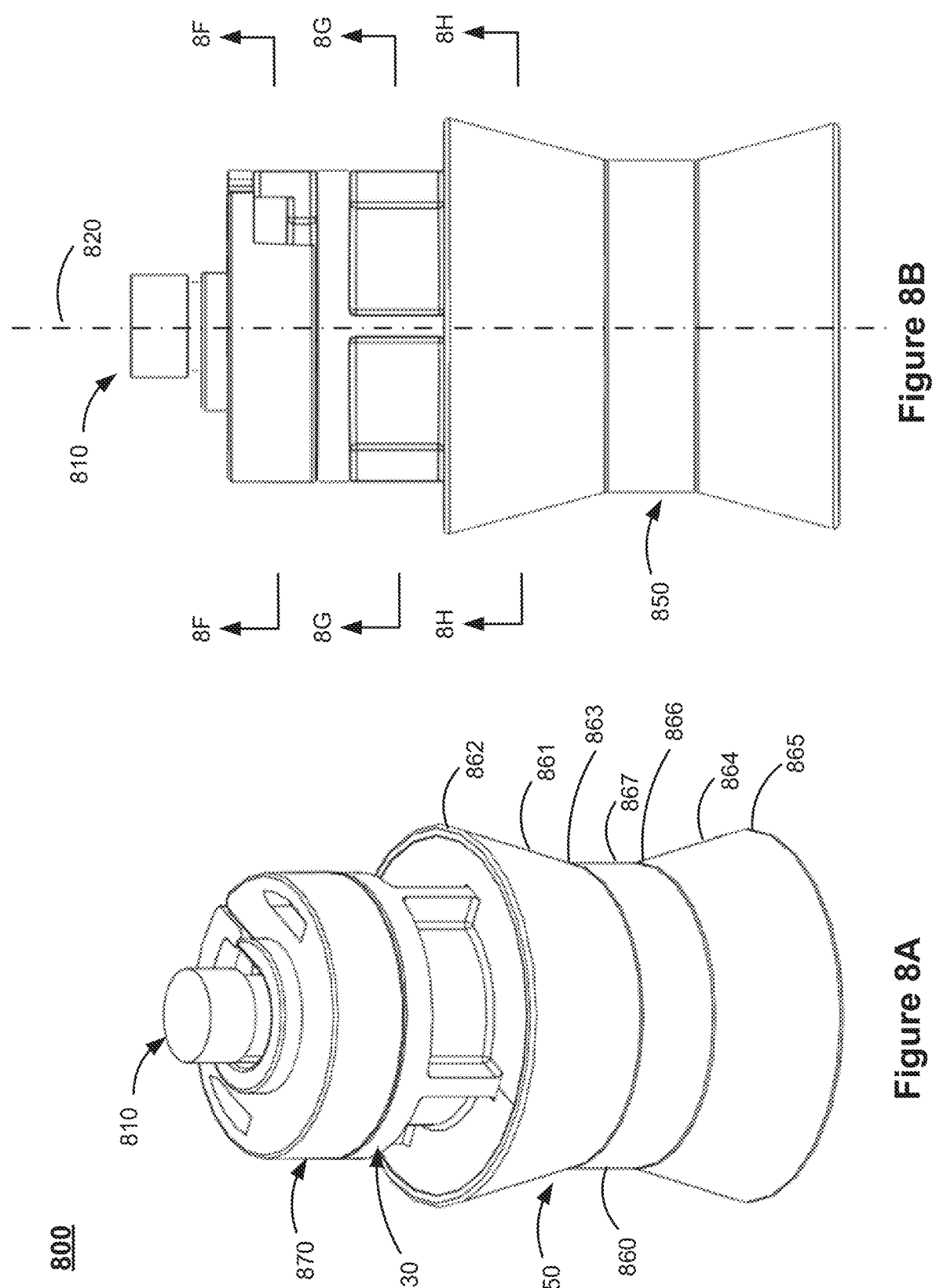
FIG. 8A is a perspective view illustrating an exemplary apparatus (also referred herein as a coupler) in accordance with some exemplary embodiments of the present disclosure.
FIG. 8B is a side view illustrating the exemplary apparatus of FIG. 8A.
Figure 8C:
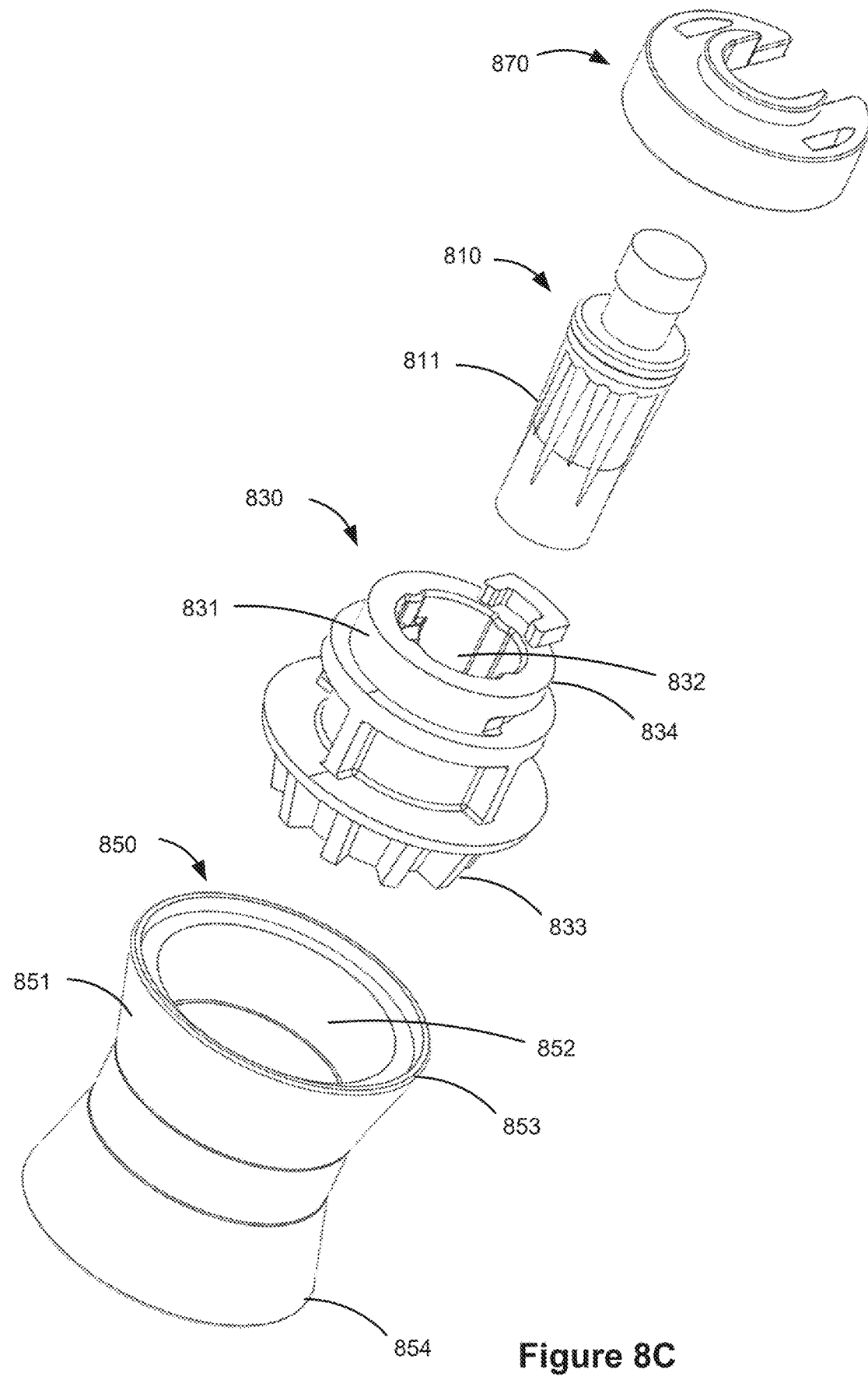
FIG. 8C is an exploded view illustrating the exemplary apparatus of FIG. 8A.
Figure 8E:
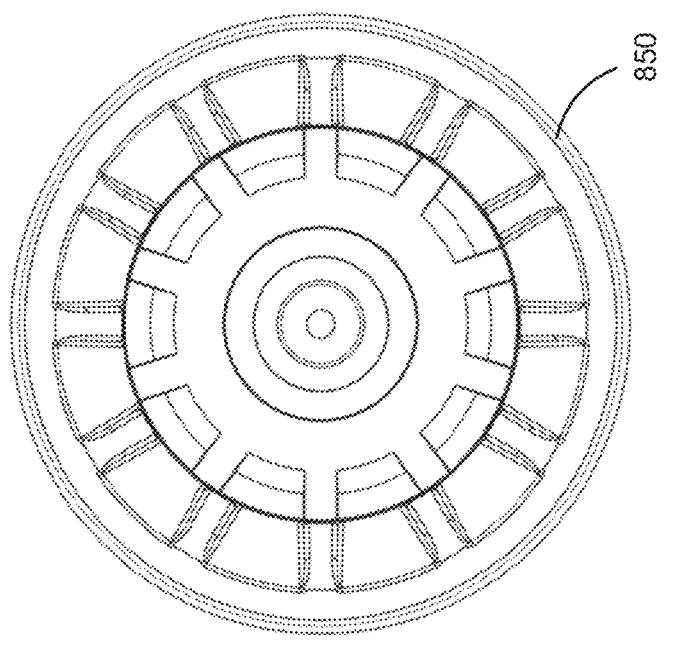
FIG. 8E is a bottom view illustrating the exemplary apparatus of FIG. 8A.
Figure 8D:
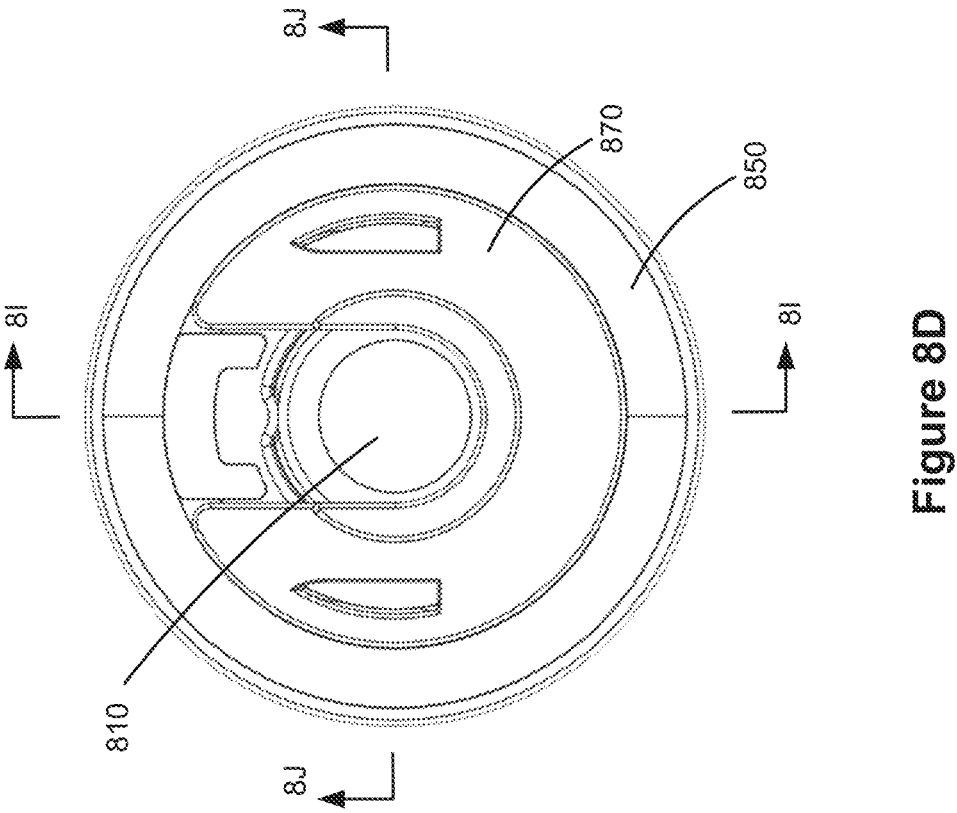
FIG. 8D is a top view illustrating the exemplary apparatus of FIG. 8A.
Figures 8F, 8G, 8H:
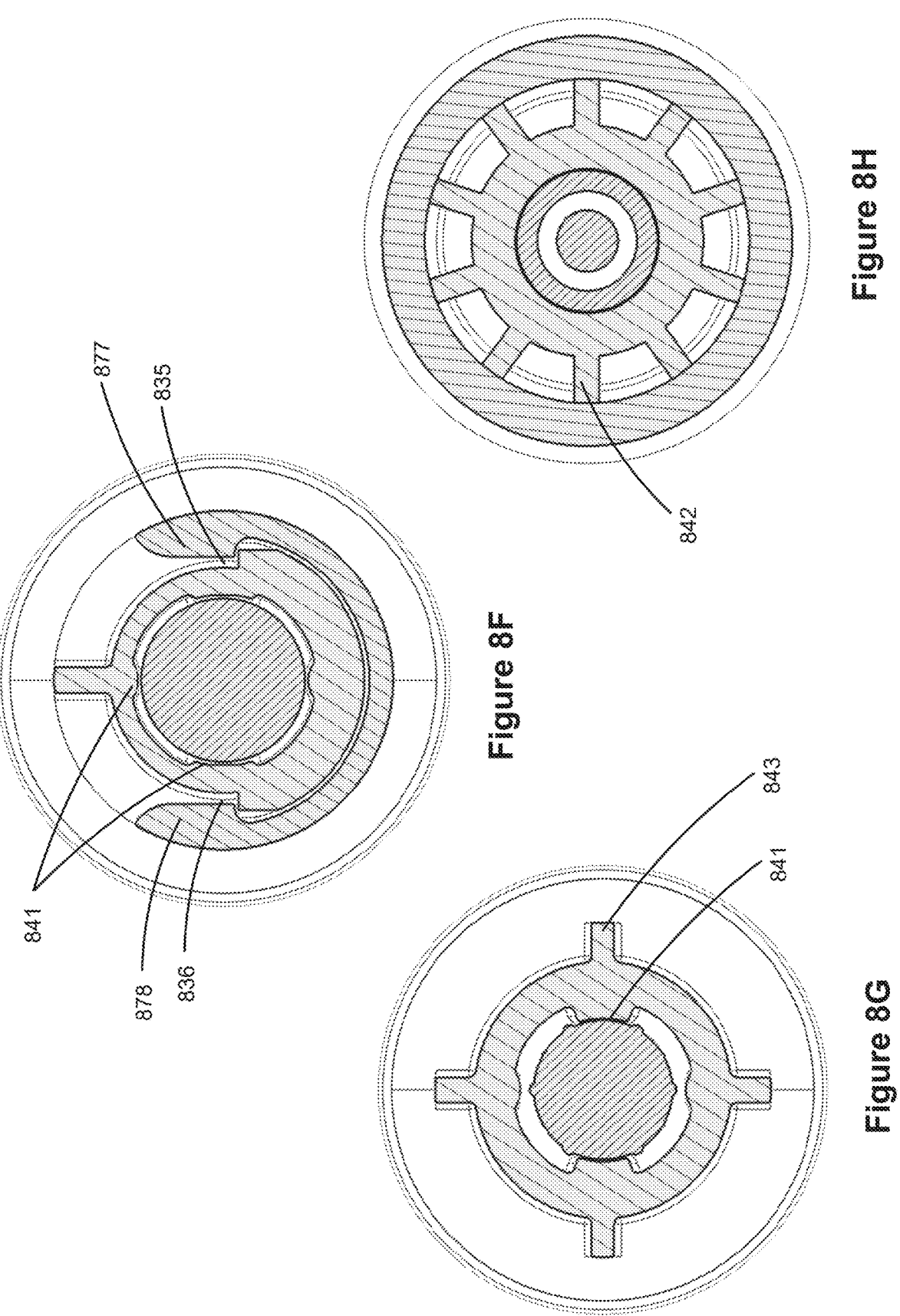
FIG. 8F is a cross-sectional view taken along line 8F-8F of FIG. 8B.
FIG. 8G is a cross-sectional view taken along line 8G-8G of FIG. 8B.
FIG. 8H is a cross-sectional view taken along line 8H-8H of FIG. 8B.
Figures 8I, 8J:
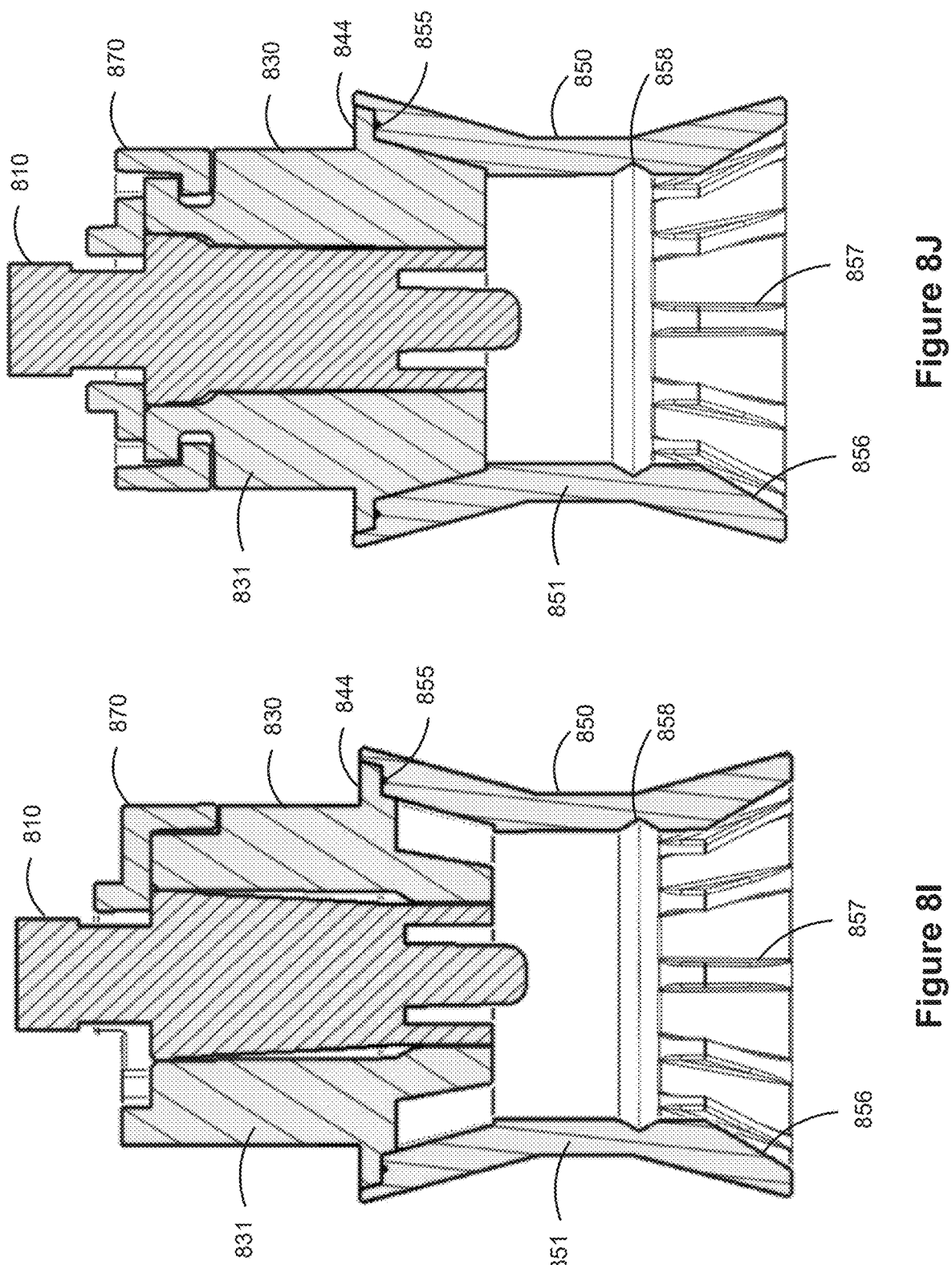
FIG. 8I is a cross-sectional view taken along line 8I-8I of FIG. 8D.
FIG. 8J is a cross-sectional view taken along line 8J-8J of FIG. 8D.
Figure 8L:
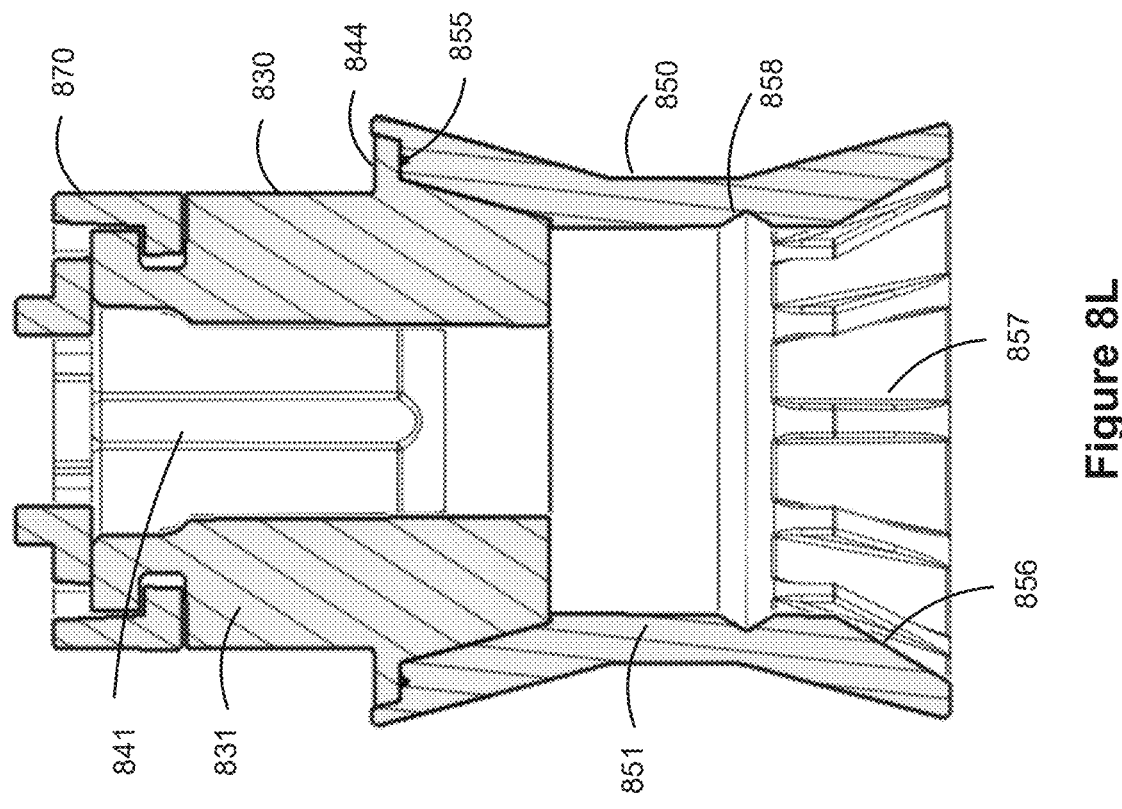
FIG. 8L is a cross-sectional view of FIG. 8J, where a connector is removed.
Figure 8K:
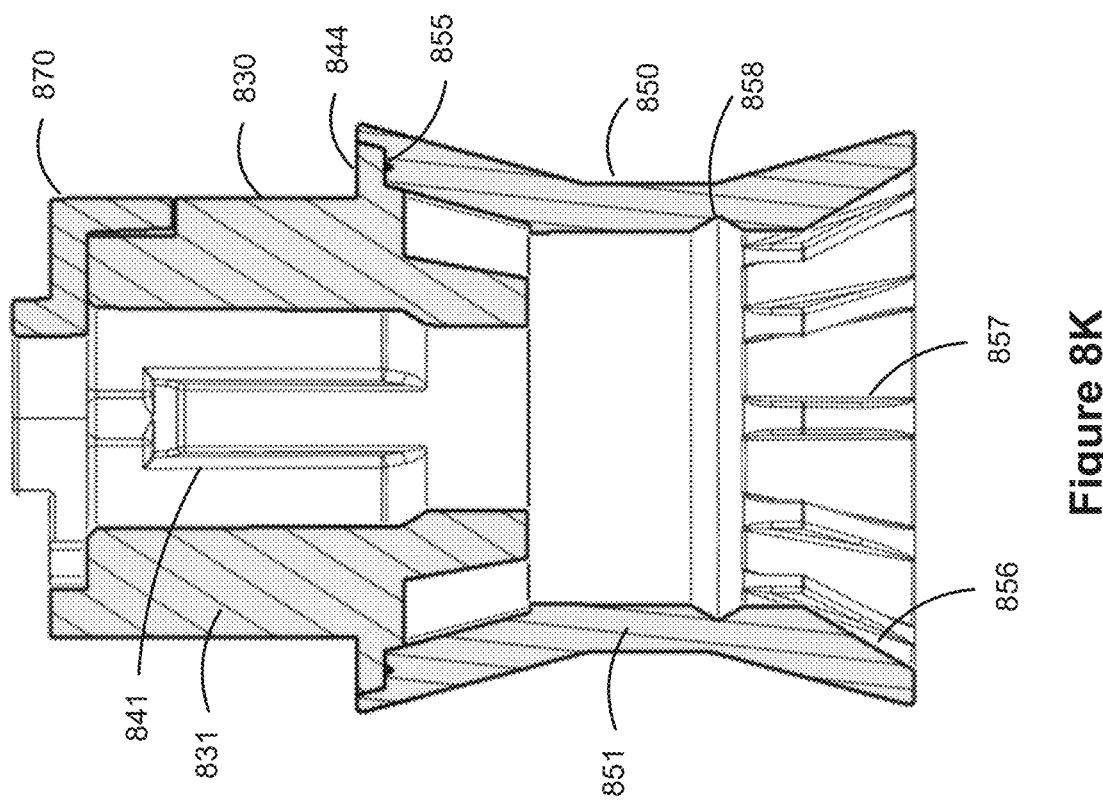
FIG. 8K is a cross-sectional view of FIG. 8I, where a connector is removed.
Figures 8M, 8N:
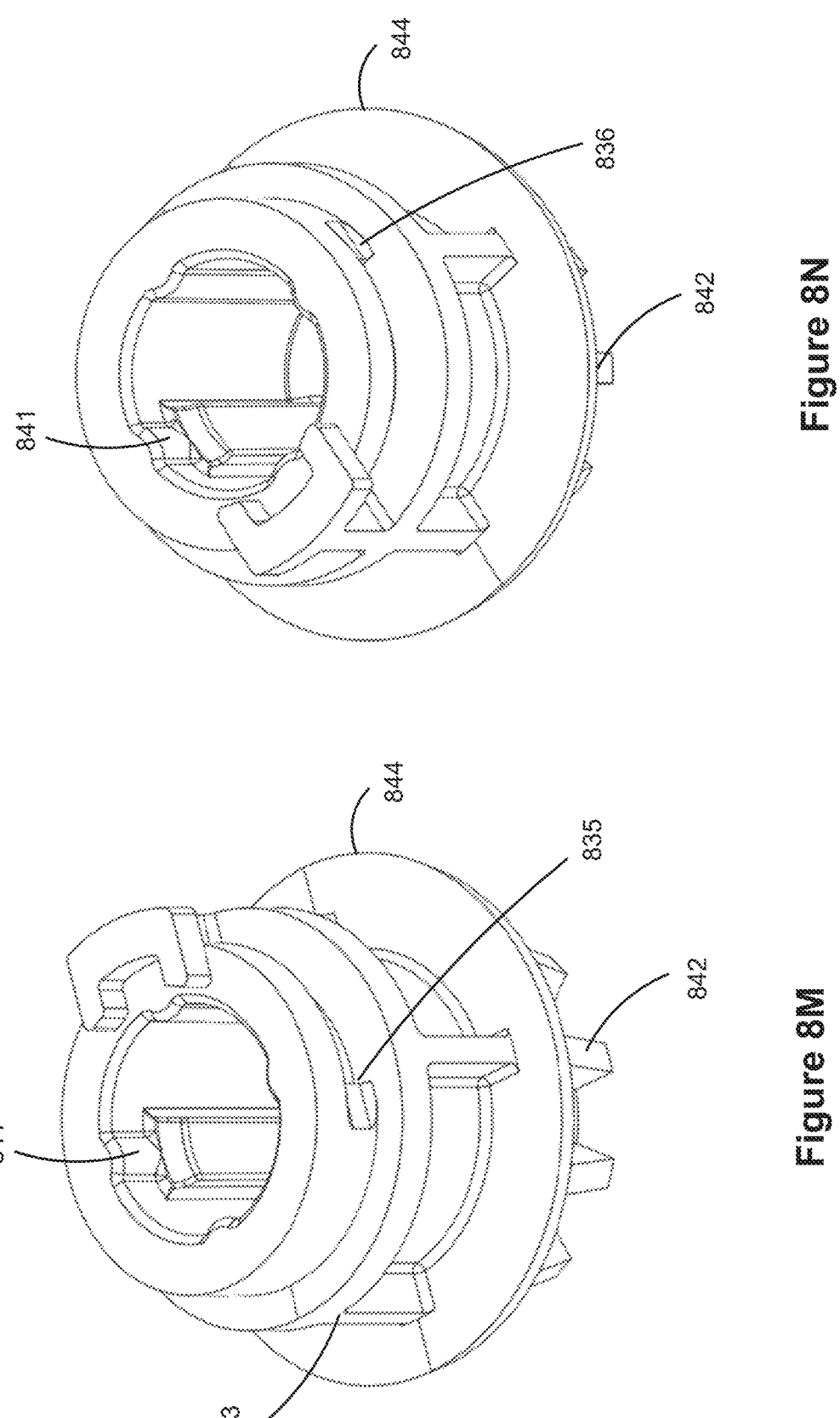
FIGS. 8M and 8N are perspective views illustrating an exemplary component of the exemplary apparatus of FIG. 8A in accordance with some exemplary embodiments of the present disclosure.
Figure 8P:
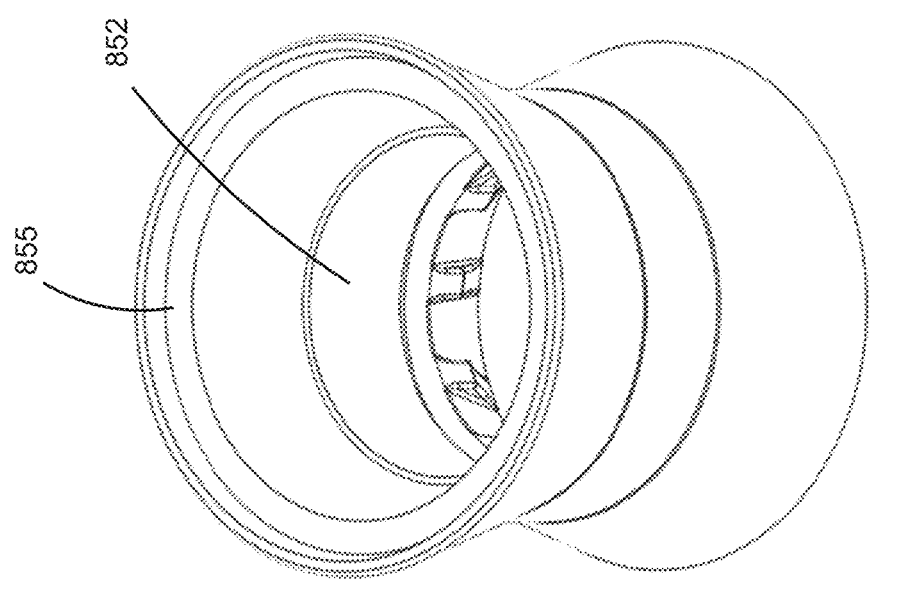
FIGS. 8O and 8P are perspective views illustrating another exemplary component of the exemplary apparatus of FIG. 8A in accordance with some exemplary embodiments of the present disclosure.
Figure 8O:
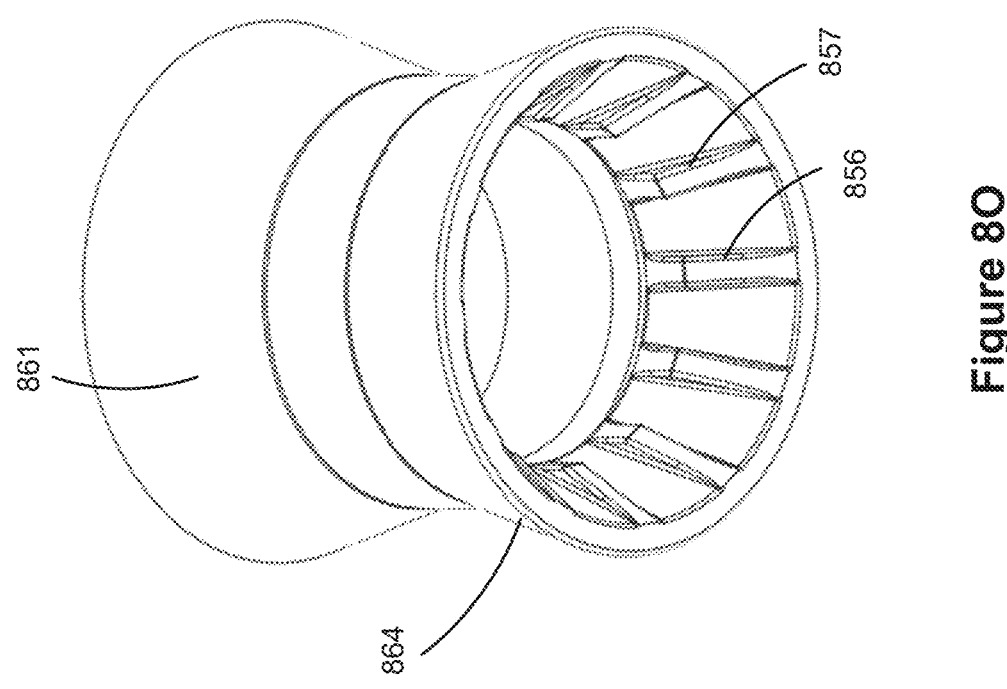
Figure 8Q:
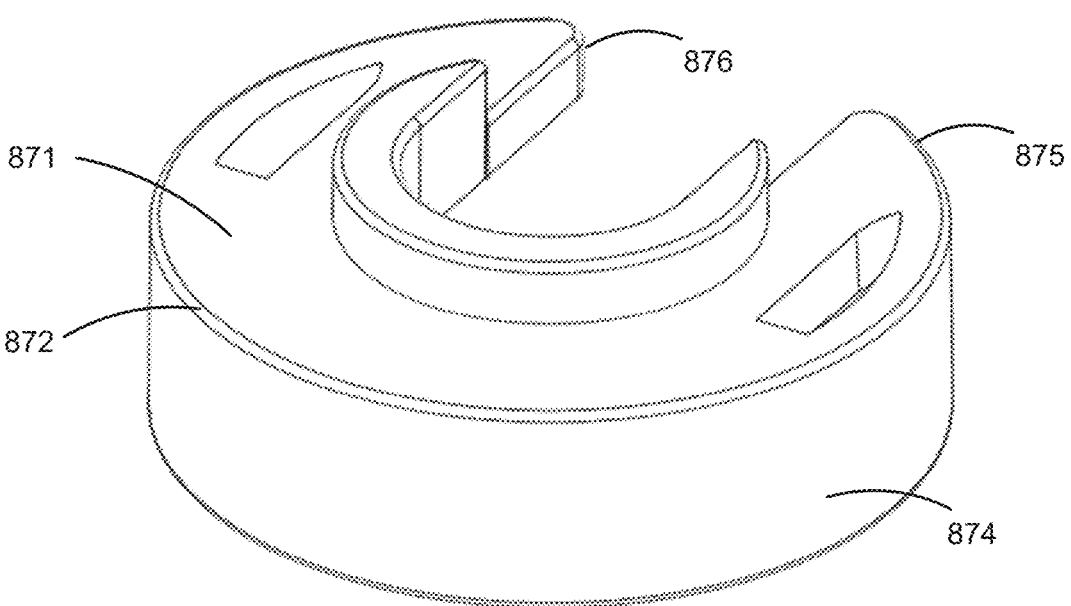
FIGS. 8Q and 8R are perspective views illustrating another exemplary component of the exemplary apparatus of FIG. 8A in accordance with some exemplary embodiments of the present disclosure.
Figure 8R:
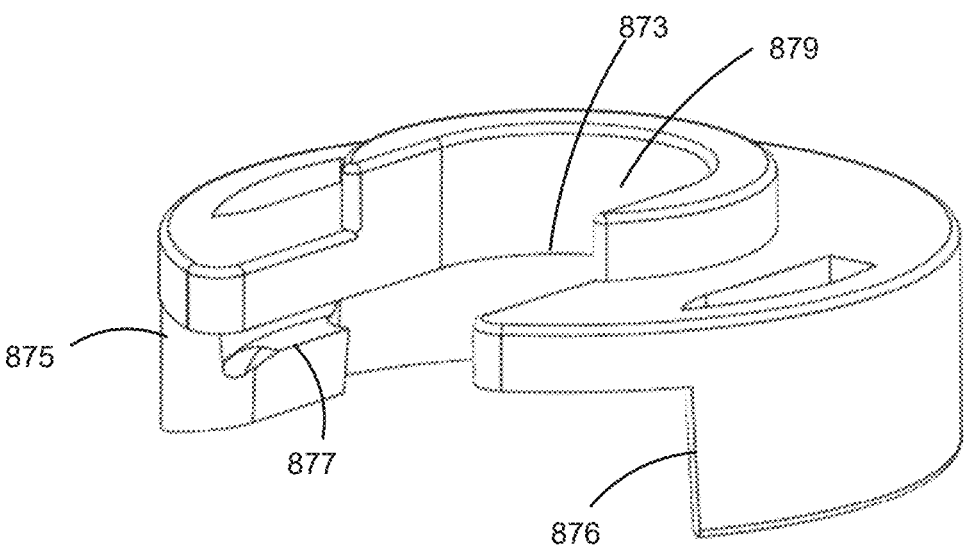

Referring to FIG. 8A-8R, there is depicted an exemplary apparatus, generally designated 800, in accordance with some exemplary embodiments of the present disclosure. In various embodiments, the apparatus 800 includes a dual function design with external drive and alignment features and internal features for compatibility with a variety of fluid and non-fluid connectors. Accordingly, the apparatus 800 is also referred herein as a coupler. In some embodiments, one of the key innovations is the dual function aspect of the design that can convert a variety of industry standard connectors into robot-grippable-robot-drivable (twist) connectors with specific features to accommodate axial misalignment during mating with the corresponding port. In some embodiments, the apparatus 800 is configured for facilitating automation of a connector, e.g., allowing a robot to operate the connector. The apparatus 800 generally includes a first coupling member and a second coupling member connected to or formed with the first coupling member. The first coupling member is configured for holding a first device and the second coupling member is configured for coupling with a second device (e.g., a port body or a port assembly disclosed herein). The second coupling member is also configured to serve as a robotic operable interface for a robot, such as a robotic end of arm tool (EOAT), to grip, hold and/or rotate.

Referring in particular to FIGS. 8A and 8C, in some embodiments, the apparatus 800 includes a first coupling member, such as the first coupling member 830, and a second coupling member, such as the second coupling member 850. The first coupling member includes a first side wall defining a first bore for receiving at least a portion of a first device. For instance, in some embodiments, the first coupling member 830 includes a first side wall 831 defining a first bore 832 for receiving at least a portion of a first device 810. In some embodiments, the first device 810 is a fluid connector, a gas connector, an electrical connector, or any combination thereof.

In some embodiments, the first coupling member is connected to the first device by a retainer. For instance, in the illustrated embodiment, the first coupling member 830 is connected to the first device 810 by a retainer 870. The retainer can be a component of the first device 810 or a component of the apparatus 800, and can be of any suitable shape and size. In some embodiments, the retainer 870 is a clip having an open side to allow the clip to fit on the first coupling member.

For instance, referring in particular to FIGS. 8F, 8M-8N and 8Q-8R, in some embodiments, the first coupling member 830 includes a first external recess and a second external recess, such as a first external recess 835 and a second external recess 836. The first and second external recesses are formed on the first side wall at or adjacent a distal end portion 834 of the first coupling member. In some embodiments, each of the first and second external recesses is a circumferential groove. The retainer 870 (e.g., the clip) includes an upper wall, an outer side wall, a first clip protrusion and a second clip protrusion, such as an upper wall 871, an outer side wall 874, a first clip protrusion 877 and a second clip protrusion 878. In some embodiments, the upper wall is configured for abutting a surface of the distal end portion of the first coupling member and a surface of the first device, thereby restricting the first device from moving relative to the first coupling member in a direction parallel or substantially parallel to the rotational axis of the apparatus. In some embodiments, the upper wall includes an outer curved edge and/or an inner curved edge, such as such as an outer curved edge 872 and/or an inner curved edge 873. The outer side wall extends downward from at least a portion of the outer curved edge of the upper wall and includes a first clip end and a second clip end, such as a first clip end 875 and a second clip end 876, at the open side of the clip. The first clip protrusion protrudes inward from the outer side wall at or adjacent to the first clip end and configured for engaging with the first external recess formed on the first side wall. The second clip protrusion protrudes inward from the outer side wall at or adjacent to the second clip end for engaging with the second external recess formed on the first side wall. In some embodiments, the clip further includes an inner side wall, such as an inner side wall 879, extending upward from at least a portion of the inner curved edge of the upper wall to assist in retaining the first device. However, the present disclosure is not limited thereof. The first coupling member and the clip can include additional, optional or alternative components, and can be coupled with each other by other means.

In some embodiments, the first coupling member 830 includes a mechanism to restrict the first device from rotating relative to the first coupling member around the rotational axis of the apparatus. For instance, referring in particular to FIGS. 8F-8N, in some embodiments, the first coupling member includes a plurality of first internal ribs, such as first internal ribs 841, formed on the first side wall and distributed circumferentially around the rotational axis of the apparatus. The plurality of first internal ribs is configured for abutting an external side wall 811 of the first device, thereby restricting the first device from rotating relative to the first coupling member around the rotational axis of the apparatus.

In some embodiments, the first coupling member 830 includes one or more external strengthening members, such as external strengthening members 843. The one or more external strengthening members are formed on the first side wall of the first coupling member to enhance the strength of the first coupling member. An external strengthening member can be of any type (e.g., rim, rib) and of any shape and size. In some embodiments, the one or more external strengthening members include one or more external rims, one or more external ribs, or any combination thereof. Advantageously, by including one or more external strengthening members, material can be cored out so that the first coupling member can be configured with a uniform or substantially uniform wall thickness for injection molding.

Referring in particular to FIGS. 8A, 8C and 8O-8P, the second coupling member 850 is connected to or formed with the first coupling member at a proximal end portion of the first coupling member. As used herein, a proximal end portion of the first coupling member (e.g., a proximal end portion 833) refers to a portion of the first coupling member that is closer to the second coupling member and a distal end portion of the first coupling member (e.g., a distal end portion 834) refers to a portion of the first coupling member that is away from the second coupling member. Similarly, a proximal end portion (e.g., a proximal end portion 853) of the second coupling member refers to a portion of the second coupling member that is closer to the first coupling member and a distal end portion (e.g., a distal end portion 854) of the second coupling member refers to a portion of the second coupling member that is away from the first coupling member. In the embodiment illustrated in FIGS. 8A and 8B, the proximal end portion of the first coupling member is a lower end portion of the first coupling member and a distal end portion of the first coupling member is an upper end portion of the first coupling member. The proximal end portion of the second coupling member is an upper end portion of the second coupling member and a distal end portion of the second coupling member is a lower end portion of the first coupling member.

In some embodiments, the second coupling member 850 includes a second side wall, such as a second side wall 851. The second side wall defines a second bore, such as a second bore 852. In some embodiments, the first coupling member and the second coupling member are individual parts, for instance, each formed by an injection molding of a plastic (e.g., a medical grade plastic). The first coupling member and the second coupling member are connected to each other, for instance, by ultrasonic welding, adhesive bonding, or other means. In some embodiments, the proximal end portion of the first coupling member is inserted into the proximal end portion of the second coupling member, e.g., inserted into a portion of the second bore formed at the proximal end portion of the second coupling member. The first coupling member includes an external flange, such as an external flange 844, at or adjacent the proximal end portion 833 of the first coupling member. The second coupling member includes a shoulder, such as a shoulder 855, at or adjacent the proximal end portion of the second coupling member. The shoulder of the second coupling member is configured to hold the external flange of the first coupling member. The external flange of the first coupling member and the shoulder of the second coupling member are connected to each other, for instance, by ultrasonic welding, adhesive bonding, or other means.

In some embodiments, at least one of the first coupling member 830 and the second coupling member 850 includes a mechanism to assist in securing the first coupling member with the second coupling member. For instance, referring in particular to FIGS. 8H and 8M-8N, in some embodiments, the proximal end portion of the first coupling member includes a plurality of first external ribs, such as first external ribs 842. The plurality of first external ribs is formed on the first side wall and distributed circumferentially around the rotational axis of the apparatus for abutting the proximal end portion of the second coupling member, e.g., abutting an inner surface of the proximal end portion of the second coupling member, thereby help to secure the first coupling member with the second coupling member.

Referring in particular to FIG. 8A, in various embodiments, the second side wall 851 of the second coupling member has an exterior surface defined by revolving a continuous curve about a rotational axis of the apparatus to facilitate operation by a robotic arm. For instance, in some embodiments, the second side wall has an exterior surface 860 defined by revolving a continuous curve about a rotational axis, such as a rotational axis 820, of the apparatus. A continuous curve can be a smooth curve, a piecewise smooth curve, or a non-smooth curve. As a non-limiting example, it is illustrated that the exterior surface 860 is defined by revolving a piecewise smooth curve comprised of three smooth segments, each being a straight or substantially straight line.

In some embodiments, the revolving exterior surface includes a first revolving segment, such as a first revolving segment 861, proximal to the first coupling member. The revolving exterior surface also includes a second revolving segment, such as a second revolving segment 864, distal to the first coupling member. The first and second revolving segments of the revolving exterior surface can be but do not have to be identical or symmetrical to each other. As a non-limiting example, the first and second revolving segments of the revolving exterior surface are illustrated to be identical or substantially identical (e.g., substantially the same in size and shape).

In some embodiments, each of the first and second revolving segments of the revolving exterior surface has a first side and a second side that is narrower than the first side. For instance, the first revolving segment 861 has a first side 862 and a second side 863 that is narrower than the first side 862, and the second revolving segment 864 has a first side 865 and a second side 866 that is narrower than the first side 165. The second sides of the first and second revolving segments of the revolving exterior surface (e.g., the second side 863 and the second side 865) face each other.

In some embodiments, the first or second revolving segment of the revolving exterior surface is a non-cylindrical segment. In some embodiments, each of the first and second revolving segments of the revolving exterior surface is a non-cylindrical segment. For instance, in an exemplary embodiment, one of the first and second revolving segments of the revolving exterior surface is a conical or substantially conical surface (e.g., a revolving surface defined by a slanted straight line or a slanted substantially straight line), and the other of the first and second revolving segments of the revolving exterior surface is an inverted conical or substantially conical surface. In some embodiments, the revolving exterior surface further includes a third revolving segment, such as a third revolving segment 867. The third revolving segment is disposed between the first and second revolving segments and connects the second side of the first revolving segment with the second side of the second revolving segment. In an exemplary embodiment, the third revolving segment of revolving exterior surface is a cylindrical or substantially cylindrical surface (e.g., a revolving surface defined by a straight or substantially straight line). However, the present disclosure is not limited thereto. The revolving exterior surface can have other shapes. For instance, the revolving exterior surface can include a single revolving segment or more than three revolving segments.

Referring in particular to FIGS. 8I-8L and 8O-8P, the second bore 852 of the second coupling member is configured to receive at least a portion of a second device, such as a port body or a port assembly disclosed herein. In some embodiments, the second coupling member 850 includes an internal chamfer, such as an internal chamfer 856. The internal chamfer is formed at the second end portion of the second coupling member and configured to guide connection of the apparatus 800 with the second device (e.g., the port body 200, 400, or 500). In some embodiments, the second coupling member includes a plurality of second internal ribs, such as second internal ribs 857. The plurality of second internal ribs is on the second side wall of the second coupling member and distributed circumferentially around the rotational axis of the apparatus. In some such embodiments, the internal chamfer is formed collectively by the plurality of second internal ribs, e.g., the plurality of second internal ribs defines the chamfer angle and chamfer length of the internal chamfer. Like the one or more strengthening members of the first coupling member, the plurality of second internal ribs advantageously allows for the design of the second coupling member with a uniform or substantially uniform wall thickness while meeting required strength and/or other properties.

In some embodiments, the second coupling member 850 includes a recess, such as a recess 858, formed circumferentially on the second side wall (e.g., an inner surface of the second side wall) of the second coupling member at or adjacent the internal chamfer. The recess can have any suitable shape and size. In an exemplary embodiment, the recess 858 is a tapered internal recess. The recess in general will reduce the stiffness of the second coupling member and thus facilitate smooth interaction between the apparatus and the second device.

Referring to FIGS. 9A-9F, there is depicted an exemplary robotic end of arm tool (EOAT), generally designated 900, in accordance with some exemplary embodiments of the present disclosure. This robotic EOAT includes a novel robotic grasp and rotate mechanism. In some embodiments, this robotic EOAT includes the combination of axial grasping with position control along the rotation axis, and the simultaneous ability to rotate the grasped part (e.g., a coupler) via a friction drive wheel against the exterior of the part (hold and rotate the part while the EOAT body remains stationary).

In some embodiments, this robotic EOAT is configured for operating a part that includes a revolving exterior surface around a rotational axis of the part. In some embodiments, the revolving exterior surface includes a first non-cylindrical segment and a second non-cylindrical segment. For instance, in some embodiments, the part is configured the same as or similarly to the apparatus 800, which includes the revolving exterior surface 860 having a first non-cylindrical segment 861 and a second non-cylindrical segment 864.

In some embodiments, the robotic EOAT includes a support, a first jaw, a second jaw, and a wheel, such as a support 910, a first jaw 920, a second jaw 930, and a wheel 940. In some embodiments, the first jaw, the second jaw and the wheel are disposed at a side of the support.

The first jaw and the second jaw are connected to the support and operable between an open position and a closed position for gripping and releasing the part (e.g., the coupler 800). The first and second jaws can be but do not have to be identical or substantially symmetrical to each other with respect to the wheel. As a non-limiting example, the first and second jaws are illustrated to be substantially the same and substantially symmetrical to each other with respect to the wheel.

In some embodiments, to facilitate gripping and/or rotating of the part (e.g., the coupler 800), each of the first and second jaws includes a first contact bearing and a second contact bearing. In some embodiments, each of the first and second jaws is split like a split finger or fork. For instance, in an exemplary embodiment, the first jaw 920 includes a first contact bearing 921 and a second contact bearing 922, and the second jaw 930 includes a first contact bearing 931 and a second contact bearing 932. A bearing in the first and second contact bearings of the first and second jaws can be any suitable type of bearings including but not limited to a ball of a ball transfer unit. The first and second contact bearings of the first or second jaw can be but do not have to be aligned in a direction parallel or substantially parallel to the rotational axis of the wheel. As a non-limiting example, it is illustrated that the first and second contact bearings of the first jaw are aligned with each other in a direction substantially parallel to the rotational axis of the wheel, and the first and second contact bearings of the second jaw are aligned with each other in a direction substantially parallel to the rotational axis of the wheel.

In some embodiments, each of the first and second jaws includes a jaw surface, and the first and second contact bearings are disposed at the jaw surface. For instance, in some embodiments, the first jaw 920 includes a first jaw surface 923, at which the first contact bearing 921 and the second contact bearing 922 are disposed. Similarly, the second jaw 930 includes a second jaw surface 933, at which the first contact bearing 931 and the second contact bearing 932 are disposed.

Figure 9A:
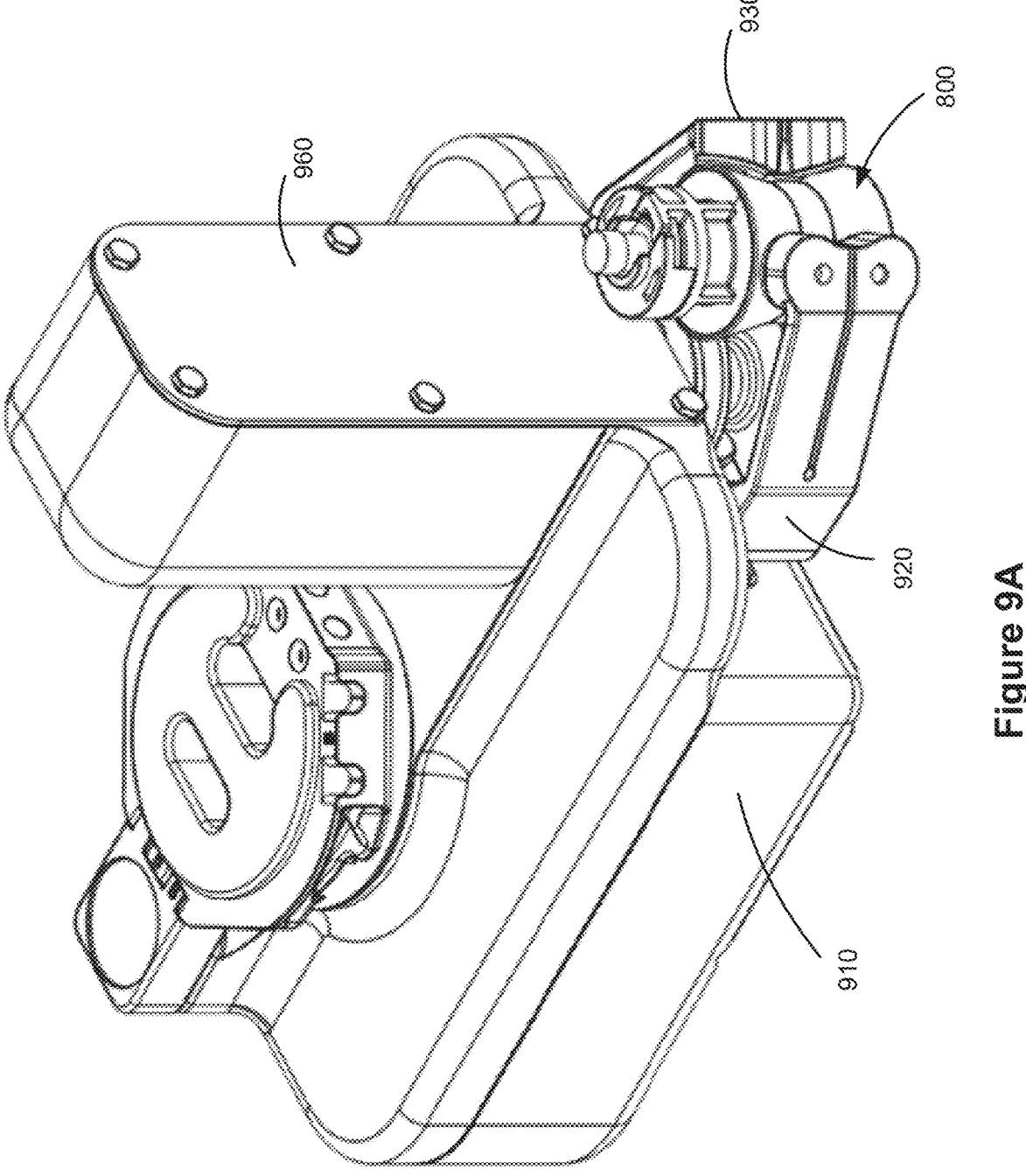
FIG. 9A is a perspective view illustrating an exemplary robotic end of arm tool (EOAT) for operating the exemplary apparatus of FIG. 8A in accordance with some exemplary embodiments of the present disclosure.
Figure 9B:
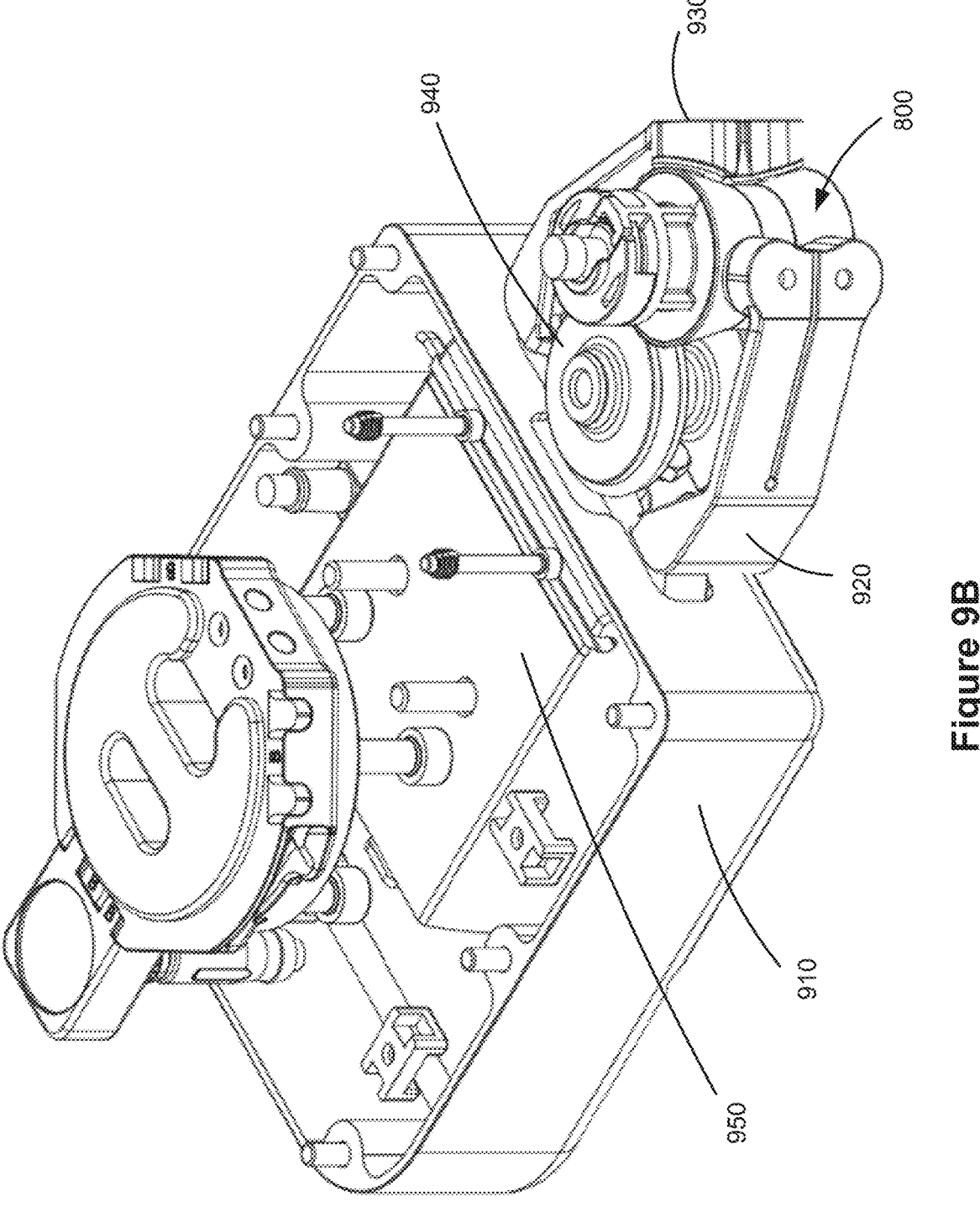
FIG. 9B is a perspective view illustrating the exemplary EOAT of FIG. 9A, where some components are removed to show an interior of the exemplary EOAT of FIG. 9A.
Figure 9C:
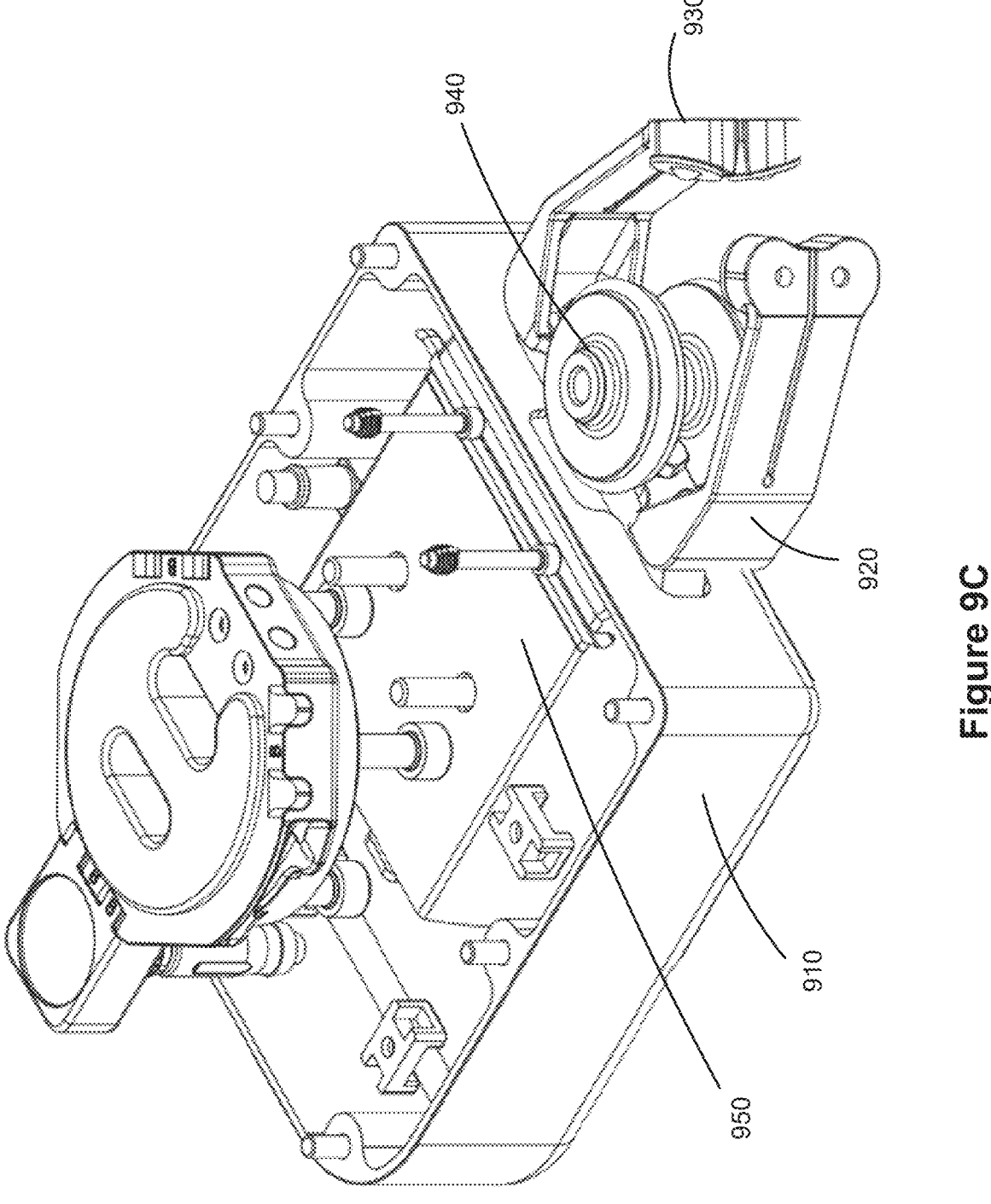
FIG. 9C is a perspective view illustrating the exemplary EOAT of FIG. 9B, where the exemplary apparatus of FIG. 8A is removed.
Figure 9D:
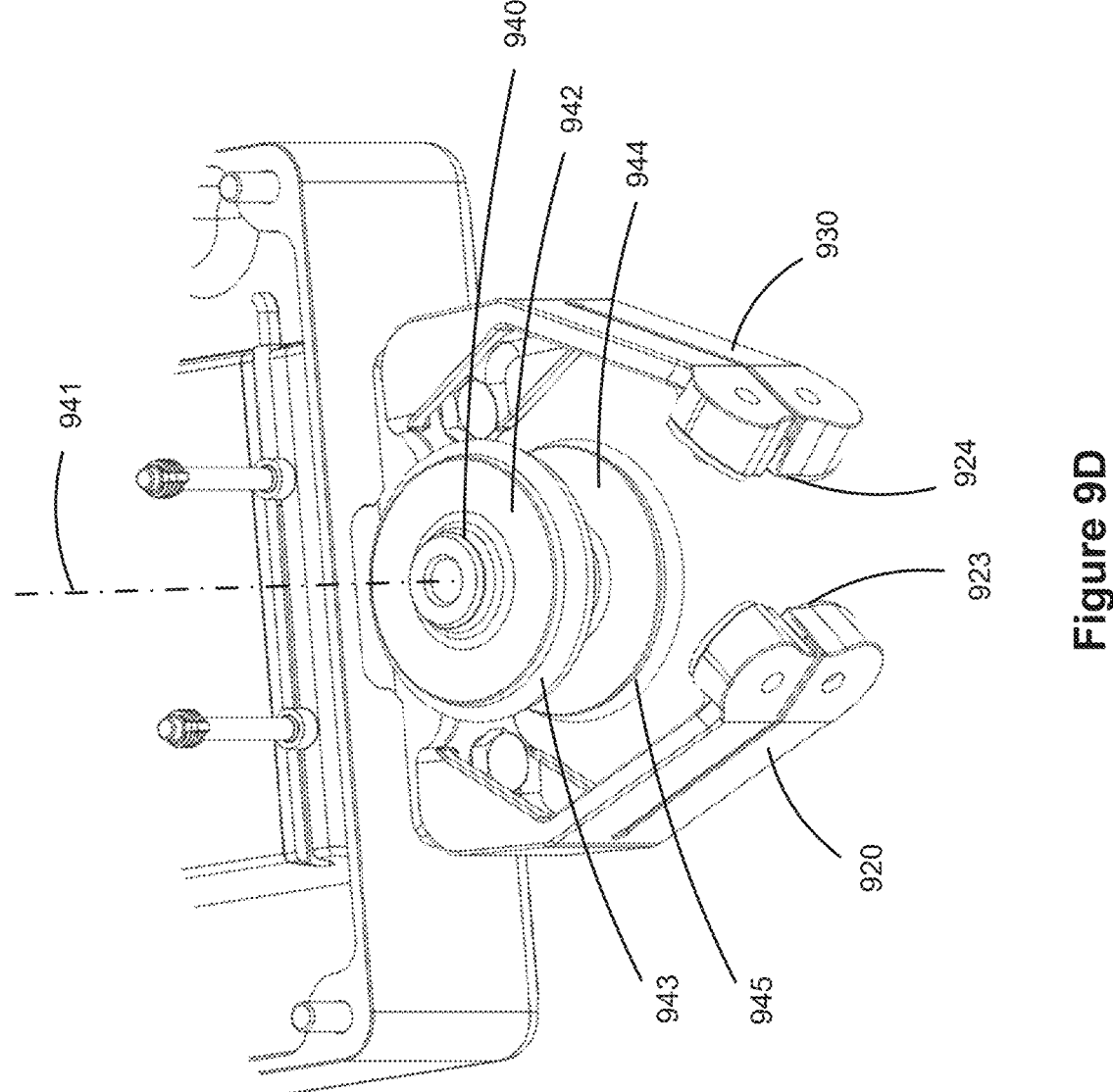
FIG. 9D is a perspective view illustrating a portion of the exemplary EOAT of FIG. 9C.
Figure 9E:
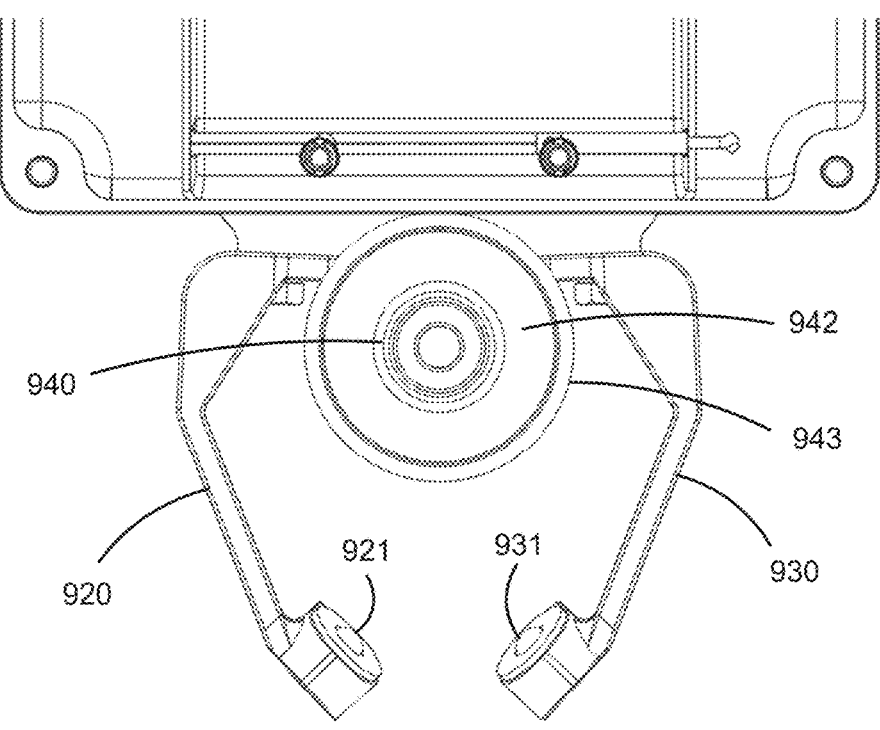
FIG. 9E is a top view illustrating a portion of the exemplary EOAT of FIG. 9C.
Figure 9F:
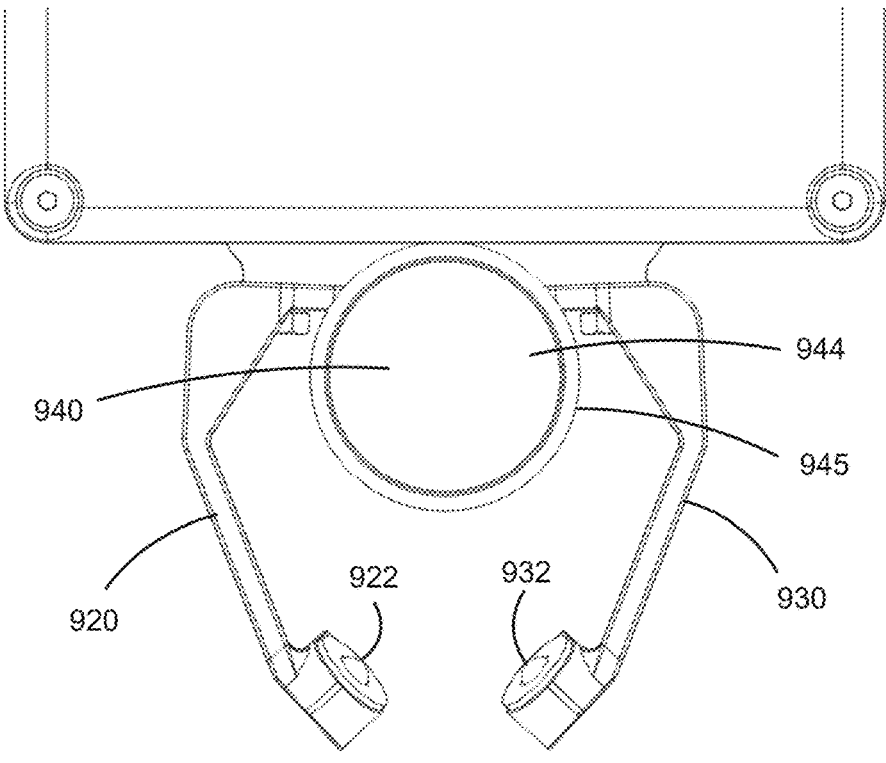
FIG. 9F is a bottom view illustrating a portion of the exemplary EOAT of FIG. 9C.

In some embodiments, to further assist in gripping and/or rotating of the part (e.g., the coupler 800), the first or second jaw surface is profiled in accordance with the revolving exterior surface of the part (e.g., the revolving exterior surface 860 of the coupler 800). For instance, in some embodiments, each of the first and second jaw surfaces includes a first segment and a second segment profiled respectively in accordance with the first revolving segment 861 and second revolving segment 862 of the revolving exterior surface of the part as illustrated in FIGS. 9A and 9B.

The wheel is connected to the support and operable to rotate around a rotational axis, such as a rotational axis 941, of the wheel. In some embodiments, the wheel includes a first rim and a second rim, such as a first rim 942 and a second rim 944. In some embodiments, each of the first and second rims of the wheel includes a tire. For instance, the first rim 942 includes a first tire 943 and the second rim 944 includes a second tire 945. The first and second tires can be made of any suitable material including but not limited to silicone rubber. In some embodiments, the first or second tire is an O-ring.

When the first and second jaws are in the closed position with the part (e.g., the coupler 800) in between, the first contact bearing of the first jaw, the first contact bearing of the second jaw and the first rim of the wheel are leveled with or substantially with each other and abut the first non-cylindrical segment of the revolving exterior surface of the part (e.g., the coupler 800). Similarly, the second contact bearing of the first jaw, the second contact bearing of the second jaw and the second rim of the wheel are leveled with or substantially with each other and abut the second non-cylindrical segment of the revolving exterior surface of the part (e.g., the coupler 800). This not only restricts the part (e.g., the coupler 800) from moving axially but also restricts the part (e.g., the coupler 800) from moving translationally in a plane perpendicular or substantially perpendicular to the rotational axis of the part (e.g., the coupler 800). In the meantime, this allows the wheel to rotate the part (e.g., the coupler 800) to rotate around the rotational axis of the part (e.g., the coupler 800), thereby facilitating connection of the device held by the part (e.g., the device 810 held by the coupler 800) with another device (e.g., the device 110 held by a port body disclosed herein).

In some embodiments, the robotic EOAT includes additional, optional or alternative components. For instance, in some embodiments, the robotic BOAT includes an actuator, such as an actuator 950, to open and close the first and second jaws, a motor, such as a motor 960, to drive the wheel, or both of the actuator and the motor. In some such embodiments, the first and second jaws are connected to the support through the actuator, and the wheel is connected to the support through the motor.

Figure 10A:
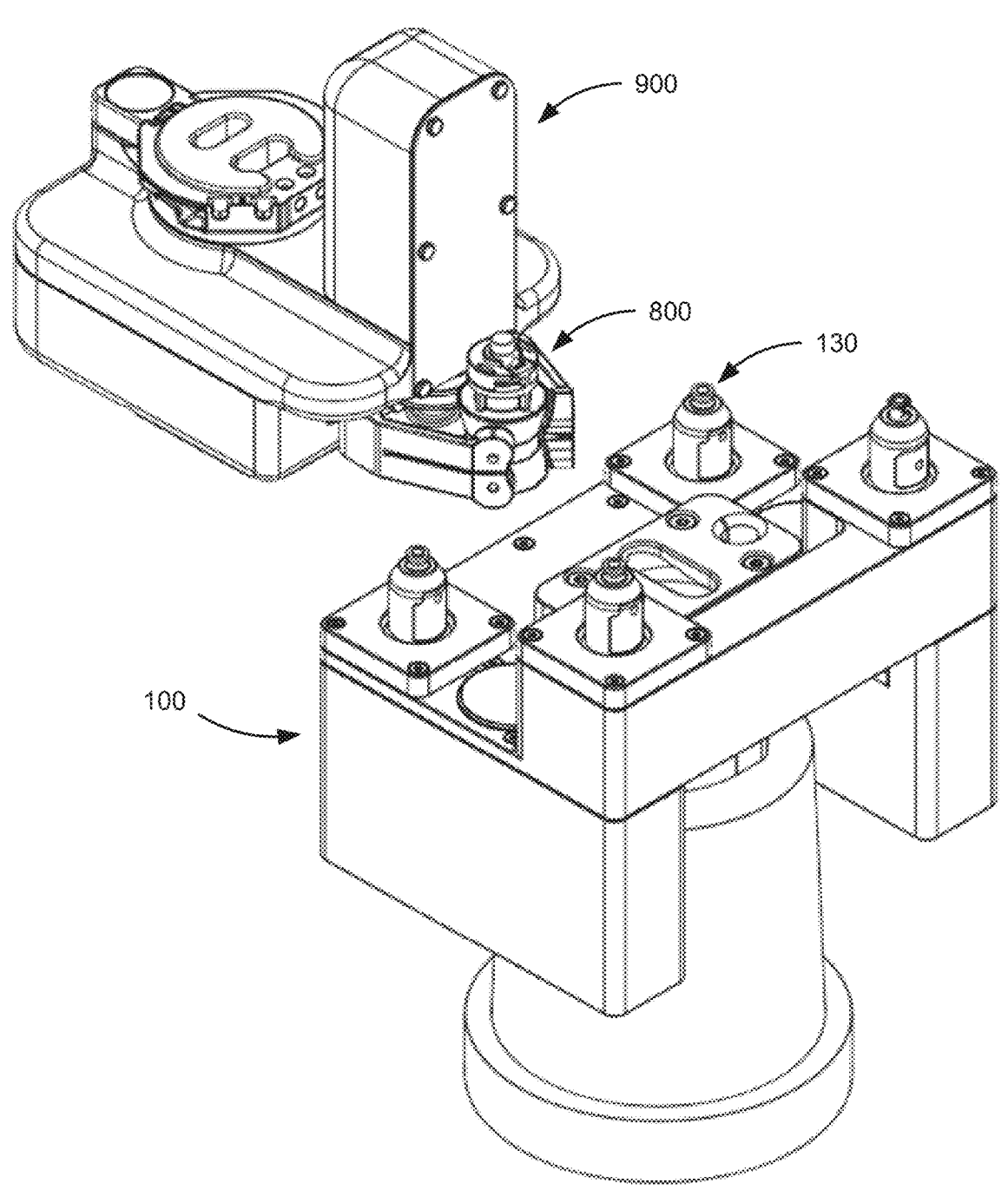
FIGS. 10A and 10B are perspective views illustrating an exemplary process for connecting two devices in accordance with some exemplary embodiments of the present disclosure.
Figure 10B:
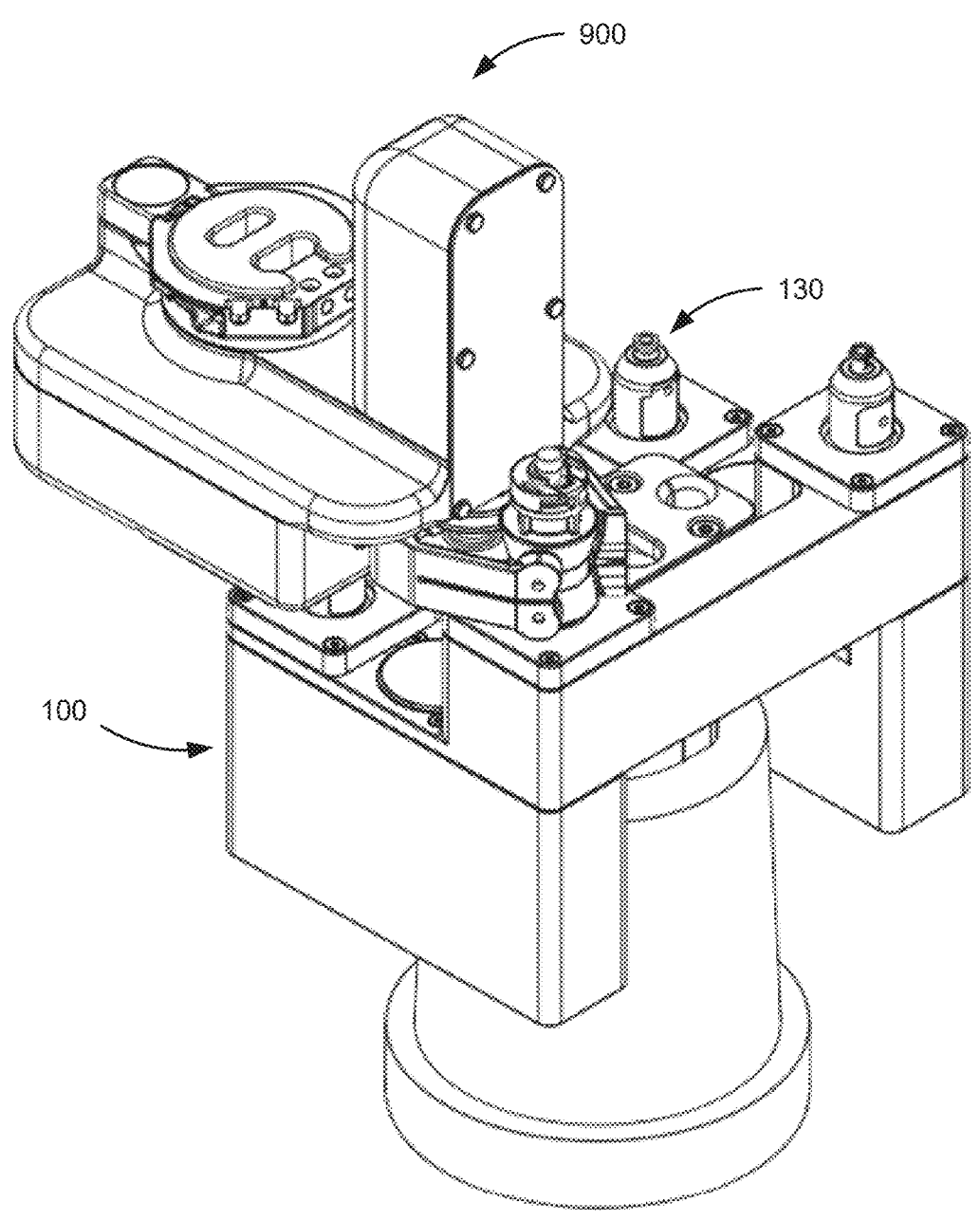
Figure 10C:
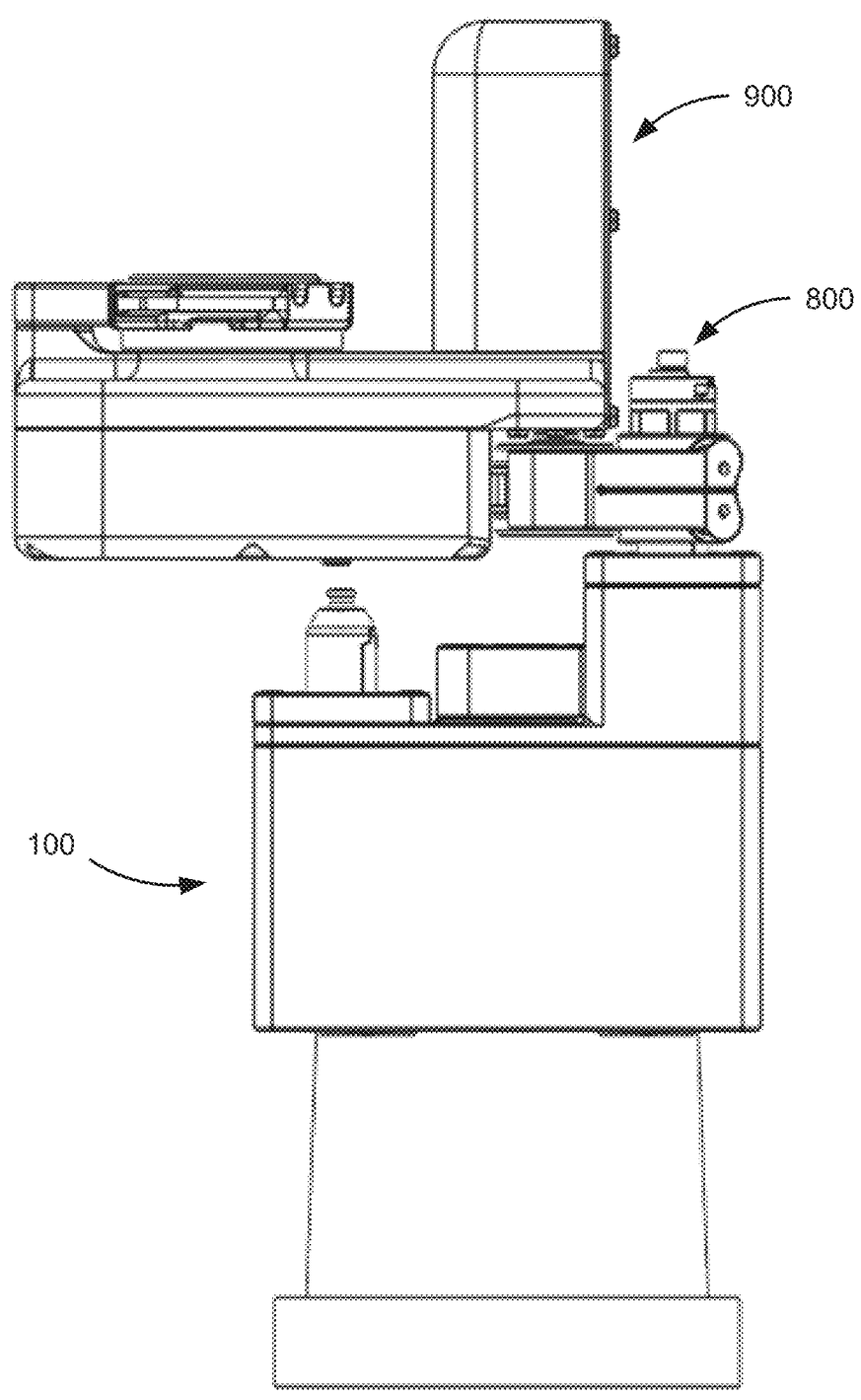
FIG. 10C is a side view illustrating the exemplary process of FIG. 10B.

Referring to FIGS. 10A-10G, there is depicted an exemplary process, generally designated 1000, for connecting two devices in accordance with some exemplary embodiments of the present disclosure. While FIGS. 10A-10C illustrate the use of the exemplary robotic EOAT 900 for coupling the exemplary apparatus of FIG. 8A with an exemplary port assembly (e.g., a connection unit) 130 disposed at an exemplary cartridge 100, it should be noted that this is by way of example and it is non-limiting. Other robotic EOAT can be used to couple the exemplary apparatus of FIG. 8A with an exemplary port assembly. Moreover, the exemplary apparatus of FIG. 8A can be coupled with other port assemblies including but not limited to those disclosed herein. Further, a port assembly to be coupled with the exemplary apparatus of FIG. 8A can be a standalone device or a component disposed at other devices including but not limited to the cartridges disclosed herein.

Figures 10D, 10E, 10F, 10G:
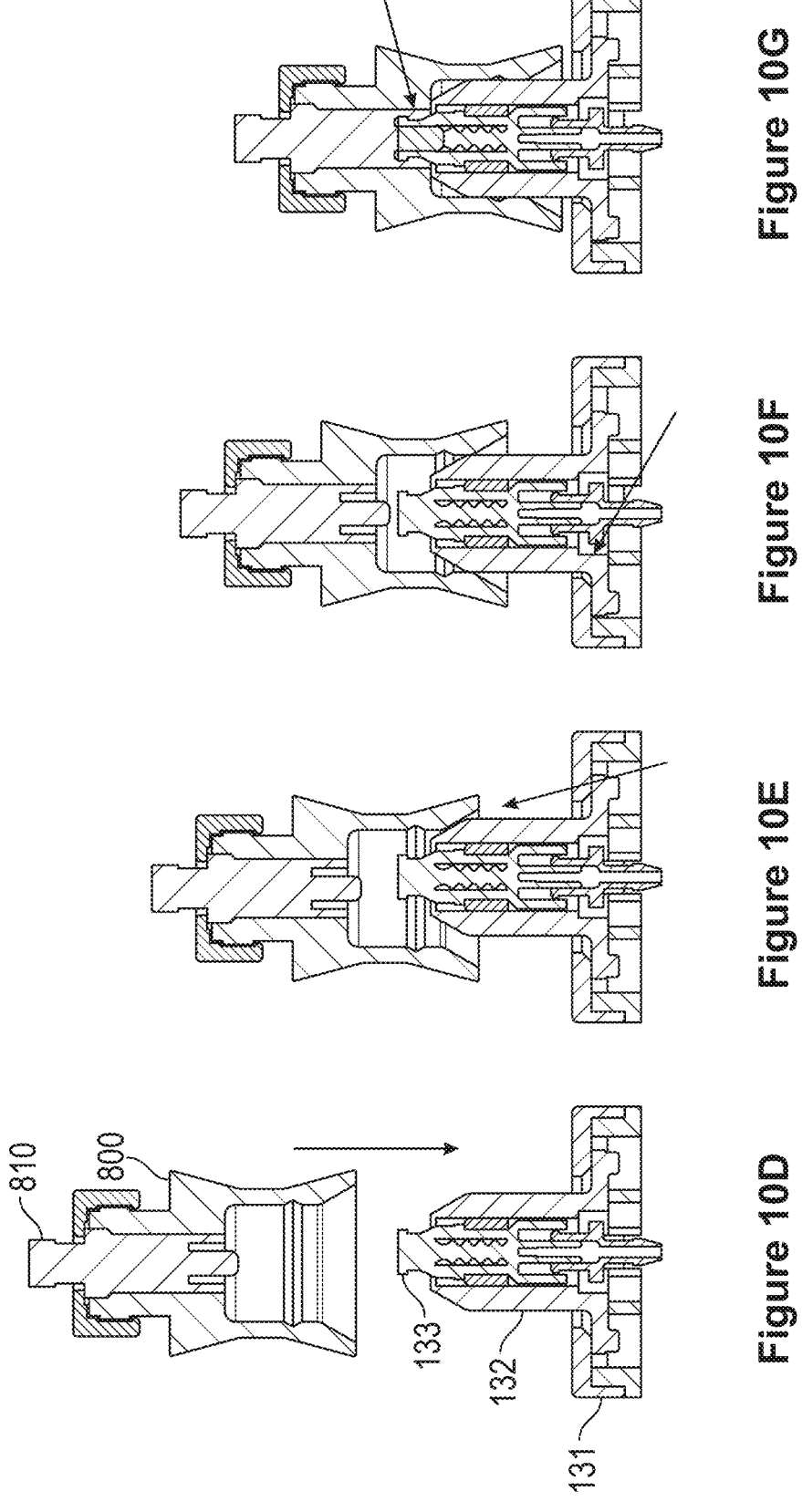
FIGS. 10D, 10E, 10F and 10G are cross-sectional views collectively illustrating an exemplary process that accommodates axial misalignment when connecting the two devices in accordance with some exemplary embodiments of the present disclosure.

In some embodiments, the port body (e.g., the port body 132) holds a first device (e.g., the device 133), and the coupler 800 holds a second device (e.g., the second device 810). The port body and the coupler are moved relative to each other, for instance, by moving the coupler (and thus the second device) toward the port body using the robotic EOAT 900 as illustrated in FIGS. 10A, 10B and 10D. Unless the port body and the coupler are precisely aligned with each other (which is unusual and difficult in automation), the coupler (e.g., the inner chamfer 856 of the coupler 800) will form a first contact with the tip of the port body as illustrated in FIG. 10E. Through this contact, the coupler pushes the port body when moved further toward the port body. Pushed by the coupler and constrained by the retainer (e.g., the retainer 131), the port body moves translationally relative to the retainer, thereby aligning the first device held by the port body with the second device held by the coupler as illustrated in FIG. 10F. Thus, advantageously, this accommodates axial misalignment if necessary when connecting the first and second devices. The first and second devices can then be connected to each other by moving the coupler further toward the port body and/or rotating the coupler relative to the port body as illustrated in FIG. 10G.

The devices and apparatuses of the present disclosure can be used alone or in combination with other devices to implement automated production of cellular engineering targets (e.g., cell therapies) at a biological foundry. Moreover, the components of the devices and the apparatuses (e.g., the port body, the retainer, the coupler, the EOAT) disclosed herein are combinable in any useful number and combination. Further, at least some components of the apparatuses disclosed herein (e.g., the port body, the coupler) can be used alone or in combination with other devices different than the apparatuses disclosed herein.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A cartridge for facilitating automation of a vessel, wherein the vessel comprises a cap and at least one vessel port, the cartridge comprising:

a cartridge body comprising a side wall, an upper wall connected to or formed with an upper portion of the side wall, and an interior defined by the side wall and the upper wall;

an adapter disposed in the interior of the cartridge body and connected to or formed with the cartridge body, wherein the adapter is configured for removably connecting the vessel to the cartridge body;

at least one connection structure, each respective connection structure in the at least one connection structure comprising:

a corresponding retainer fixed on or integrally formed with the upper wall of the cartridge body;

a corresponding port body coupled to the corresponding retainer and having a corresponding distal end portion positioned exterior to the cartridge body;

a corresponding connector housed by the corresponding port body and having a corresponding first end outside of the cartridge body and a corresponding second end; and a corresponding tube for connecting the corresponding second end of the corresponding connector to a vessel port in the at least one vessel port; and a plurality of locking elements disposed at a lower portion of the side wall of the cartridge body to facilitate positioning and locking of the cartridge.

2. The cartridge of claim 1, wherein the vessel is a gas permeable rapid expansion bioreactor device.

3. The cartridge of claim 1, wherein the at least one vessel port is formed at the cap of the vessel.

4. The cartridge of claim 1, wherein an interior surface of the side wall comprises:

a first interior surface segment;

a second interior surface segment parallel or substantially parallel to the first interior surface segment; and a third interior surface segment between the first and second interior surface segments, wherein each of the first and second interior surface segments is planar or substantially planar, and the third interior surface segment is curved in accordance with the vessel.

5. The cartridge of claim 1, wherein an exterior surface of the side wall comprises:

a first exterior surface segment;

a second exterior surface segment parallel or substantially parallel to the first exterior surface segment; and a third exterior surface segment between the first and second exterior surface segments, wherein each of the first, second, and third exterior surface segments is planar or substantially planar, and the third exterior surface segment is perpendicular or substantially perpendicular to the first and second exterior surface segments.

6. The cartridge of claim 1, wherein the at least one connection structure comprises a plurality of connection structures.

7. The cartridge of claim 6, wherein:

the upper wall of the cartridge body comprises a first upper wall segment and a second upper wall segment, wherein the first and second upper wall segments are at different heights; and at least one retainer in the corresponding retainers of the plurality of connection structures is fixed on or integrally formed with each of the first and second upper wall segments.

8. The cartridge of claim 7, wherein more than one retainer in the corresponding retainers of the plurality of connection structures are fixed on or integrally formed with the first or second upper wall segment.

9. The cartridge of claim 1, wherein the corresponding port body is movable translationally relative to the corresponding retainer in a plane perpendicular or substantially perpendicular to an axial direction of the corresponding port body.

10. The cartridge of claim 1, wherein for each respective connection structure in the at least one connection structure:

the corresponding port body comprises:

a base;

a stem extending from the base; and one or more first anti-rotation structures disposed at the base; and the corresponding retainer comprises:

a first retaining structure having a first surface;

a second retaining structure coupled or formed with the first retaining structure and having a second surface spaced apart from the first surface of the first retaining structure in an axial direction of the corresponding port body, wherein the base of the corresponding port body is disposed between the first surface of the first retaining structure and the second surface of the second retaining structure;

a first circular or substantially circular through-hole disposed on the first retaining structure and having a diameter larger or substantially larger than an outer diameter of the stem to allow the stem of the corresponding port body to pass through and to move relative to the first retaining structure; and one or more second anti-rotation structures disposed at the first retaining structure or the second retaining structure and coupled with the one or more first anti-rotation structures to restrict the corresponding port body from rotating relative to the retainer.

11. The cartridge of claim 10, wherein the second retaining structure of the corresponding retainer of each respective connection structure in the at least one connection structure is a portion of the upper wall of the cartridge body.

12. The cartridge of claim 1, wherein the adapter is coupled to the upper wall of the cartridge body and the cap of the vessel.

13. The cartridge of claim 1, wherein the adapter comprises at least one slot for accommodating the at least on vessel port, the corresponding tube of each respective connection structure in at least one connection structure, or any combination thereof.

14. The cartridge of claim 1, wherein the adapter comprises (i) an internal flange for inserting into a gap between the cap and a body of the vessel, and (ii) a plurality of internal ribs for abutting a side wall of the cap, thereby restricting the cap of the vessel from moving relative to the cartridge body.

15. The cartridge of claim 1, wherein the corresponding retainer restricts axial and rotational movement of the corresponding port body but allows translational movement of the corresponding port body relative to the corresponding retainer in a plane perpendicular substantially perpendicular to an axial direction of the corresponding port body.

16. The cartridge of claim 1, further comprising:

an interface structure disposed at the side wall or the upper wall of the cartridge body to facilitate operation by a robotic end of arm tool (EOAT).

17. The cartridge of claim 16, wherein the interface structure is disposed at a middle portion of the upper wall of the cartridge body.

18. The cartridge of claim 16, wherein the interface structure comprises:

a first interface surface facing away from the side wall or the upper wall of the cartridge body, wherein the first interface surface is planar or substantially planar;

a second interface surface facing toward the side wall or the upper wall of the cartridge body;

an elongated slot formed through the first interface surface to allow an elongated cam bar of the EOAT to insert into the interface structure; and a recess recessed from the second interface surface toward the first interface surface, wherein the recess has a dimension larger than a width of the elongated slot and a length of the elongated cam bar, thereby allowing the elongated cam bar of the EOAT to rotate and engage with the interface structure.

19. The cartridge of claim 18, wherein the recess is a circular blind hole formed through the second interface surface and aligned with the elongated slot.

20. The cartridge of claim 18, wherein the recess has a bottom surface within the interface structure that is curved or slanted relative to the first interface surface.

21. The cartridge of claim 18, further comprising:

a plurality of first alignment elements to facilitate alignment of the interface structure with the EOAT.

22. The cartridge of claim 21, wherein a first alignment element in the plurality of first alignment elements is a pin or a pin hole.

23. The cartridge of claim 1, further comprising:

a plurality of second alignment elements formed at a lower portion of the side wall of the cartridge body to facilitate alignment and positioning of the cartridge on a dock.

24. The cartridge of claim 23, wherein a second alignment element in the plurality of second alignment elements is a pin or a pin hole.

25. The cartridge of claim 1, wherein a locking element in the plurality of locking elements is an electromagnet or an electromagnet target.

* * * * *